(12) United States Patent
Sahin et al.

(10) Patent No.: US 11,673,939 B2
(45) Date of Patent: Jun. 13, 2023

(54) COMPOSITIONS AND METHODS FOR DIAGNOSIS AND TREATMENT OF CANCER

(71) Applicant: BioNTech SE, Mainz (DE)

(72) Inventors: Ugur Sahin, Mainz (DE); Bonny Gaby Lui, Mainz (DE); Nadja Salomon, Hochheim (DE); Joycelyn Wüstehube-Lausch, Mainz (DE); Matin Daneschdar, Mainz (DE); Hans-Ulrich Schmoldt, Mainz (DE); Markus Fiedler, Halle (DE)

(73) Assignee: BIONTECH SE

(*) Notice: Subject to any disclaimer, the term of this patent is extended or adjusted under 35 U.S.C. 154(b) by 0 days.

(21) Appl. No.: 16/972,794

(22) PCT Filed: Jun. 6, 2019

(86) PCT No.: PCT/EP2019/064872
§ 371 (c)(1),
(2) Date: Dec. 7, 2020

(87) PCT Pub. No.: WO2019/234190
PCT Pub. Date: Dec. 12, 2019

(65) Prior Publication Data
US 2021/0246191 A1    Aug. 12, 2021

(30) Foreign Application Priority Data
Jun. 8, 2018 (WO) ............... PCT/EP2018/065205

(51) Int. Cl.
| C07K 14/78 | (2006.01) |
| C07K 1/107 | (2006.01) |
| G01N 33/574 | (2006.01) |
| G01N 33/68 | (2006.01) |
| A61K 38/00 | (2006.01) |

(52) U.S. Cl.
CPC ............ *C07K 14/78* (2013.01); *C07K 1/1075* (2013.01); *G01N 33/574* (2013.01); *G01N 33/68* (2013.01); *A61K 38/00* (2013.01)

(58) Field of Classification Search
None
See application file for complete search history.

(56) References Cited

FOREIGN PATENT DOCUMENTS

| EP | 2 360 172 A2 | 8/2011 | |
| WO | 2008/022759 A2 | 2/2008 | |
| WO | 2016/022597 A1 | 2/2016 | |
| WO | WO-2017049009 A1 * | 3/2017 | ............. A61K 38/00 |

OTHER PUBLICATIONS

Lui et al. "Targeting the tumor vasculature with engineered cystine-knot miniproteins" Nature Communications 11:295. (Year: 2020).*
Gebauer et al., "Combinatorial Design of an Anticalin Directed against the Extra-Domain B for the Specific Targeting of Oncofetal Fibronectin", Journal of Molecular Biology, 2012, 425(4), 780-802.
Park et al., "Fibronectin extra domain B-specific aptide conjugated nanoparticles for targeted cancer imaging", Journal of Controlled Release, 2012, 163(2), 111-118.
Castellani et al., "The Fibronectin Isoform Containing the ED-B Oncofetal Domain: A Marker of Angiogenesis", International Journal of Cancer, 1994, 59(5), 612-618.
Moore et al., "Engineered knottin peptide enables noninvasive optical imaging of intracranial medulloblastoma", Proceedings of the National Academy of Sciences (PNAS), 2013, 110(36), 14598-14603.

* cited by examiner

*Primary Examiner* — Sudhakar Katakam
*Assistant Examiner* — Zachary J Miknis
(74) *Attorney, Agent, or Firm* — McDonnell Boehnen Hulbert & Berghoff LLP

(57) ABSTRACT

The present invention relates to the diagnosis and treatment of diseases expressing Fibronectin Extra Domain B (EDB) such as diseases characterized by tissue remodeling and/or angiogenesis, in particular cancerous diseases, such as head and neck, brain, colorectal, lung, prostate and breast cancer. More particularly, the invention concerns peptides targeting Fibronectin Extra Domain B.

Figure 1:
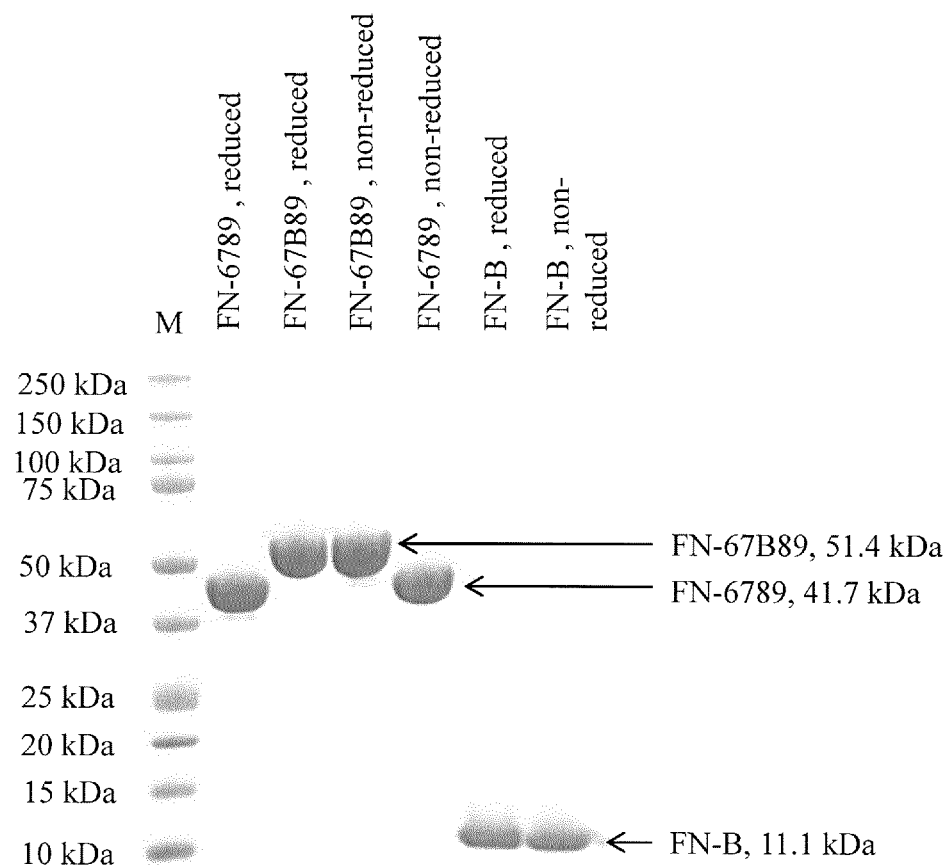
Figure 1:
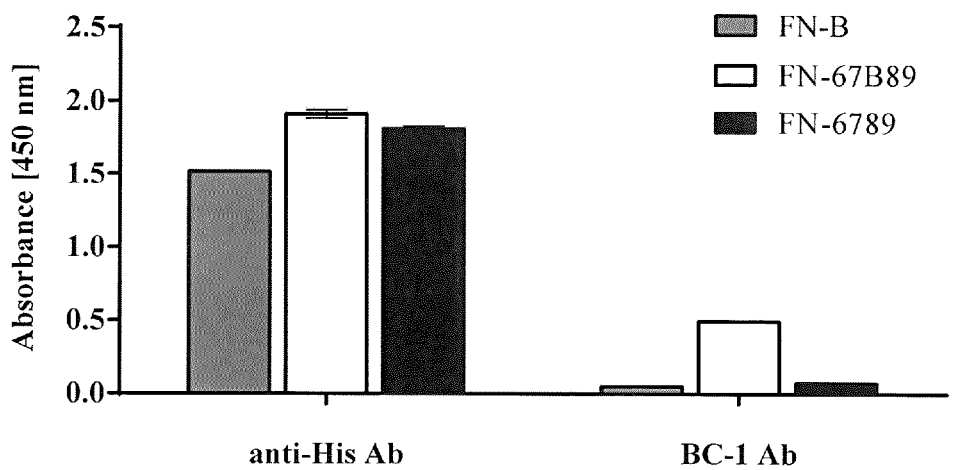

19 Claims, 22 Drawing Sheets
Specification includes a Sequence Listing.

A

B

Figure 2

| Clone name | Cystine-knot miniprotein sequence | Proportion of total sequences (%) |
|---|---|---|
| MCopt 1.0-2 | WKCQPTNGYRIRCRRDSDCPGDCICRGNGYCG | 40 |
| MCopt 2.0-2 | SVCKNVSIMRIRLCRRDSDCPGACICRGNGYCG | 13 |
| MCopt 2.0-1 | SVCAHYNTIRVRLCRRDSDCPGACICRGNGYCG | 10 |
| MCopt 1.0-1 | WTCTKKYPNTISCRRDSDCRVTCICRGNGYCG | 4 |
| MCopt 1.0-3 | PMCTQRKNRIRLCRRDSDCTGACICRGNGYCG | 2 |
| MCopt 2.0-3 | SVCKQANFVRIRLCRRDSDCPGACICRGNGYCG | 2 |

| Clone name | Ranking value | Protein sequence |
|---|---|---|
| MCopt1.0-1 | 3.7 to 1.7 | WICTKKYPNTISCRRDSDCRVTCICRGNGYCG |
| MCopt1.0-2 | 2.7 to 1.6 | WKCQPTNGYRIRCRRDSDCPGDCICRGNGYCG |
| MCopt1.0-3 | 2.6 to 0.6 | PMCTQRKNRIRLCRRDSDCTGACICRGNGYCG |

| Construct name | Amino acid sequence |
|---|---|
| MC-FN-010 | PMCTQRKNRIRLCRRDSDCTGACICRGNGYCG |
| MC-FN-011 | AMCTQRKNRIRLCRRDSDCTGACICRGNGYCG |
| MC-FN-012 | PACTQRKNRIRLCRRDSDCTGACICRGNGYCG |
| MC-FN-013 | PMCAQRKNRIRLCRRDSDCTGACICRGNGYCG |
| MC-FN-014 | PMCTARKNRIRLCRRDSDCTGACICRGNGYCG |
| MC-FN-015 | PMCTQAKNRIRLCRRDSDCTGACICRGNGYCG |
| MC-FN-016 | PMCTQRANRIRLCRRDSDCTGACICRGNGYCG |
| MC-FN-017 | PMCTQRKARIRLCRRDSDCTGACICRGNGYCG |
| MC-FN-018 | PMCTQRKNAIRLCRRDSDCTGACICRGNGYCG |
| MC-FN-019 | PMCTQRKNRARLCRRDSDCTGACICRGNGYCG |
| MC-FN-0110 | PMCTQRKNRIALCRRDSDCTGACICRGNGYCG |
| MC-FN-0111 | PMCTQRKNRIRACRRDSDCTGACICRGNGYCG |
| MC-FN-0112 | PMCTQRKNRIRLCARDSDCTGACICRGNGYCG |
| MC-FN-0113 | PMCTQRKNRIRLCRADSDCTGACICRGNGYCG |
| MC-FN-0114 | PMCTQRKNRIRLCRRDSDCTGACICAGNGYCG |

B

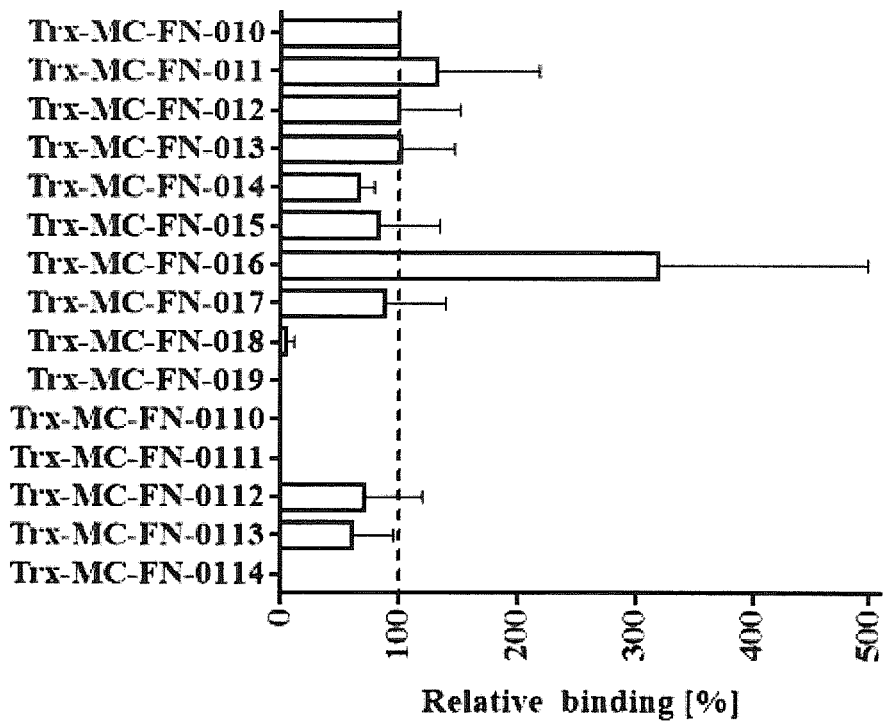

C

A

B

Figure 10

A

| Name | Concentration (nM) | Kon (1/Ms) | Koff (1/s) | KD (μM) |
|---|---|---|---|---|
| MC-FN-010 | 50-4000 | $4.95 \times 10^4$ | 0.07831 | 1.58 |
| MC-FN-016 | 62.5-4000 | $1.33 \times 10^5$ | 0.1873 | 1.41 |

B

| Name | Concentration (nM) | Kon (1/Ms) | Koff (1/s) | KD (pM) |
|---|---|---|---|---|
| AF680-(MC-FN-010)$_3$ | 1.25-10 | $8.04 \times 10^6$ | $3.47 \times 10^{-3}$ | 431 |
| AF680-(MC-FN-016)$_3$ | 1.25-10 | $2.56 \times 10^6$ | $2.31 \times 10^{-3}$ | 902 |
| AF680-(MC-FN-0115)$_3$ | 1.25-10 | No binding to FN-67B89 | | |

A

B (continued)

A

B

A

B

C

Figure 15

| Name | Applied concentration range (nM) | Kon (1/Ms) | Koff (1/s) | KD (nM) |
|---|---|---|---|---|
| DOTA-(MC-FN-016)$_3$ | 1.25-10 | $3.73 \times 10^6$ | $2.26 \times 10^{-3}$ | 0.624 |

SEQUENCE LISTING

```
<160> NUMBER OF SEQ ID NOS: 29

<210> SEQ ID NO 1
<211> LENGTH: 7341
<212> TYPE: DNA
<213> ORGANISM: Homo sapiens

<400> SEQUENCE: 1
atgcttaggg gtccggggcc cgggctgctg ctgctggccg tccagtgcct ggggacagcg      60
gtgccctcca cgggagcctc gaagagcaag aggcaggctc agcaaatggt tcagccccag     120
tccccggtgg ctgtcagtca aagcaagccc ggttgttatg acaatggaaa acactatcag     180
ataaatcaac agtgggagcg gacctaccta ggcaatgcgt tggtttgtac ttgttatgga     240
ggaagccgag gttttaactg cgagagtaaa cctgaagctg aagagacttg ctttgacaag     300
tacactggga acacttaccg agtgggtgac acttatgagc gtcctaaaga ctccatgatc     360
tgggactgta cctgcatcgg ggctgggcga gggagaataa gctgtaccat cgcaaaccgc     420
tgccatgaag ggggtcagtc ctacaagatt ggtgacacct ggaggagacc acatgagact     480
ggtggttaca tgttagagtg tgtgtgtctt ggtaatggaa aaggagaatg gacctgcaag     540
cccatagctg agaagtgttt tgatcatgct gctgggactt cctatgtggt cggagaaacg     600
tgggagaagc cctaccaagg ctggatgatg gtagattgta cttgcctggg agaaggcagc     660
ggacgcatca cttgcacttc tagaaataga tgcaacgatc aggacacaag gacatcctat     720
agaattggag acacctggag caagaaggat aatcgaggaa acctgctcca gtgcatctgc     780
acaggcaacg gccgaggaga gtggaagtgt gagaggcaca cctctgtgca gaccacatcg     840
agcggatctg gcccttcac cgatgttcgt gcagctgttt accaaccgca gcctcacccc     900
```

-continued

```
cagcctcctc cctatggcca ctgtgtcaca gacagtggtg tggtctactc tgtggggatg      960
cagtggctga agacacaagg aaataagcaa atgctttgca cgtgcctggg caacggagtc     1020
agctgccaag agacagctgt aacccagact tacggtggca actcaaatgg agagccatgt     1080
gtcttaccat tcacctacaa tggcaggacg ttctactcct gcaccacaga agggcgacag     1140
gacggacatc tttggtgcag cacaacttcg aattatgagc aggaccagaa atactctttc     1200
tgcacagacc acactgtttt ggttcagact cgaggaggaa attccaatgg tgccttgtgc     1260
cacttcccct tcctatacaa caaccacaat tacactgatt gcacttctga gggcagaaga     1320
gacaacatga agtggtgtgg gaccacacag aactatgatg ccgaccagaa gtttgggttc     1380
tgccccatgg ctgcccacga ggaaatctgc acaaccaatg aaggggtcat gtaccgcatt     1440
ggagatcagt gggataagca gcatgacatg ggtcacatga tgaggtgcac gtgtgttggg     1500
aatggtcgtg gggaatggac atgcattgcc tactcgcagc ttcgagatca gtgcattgtt     1560
gatgacatca cttacaatgt gaacgacaca ttccacaagc gtcatgaaga ggggcacatg     1620
ctgaactgta catgcttcgg tcagggtcgg ggcaggtgga agtgtgatcc cgtcgaccaa     1680
tgccaggatt cagagactgg gacgttttat caaattggag attcatggga agtatgtg      1740 catggtgtca gataccagtg ctactgctat ggccgtggca ttggggagtg gcattgccaa     1800
cctttacaga cctatccaag ctcaagtggt cctgtcgaag tatttatcac tgagactccg     1860
agtcagccca actcccaccc catccagtgg aatgcaccac agccatctca catttccaag     1920
tacattctca ggtggagacc taaaaattct gtaggccgtt ggaaggaagc taccatacca     1980
ggccacttaa actcctacac catcaaaggc ctgaagcctg gtgtggtata cgagggccag     2040
ctcatcagca tccagcagta cggccaccaa gaagtgactc gctttgactt caccaccacc     2100
agcaccagca cacctgtgac cagcaacacc gtgacaggag agacgactcc cttttctcct     2160
cttgtggcca cttctgaatc tgtgaccgaa atcacagcca gtagctttgt ggtctcctgg     2220
gtctcagctt ccgacaccgt gtcgggattc cgggtggaat atgagctgag tgaggaggga     2280
gatgagccac agtacctgga tcttccaagc acagccactt ctgtgaacat ccctgacctg     2340
cttcctggcc gaaaatacat tgtaaatgtc tatcagatat ctgaggatgg ggagcagagt     2400
ttgatcctgt ctacttcaca acaacagcg cctgatgccc ctcctgaccc gactgtggac     2460
caagttgatg acacctcaat tgttgttcgc tggagcagac cccaggctcc catcacaggg     2520
tacagaatag tctattcgcc atcagtagaa ggtagcagca cagaactcaa ccttcctgaa     2580
actgcaaact ccgtcaccct cagtgacttg caacctggtg ttcagtataa catcactatc     2640
tatgctgtgg aagaaaatca agaaagtaca cctgttgtca ttcaacaaga aaccactggc     2700
accccacgct cagatacagt gccctctccc agggacctgc agtttgtgga agtgacagac     2760
gtgaaggtca ccatcatgtg gacaccgcct gagagtgcag tgaccggcta ccgtgtggat     2820
gtgatccccg tcaacctgcc tggcgagcac gggcagaggc tgcccatcag caggaacacc     2880
tttgcagaag tcaccgggct gtcccctggg gtcacctatt acttcaaagt ctttgcagtg     2940
agccatggga gggagagcaa gcctctgact gctcaacaga caaccaaact ggatgctccc     3000
actaacctcc agtttgtcaa tgaaactgat tctactgtcc tggtgagatg gactccacct     3060
cgggcccaga taacaggata ccgactgacc gtgggcctta cccgaagagg acagcccagg     3120
cagtacaatg tgggtccctc tgtctccaag tacccactga ggaatctgca gcctgcatct     3180
gagtacaccg tatccctcgt ggccataaag ggcaaccaag agagcccaa  agccactgga     3240 gtctttacca cactgcagcc tgggagctct attccacctt acaacaccga ggtgactgag     3300
```

```
accaccattg tgatcacatg gacgcctgct ccaagaattg gttttaagct gggtgtacga   3360
ccaagccagg gaggagaggc accacgagaa gtgacttcag actcaggaag catcgttgtg   3420
tccggcttga ctccaggagt agaatacgtc tacaccatcc aagtcctgag agatggacag   3480
gaaagagatg cgccaattgt aaacaaagtg gtgacaccat tgtctccacc aacaaacttg   3540
catctggagg caaaccctga cactggagtg ctcacagtct cctgggagag gagcaccacc   3600
ccagacatta ctggttatag aattaccaca accctacaa acggccagca gggaaattct    3660
ttggaagaag tggtccatgc tgatcagagc tcctgcactt ttgataacct gagtcccggc   3720
ctggagtaca atgtcagtgt ttacactgtc aaggatgaca aggaaagtgt ccctatctct   3780
gataccatca tcccagaggt gccccaactc actgacctaa gctttgttga tataaccgat   3840
tcaagcatcg gcctgaggtg gacccccgcta aactcttcca ccattattgg gtaccgcatc   3900
acagtagttg cggcaggaga aggtatccct attttgaag attttgtgga ctcctcagta    3960
ggatactaca cagtcacagg gctggagccg ggcattgact atgatatcag cgttatcact   4020
ctcattaatg gcggcgagag tgcccctact acactgacac aacaaacggc tgttcctcct   4080
cccactgacc tgcgattcac caacattggt ccagacacca tgcgtgtcac ctgggctcca   4140
cccccatcca ttgatttaac caacttcctg gtgcgttact cacctgtgaa aaatgaggaa   4200
gatgttgcag agttgtcaat ttctccttca gacaatgcag tggtcttaac aaatctcctg   4260
cctggtacag aatatgtagt gagtgtctcc agtgtctacg aacaacatga gagcacacct   4320
cttagaggaa gacagaaaac aggtcttgat tccccaactg gcattgactt ttctgatatt   4380
actgccaact cttttactgt gcactggatt gctcctcgag ccaccatcac tggctacagg   4440
atccgccatc atcccgagca cttcagtggg agacctcgag aagatcgggt gccccactct   4500
cggaattcca tcaccctcac caacctcact ccaggcacag agtatgtggt cagcatcgtt   4560
gctcttaatg gcagagagga aagtccctta ttgattggcc aacaatcaac agtttctgat   4620
gttccgaggg acctggaagt tgttgctgcg acccccacca gcctactgat cagctgggat   4680
gctcctgctg tcacagtgag atattacagg atcacttacg gagagacagg aggaaatagc   4740
cctgtccagg agttcactgt gcctgggagc aagtctacag ctaccatcag cggccttaaa   4800
cctggagttg attataccat cactgtgtat gctgtcactg gccgtggaga cagccccgca   4860
agcagcaagc caatttccat taattaccga acagaaattg acaaaccatc ccagatgcaa   4920
gtgaccgatg ttcaggacaa cagcattagt gtcaagtggc tgccttcaag ttcccctgtt   4980
actggttaca gagtaaccac cactcccaaa aatggaccag accaacaaa  aactaaaact   5040
gcaggtccag atcaaacaga aatgactatt gaaggcttgc agcccacagt ggagtatgtg   5100
gttagtgtct atgctcagaa tccaagcgga gagagtcagc ctctggttca gactgcagta   5160
accaacattg atcgccctaa aggactggca ttcactgatg tggatgtcga ttccatcaaa   5220
attgcttggg aaagcccaca ggggcaagtt tccaggtaca gggtgaccta ctcgagccct   5280
gaggatggaa tccatgagct attccctgca cctgatggtg aagaagacac tgcagagctg   5340
caaggcctca gaccgggttc tgagtacaca gtcagtgtgg ttgccttgca cgatgatatg   5400
gagagccagc cctgattgg aacccagtcc acagctattc ctgcaccaac tgacctgaag   5460
ttcactcagg tcacacccac aagcctgagc gcccagtgga caccaccaa  tgttcagctc   5520
actggatatc gagtgcgggt gacccccaag gagaagaccg gaccaatgaa agaaatcaac   5580
cttgctcctg acagctcatc cgtggttgta tcaggactta tggtggccac caaatatgaa   5640
```

-continued

| | |
|---|---|
| gtgagtgtct atgctcttaa ggacactttg acaagcagac cagctcaggg agttgtcacc | 5700 |
| actctggaga atgtcagccc accaagaagg gctcgtgtga cagatgctac tgagaccacc | 5760 |
| atcaccatta gctggagaac caagactgag acgatcactg gcttccaagt tgatgccgtt | 5820 |
| ccagccaatg gccagactcc aatccagaga accatcaagc cagatgtcag aagctcacac | 5880 |
| atcacaggtt tacaaccagg cactgactac aagatctacc tgtacacctt gaatgacaat | 5940 |
| gctcggagct cccctgtggt catcgacgcc tccactgcca ttgatgcacc atccaacctg | 6000 |
| cgtttcctgg ccaccacacc caattccttg ctggtatcat ggcagccgcc acgtgccagg | 6060 |
| attaccggct acatcatcaa gtatgagaag cctgggtctc ctcccagaga agtggtccct | 6120 |
| cggcccccgcc ctggtgtcac agaggctact attactggct ggaaccggg aaccgaatat | 6180 |
| acaatttatg tcattgccct gaagaataat cagaagagcg agcccctgat tggaaggaaa | 6240 |
| aagacagacg agcttcccca actggtaacc cttccacacc ccaatcttca tggaccagag | 6300 |
| atcttggatg ttccttccac agttcaaaag acccctttcg tcacccaccc tgggtatgac | 6360 |
| actggaaatg gtattcagct tcctggcact tctggtcagc aacccagtgt tgggcaacaa | 6420 |
| atgatctttg aggaacatgg ttttaggcgg accacaccgc ccacaacggc cacccccata | 6480 |
| aggcataggc caagaccata cccgccgaat gtaggacaag aagctctctc tcagacaacc | 6540 |
| atctcatggg ccccattcca ggacacttct gagtacatca tttcatgtca tcctgttggc | 6600 |
| actgatgaag aacccttaca gttcagggtt cctggaactt ctaccagtgc cactctgaca | 6660 |
| ggcctcacca gaggtgccac ctacaacatc atagtggagg cactgaaaga ccagcagagg | 6720 |
| cataaggttc gggaagaggt tgttaccgtg ggcaactctg tcaacgaagg cttgaaccaa | 6780 |
| cctacggatg actcgtgctt tgaccctac acagtttccc attatgccgt tggagatgag | 6840 |
| tgggaacgaa tgtctgaatc aggctttaaa ctgttgtgcc agtgcttagg ctttggaagt | 6900 |
| ggtcatttca gatgtgattc atctagatgg tgccatgaca atggtgtgaa ctacaagatt | 6960 |
| ggagagaagt gggaccgtca gggagaaaat ggccagatga tgagctgcac atgtcttggg | 7020 |
| aacggaaaag gagaattcaa gtgtgaccct catgaggcaa cgtgttatga tgatgggaag | 7080 |
| acataccacg taggagaaca gtggcagaag gaatatctcg gtgccatttg ctcctgcaca | 7140 |
| tgctttggag ccagcggggg ctggcgctgt gacaactgcc gcagacctgg gggtgaaccc | 7200 |
| agtcccgaag gcactactgg ccagtcctac aaccagtatt ctcagagata ccatcagaga | 7260 |
| acaaacacta atgttaattg cccaattgag tgcttcatgc ctttagatgt acaggctgac | 7320 |
| agagaagatt cccgagagta a | 7341 |

<210> SEQ ID NO 2
<211> LENGTH: 2446
<212> TYPE: PRT
<213> ORGANISM: Homo sapiens

<400> SEQUENCE: 2

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly

-continued

```
                65                  70                  75                  80
Gly Ser Arg Gly Phe Asn Cys Glu Ser Lys Pro Glu Ala Glu Thr
                    85                  90                  95
Cys Phe Asp Lys Tyr Thr Gly Asn Thr Tyr Arg Val Gly Asp Thr Tyr
                100                 105                 110
Glu Arg Pro Lys Asp Ser Met Ile Trp Asp Cys Thr Cys Ile Gly Ala
                115                 120                 125
Gly Arg Gly Arg Ile Ser Cys Thr Ile Ala Asn Arg Cys His Glu Gly
    130                 135                 140
Gly Gln Ser Tyr Lys Ile Gly Asp Thr Trp Arg Arg Pro His Glu Thr
145                 150                 155                 160
Gly Gly Tyr Met Leu Glu Cys Val Cys Leu Gly Asn Gly Lys Gly Glu
                    165                 170                 175
Trp Thr Cys Lys Pro Ile Ala Glu Lys Cys Phe Asp His Ala Ala Gly
                180                 185                 190
Thr Ser Tyr Val Val Gly Glu Thr Trp Glu Lys Pro Tyr Gln Gly Trp
            195                 200                 205
Met Met Val Asp Cys Thr Cys Leu Gly Glu Gly Ser Gly Arg Ile Thr
        210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
                260                 265                 270
His Thr Ser Val Gln Thr Thr Ser Ser Gly Ser Gly Pro Phe Thr Asp
            275                 280                 285
Val Arg Ala Ala Val Tyr Gln Pro Gln Pro His Pro Gln Pro Pro
        290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
                340                 345                 350
Gly Asn Ser Asn Gly Glu Pro Cys Val Leu Pro Phe Thr Tyr Asn Gly
            355                 360                 365
Arg Thr Phe Tyr Ser Cys Thr Thr Glu Gly Arg Gln Asp Gly His Leu
        370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
                420                 425                 430
Asp Cys Thr Ser Glu Gly Arg Arg Asp Asn Met Lys Trp Cys Gly Thr
            435                 440                 445
Thr Gln Asn Tyr Asp Ala Asp Gln Lys Phe Gly Phe Cys Pro Met Ala
        450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
```

```
Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
            690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
            770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
            850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910
```

```
Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Glu Val Pro Gln Leu Thr Asp Leu Ser Phe Val Asp Ile
    1265                1270                1275

Thr Asp Ser Ser Ile Gly Leu Arg Trp Thr Pro Leu Asn Ser Ser
    1280                1285                1290

Thr Ile Ile Gly Tyr Arg Ile Thr Val Val Ala Ala Gly Glu Gly
    1295                1300                1305

Ile Pro Ile Phe Glu Asp Phe Val Asp Ser Ser Val Gly Tyr Tyr
```

```
            1310                1315                1320
Thr Val Thr Gly Leu Glu Pro Gly Ile Asp Tyr Asp Ile Ser Val
        1325                1330                1335
Ile Thr Leu Ile Asn Gly Gly Glu Ser Ala Pro Thr Thr Leu Thr
        1340                1345                1350
Gln Gln Thr Ala Val Pro Pro Thr Asp Leu Arg Phe Thr Asn
        1355                1360                1365
Ile Gly Pro Asp Thr Met Arg Val Thr Trp Ala Pro Pro Ser
        1370                1375                1380
Ile Asp Leu Thr Asn Phe Leu Val Arg Tyr Ser Pro Val Lys Asn
        1385                1390                1395
Glu Glu Asp Val Ala Glu Leu Ser Ile Ser Pro Ser Asp Asn Ala
        1400                1405                1410
Val Val Leu Thr Asn Leu Leu Pro Gly Thr Glu Tyr Val Val Ser
        1415                1420                1425
Val Ser Ser Val Tyr Glu Gln His Glu Ser Thr Pro Leu Arg Gly
        1430                1435                1440
Arg Gln Lys Thr Gly Leu Asp Ser Pro Thr Gly Ile Asp Phe Ser
        1445                1450                1455
Asp Ile Thr Ala Asn Ser Phe Thr Val His Trp Ile Ala Pro Arg
        1460                1465                1470
Ala Thr Ile Thr Gly Tyr Arg Ile Arg His His Pro Glu His Phe
        1475                1480                1485
Ser Gly Arg Pro Arg Glu Asp Arg Val Pro His Ser Arg Asn Ser
        1490                1495                1500
Ile Thr Leu Thr Asn Leu Thr Pro Gly Thr Glu Tyr Val Val Ser
        1505                1510                1515
Ile Val Ala Leu Asn Gly Arg Glu Glu Ser Pro Leu Leu Ile Gly
        1520                1525                1530
Gln Gln Ser Thr Val Ser Asp Val Pro Arg Asp Leu Glu Val Val
        1535                1540                1545
Ala Ala Thr Pro Thr Ser Leu Leu Ile Ser Trp Asp Ala Pro Ala
        1550                1555                1560
Val Thr Val Arg Tyr Tyr Arg Ile Thr Tyr Gly Glu Thr Gly Gly
        1565                1570                1575
Asn Ser Pro Val Gln Glu Phe Thr Val Pro Gly Ser Lys Ser Thr
        1580                1585                1590
Ala Thr Ile Ser Gly Leu Lys Pro Gly Val Asp Tyr Thr Ile Thr
        1595                1600                1605
Val Tyr Ala Val Thr Gly Arg Gly Asp Ser Pro Ala Ser Ser Lys
        1610                1615                1620
Pro Ile Ser Ile Asn Tyr Arg Thr Glu Ile Asp Lys Pro Ser Gln
        1625                1630                1635
Met Gln Val Thr Asp Val Gln Asp Asn Ser Ile Ser Val Lys Trp
        1640                1645                1650
Leu Pro Ser Ser Ser Pro Val Thr Gly Tyr Arg Val Thr Thr Thr
        1655                1660                1665
Pro Lys Asn Gly Pro Gly Pro Thr Lys Thr Lys Thr Ala Gly Pro
        1670                1675                1680
Asp Gln Thr Glu Met Thr Ile Glu Gly Leu Gln Pro Thr Val Glu
        1685                1690                1695
Tyr Val Val Ser Val Tyr Ala Gln Asn Pro Ser Gly Glu Ser Gln
        1700                1705                1710
```

```
Pro Leu Val Gln Thr Ala Val Thr Asn Ile Asp Arg Pro Lys Gly
    1715            1720                1725

Leu Ala Phe Thr Asp Val Asp Val Asp Ser Ile Lys Ile Ala Trp
    1730            1735                1740

Glu Ser Pro Gln Gly Gln Val Ser Arg Tyr Arg Val Thr Tyr Ser
    1745            1750                1755

Ser Pro Glu Asp Gly Ile His Glu Leu Phe Pro Ala Pro Asp Gly
    1760            1765                1770

Glu Glu Asp Thr Ala Glu Leu Gln Gly Leu Arg Pro Gly Ser Glu
    1775            1780                1785

Tyr Thr Val Ser Val Val Ala Leu His Asp Asp Met Glu Ser Gln
    1790            1795                1800

Pro Leu Ile Gly Thr Gln Ser Thr Ala Ile Pro Ala Pro Thr Asp
    1805            1810                1815

Leu Lys Phe Thr Gln Val Thr Pro Thr Ser Leu Ser Ala Gln Trp
    1820            1825                1830

Thr Pro Pro Asn Val Gln Leu Thr Gly Tyr Arg Val Arg Val Thr
    1835            1840                1845

Pro Lys Glu Lys Thr Gly Pro Met Lys Glu Ile Asn Leu Ala Pro
    1850            1855                1860

Asp Ser Ser Ser Val Val Val Ser Gly Leu Met Val Ala Thr Lys
    1865            1870                1875

Tyr Glu Val Ser Val Tyr Ala Leu Lys Asp Thr Leu Thr Ser Arg
    1880            1885                1890

Pro Ala Gln Gly Val Val Thr Thr Leu Glu Asn Val Ser Pro Pro
    1895            1900                1905

Arg Arg Ala Arg Val Thr Asp Ala Thr Glu Thr Thr Ile Thr Ile
    1910            1915                1920

Ser Trp Arg Thr Lys Thr Glu Thr Ile Thr Gly Phe Gln Val Asp
    1925            1930                1935

Ala Val Pro Ala Asn Gly Gln Thr Pro Ile Gln Arg Thr Ile Lys
    1940            1945                1950

Pro Asp Val Arg Ser Tyr Thr Ile Thr Gly Leu Gln Pro Gly Thr
    1955            1960                1965

Asp Tyr Lys Ile Tyr Leu Tyr Thr Leu Asn Asp Asn Ala Arg Ser
    1970            1975                1980

Ser Pro Val Val Ile Asp Ala Ser Thr Ala Ile Asp Ala Pro Ser
    1985            1990                1995

Asn Leu Arg Phe Leu Ala Thr Thr Pro Asn Ser Leu Leu Val Ser
    2000            2005                2010

Trp Gln Pro Pro Arg Ala Arg Ile Thr Gly Tyr Ile Ile Lys Tyr
    2015            2020                2025

Glu Lys Pro Gly Ser Pro Pro Arg Glu Val Val Pro Arg Pro Arg
    2030            2035                2040

Pro Gly Val Thr Glu Ala Thr Ile Thr Gly Leu Glu Pro Gly Thr
    2045            2050                2055

Glu Tyr Thr Ile Tyr Val Ile Ala Leu Lys Asn Asn Gln Lys Ser
    2060            2065                2070

Glu Pro Leu Ile Gly Arg Lys Lys Thr Asp Glu Leu Pro Gln Leu
    2075            2080                2085

Val Thr Leu Pro His Pro Asn Leu His Gly Pro Glu Ile Leu Asp
    2090            2095                2100
```

```
Val Pro Ser Thr Val Gln Lys Thr Pro Phe Val Thr His Pro Gly
    2105                2110                2115

Tyr Asp Thr Gly Asn Gly Ile Gln Leu Pro Gly Thr Ser Gly Gln
    2120                2125                2130

Gln Pro Ser Val Gly Gln Gln Met Ile Phe Glu Glu His Gly Phe
    2135                2140                2145

Arg Arg Thr Thr Pro Pro Thr Thr Ala Thr Pro Ile Arg His Arg
    2150                2155                2160

Pro Arg Pro Tyr Pro Pro Asn Val Gly Gln Glu Ala Leu Ser Gln
    2165                2170                2175

Thr Thr Ile Ser Trp Ala Pro Phe Gln Asp Thr Ser Glu Tyr Ile
    2180                2185                2190

Ile Ser Cys His Pro Val Gly Thr Asp Glu Glu Pro Leu Gln Phe
    2195                2200                2205

Arg Val Pro Gly Thr Ser Thr Ser Ala Thr Leu Thr Gly Leu Thr
    2210                2215                2220

Arg Gly Ala Thr Tyr Asn Ile Ile Val Glu Ala Leu Lys Asp Gln
    2225                2230                2235

Gln Arg His Lys Val Arg Glu Glu Val Val Thr Val Gly Asn Ser
    2240                2245                2250

Val Asn Glu Gly Leu Asn Gln Pro Thr Asp Asp Ser Cys Phe Asp
    2255                2260                2265

Pro Tyr Thr Val Ser His Tyr Ala Val Gly Asp Glu Trp Glu Arg
    2270                2275                2280

Met Ser Glu Ser Gly Phe Lys Leu Leu Cys Gln Cys Leu Gly Phe
    2285                2290                2295

Gly Ser Gly His Phe Arg Cys Asp Ser Ser Arg Trp Cys His Asp
    2300                2305                2310

Asn Gly Val Asn Tyr Lys Ile Gly Glu Lys Trp Asp Arg Gln Gly
    2315                2320                2325

Glu Asn Gly Gln Met Met Ser Cys Thr Cys Leu Gly Asn Gly Lys
    2330                2335                2340

Gly Glu Phe Lys Cys Asp Pro His Glu Ala Thr Cys Tyr Asp Asp
    2345                2350                2355

Gly Lys Thr Tyr His Val Gly Glu Gln Trp Gln Lys Glu Tyr Leu
    2360                2365                2370

Gly Ala Ile Cys Ser Cys Thr Cys Phe Gly Gly Gln Arg Gly Trp
    2375                2380                2385

Arg Cys Asp Asn Cys Arg Arg Pro Gly Gly Glu Pro Ser Pro Glu
    2390                2395                2400

Gly Thr Thr Gly Gln Ser Tyr Asn Gln Tyr Ser Gln Arg Tyr His
    2405                2410                2415

Gln Arg Thr Asn Thr Asn Val Asn Cys Pro Ile Glu Cys Phe Met
    2420                2425                2430

Pro Leu Asp Val Gln Ala Asp Arg Glu Asp Ser Arg Glu
    2435                2440                2445

<210> SEQ ID NO 3
<211> LENGTH: 4
<212> TYPE: PRT
<213> ORGANISM: Artificial Sequence
<220> FEATURE:
<223> OTHER INFORMATION: EDB binding peptide
<220> FEATURE:
<221> NAME/KEY: MISC_FEATURE
<222> LOCATION: (2)..(2)
```

<223> OTHER INFORMATION: Ile or Val

<400> SEQUENCE: 3

Arg Xaa Arg Leu
1

<210> SEQ ID NO 4
<211> LENGTH: 17
<212> TYPE: PRT
<213> ORGANISM: Artificial Sequence
<220> FEATURE:
<223> OTHER INFORMATION: EDB binding peptide
<220> FEATURE:
<221> NAME/KEY: MISC_FEATURE
<222> LOCATION: (1)..(1)
<223> OTHER INFORMATION: Independently from each other any amino acid
<220> FEATURE:
<221> NAME/KEY: REPEAT
<222> LOCATION: (1)..(1)
<223> OTHER INFORMATION: Preferably repeated 0 to 4, preferably 1 or 2
     times
<220> FEATURE:
<221> NAME/KEY: MISC_FEATURE
<222> LOCATION: (3)..(3)
<223> OTHER INFORMATION: Independently from each other any amino acid
<220> FEATURE:
<221> NAME/KEY: REPEAT
<222> LOCATION: (3)..(3)
<223> OTHER INFORMATION: Preferably repeated 3 to 10, preferably 4, 5, 6
     or 7 times
<220> FEATURE:
<221> NAME/KEY: MISC_FEATURE
<222> LOCATION: (5)..(5)
<223> OTHER INFORMATION: Ile or Val
<220> FEATURE:
<221> NAME/KEY: MISC_FEATURE
<222> LOCATION: (7)..(7)
<223> OTHER INFORMATION: Independently from each other any amino acid
<220> FEATURE:
<221> NAME/KEY: REPEAT
<222> LOCATION: (7)..(7)
<223> OTHER INFORMATION: Preferably repeated 0 to 4, preferably 0 or 1
     times
<220> FEATURE:
<221> NAME/KEY: MISC_FEATURE
<222> LOCATION: (9)..(9)
<223> OTHER INFORMATION: Independently from each other any amino acid
<220> FEATURE:
<221> NAME/KEY: REPEAT
<222> LOCATION: (9)..(9)
<223> OTHER INFORMATION: Preferably repeated 3 to 7, preferably 4, 5 or
     6 times
<220> FEATURE:
<221> NAME/KEY: MISC_FEATURE
<222> LOCATION: (11)..(11)
<223> OTHER INFORMATION: Independently from each other any amino acid
<220> FEATURE:
<221> NAME/KEY: REPEAT
<222> LOCATION: (11)..(11)
<223> OTHER INFORMATION: Preferably repeated 2 to 6, preferably 2, 3 or
     4 times
<220> FEATURE:
<221> NAME/KEY: MISC_FEATURE
<222> LOCATION: (13)..(13)
<223> OTHER INFORMATION: Independently from each other any amino acid
<220> FEATURE:
<221> NAME/KEY: REPEAT
<222> LOCATION: (13)..(13)
<223> OTHER INFORMATION: Preferably repeated 1 to 3, preferably 1 or 2
     times
<220> FEATURE:
<221> NAME/KEY: MISC_FEATURE
<222> LOCATION: (15)..(15)
<223> OTHER INFORMATION: Independently from each other any amino acid
<220> FEATURE:
<221> NAME/KEY: REPEAT
<222> LOCATION: (15)..(15)

```
<223> OTHER INFORMATION: Preferably repeated 3 to 7, preferably 4, 5 or
      6 times
<220> FEATURE:
<221> NAME/KEY: MISC_FEATURE
<222> LOCATION: (17)..(17)
<223> OTHER INFORMATION: Independently from each other any amino acid
<220> FEATURE:
<221> NAME/KEY: REPEAT
<222> LOCATION: (17)..(17)
<223> OTHER INFORMATION: Preferably repeated 0 to 4, preferably 1 or 2
      times

<400> SEQUENCE: 4

Xaa Cys Xaa Arg Xaa Arg Xaa Cys Xaa Cys Xaa Cys Xaa Cys Xaa Cys
1               5                   10                  15

Xaa

<210> SEQ ID NO 5
<211> LENGTH: 25
<212> TYPE: PRT
<213> ORGANISM: Artificial Sequence
<220> FEATURE:
<223> OTHER INFORMATION: EDB binding peptide
<220> FEATURE:
<221> NAME/KEY: MISC_FEATURE
<222> LOCATION: (1)..(1)
<223> OTHER INFORMATION: Independently from each other any amino acid
<220> FEATURE:
<221> NAME/KEY: REPEAT
<222> LOCATION: (1)..(1)
<223> OTHER INFORMATION: Preferably repeated 0 to 4, preferably 1 or 2
      times
<220> FEATURE:
<221> NAME/KEY: MISC_FEATURE
<222> LOCATION: (3)..(3)
<223> OTHER INFORMATION: Independently from each other any amino acid
<220> FEATURE:
<221> NAME/KEY: REPEAT
<222> LOCATION: (3)..(3)
<223> OTHER INFORMATION: Preferably repeated 3 to 10, preferably 4, 5, 6
      or 7 times
<220> FEATURE:
<221> NAME/KEY: MISC_FEATURE
<222> LOCATION: (5)..(5)
<223> OTHER INFORMATION: Ile or Val
<220> FEATURE:
<221> NAME/KEY: MISC_FEATURE
<222> LOCATION: (7)..(7)
<223> OTHER INFORMATION: Independently from each other any amino acid
<220> FEATURE:
<221> NAME/KEY: REPEAT
<222> LOCATION: (7)..(7)
<223> OTHER INFORMATION: Preferably repeated 0 to 4, preferably 0 or 1
      times
<220> FEATURE:
<221> NAME/KEY: MISC_FEATURE
<222> LOCATION: (15)..(15)
<223> OTHER INFORMATION: Independently from each other any amino acid
<220> FEATURE:
<221> NAME/KEY: REPEAT
<222> LOCATION: (15)..(15)
<223> OTHER INFORMATION: Preferably repeated 2 to 6, preferably 2, 3 or
      4 times
<220> FEATURE:
<221> NAME/KEY: MISC_FEATURE
<222> LOCATION: (25)..(25)
<223> OTHER INFORMATION: Independently from each other any amino acid
<220> FEATURE:
<221> NAME/KEY: REPEAT
<222> LOCATION: (25)..(25)
<223> OTHER INFORMATION: Preferably repeated 0 to 4, preferably 1 or 2
      times

<400> SEQUENCE: 5

Xaa Cys Xaa Arg Xaa Arg Xaa Cys Arg Arg Asp Ser Asp Cys Xaa Cys
```

```
1               5                   10                  15

Ile Cys Arg Gly Asn Gly Tyr Cys Xaa
            20                  25

<210> SEQ ID NO 6
<211> LENGTH: 25
<212> TYPE: PRT
<213> ORGANISM: Artificial Sequence
<220> FEATURE:
<223> OTHER INFORMATION: EDB binding peptide
<220> FEATURE:
<221> NAME/KEY: MISC_FEATURE
<222> LOCATION: (1)..(1)
<223> OTHER INFORMATION: Independently from each other any amino acid
<220> FEATURE:
<221> NAME/KEY: REPEAT
<222> LOCATION: (1)..(1)
<223> OTHER INFORMATION: Preferably repeated 0 to 4, preferably 1 or 2
      times
<220> FEATURE:
<221> NAME/KEY: MISC_FEATURE
<222> LOCATION: (3)..(3)
<223> OTHER INFORMATION: Independently from each other any amino acid
<220> FEATURE:
<221> NAME/KEY: REPEAT
<222> LOCATION: (3)..(3)
<223> OTHER INFORMATION: Preferably repeated 3 to 10, preferably 4, 5, 6
      or 7 times
<220> FEATURE:
<221> NAME/KEY: MISC_FEATURE
<222> LOCATION: (5)..(5)
<223> OTHER INFORMATION: Ile or Val
<220> FEATURE:
<221> NAME/KEY: MISC_FEATURE
<222> LOCATION: (7)..(7)
<223> OTHER INFORMATION: Independently from each other any amino acid
<220> FEATURE:
<221> NAME/KEY: REPEAT
<222> LOCATION: (7)..(7)
<223> OTHER INFORMATION: Preferably repeated 0 to 4, preferably 0 or 1
      times
<220> FEATURE:
<221> NAME/KEY: MISC_FEATURE
<222> LOCATION: (15)..(15)
<223> OTHER INFORMATION: Independently from each other any amino acid
<220> FEATURE:
<221> NAME/KEY: REPEAT
<222> LOCATION: (15)..(15)
<223> OTHER INFORMATION: Preferably repeated 2 to 6, preferably 2, 3 or
      4 times

<400> SEQUENCE: 6

Xaa Cys Xaa Arg Xaa Arg Xaa Cys Arg Arg Asp Ser Asp Cys Xaa Cys
1               5                   10                  15

Ile Cys Arg Gly Asn Gly Tyr Cys Gly
            20                  25

<210> SEQ ID NO 7
<211> LENGTH: 32
<212> TYPE: PRT
<213> ORGANISM: Artificial Sequence
<220> FEATURE:
<223> OTHER INFORMATION: EDB binding peptide

<400> SEQUENCE: 7

Trp Lys Cys Gln Pro Thr Asn Gly Tyr Arg Ile Arg Cys Arg Arg Asp
1               5                   10                  15

Ser Asp Cys Pro Gly Asp Cys Ile Cys Arg Gly Asn Gly Tyr Cys Gly
            20                  25                  30

<210> SEQ ID NO 8
```

-continued

```
<211> LENGTH: 33
<212> TYPE: PRT
<213> ORGANISM: Artificial Sequence
<220> FEATURE:
<223> OTHER INFORMATION: EDB binding peptide

<400> SEQUENCE: 8

Ser Val Cys Lys Asn Val Ser Ile Met Arg Ile Arg Leu Cys Arg Arg
1               5                   10                  15

Asp Ser Asp Cys Pro Gly Ala Cys Ile Cys Arg Gly Asn Gly Tyr Cys
            20                  25                  30

Gly

<210> SEQ ID NO 9
<211> LENGTH: 33
<212> TYPE: PRT
<213> ORGANISM: Artificial Sequence
<220> FEATURE:
<223> OTHER INFORMATION: EDB binding peptide

<400> SEQUENCE: 9

Ser Val Cys Ala His Tyr Asn Thr Ile Arg Val Arg Leu Cys Arg Arg
1               5                   10                  15

Asp Ser Asp Cys Pro Gly Ala Cys Ile Cys Arg Gly Asn Gly Tyr Cys
            20                  25                  30

Gly

<210> SEQ ID NO 10
<211> LENGTH: 32
<212> TYPE: PRT
<213> ORGANISM: Artificial Sequence
<220> FEATURE:
<223> OTHER INFORMATION: EDB binding peptide

<400> SEQUENCE: 10

Trp Thr Cys Thr Lys Lys Tyr Pro Asn Thr Ile Ser Cys Arg Arg Asp
1               5                   10                  15

Ser Asp Cys Arg Val Thr Cys Ile Cys Arg Gly Asn Gly Tyr Cys Gly
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: EDB binding peptide

<400> SEQUENCE: 11

Pro Met Cys Thr Gln Arg Lys Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 12
<211> LENGTH: 33
<212> TYPE: PRT
<213> ORGANISM: Artificial Sequence
<220> FEATURE:
<223> OTHER INFORMATION: EDB binding peptide

<400> SEQUENCE: 12

Ser Val Cys Lys Gln Ala Asn Phe Val Arg Ile Arg Leu Cys Arg Arg
1               5                   10                  15
```

```
Asp Ser Asp Cys Pro Gly Ala Cys Ile Cys Arg Gly Asn Gly Tyr Cys
            20                  25                  30

Gly

<210> SEQ ID NO 13
<211> LENGTH: 32
<212> TYPE: PRT
<213> ORGANISM: Artificial Sequence
<220> FEATURE:
<223> OTHER INFORMATION: EDB binding peptide

<400> SEQUENCE: 13

Ala Met Cys Thr Gln Arg Lys Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: EDB binding peptide

<400> SEQUENCE: 14

Pro Ala Cys Thr Gln Arg Lys Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: EDB binding peptide

<400> SEQUENCE: 15

Pro Met Cys Ala Gln Arg Lys Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: EDB binding peptide

<400> SEQUENCE: 16

Pro Met Cys Thr Ala Arg Lys Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: EDB binding peptide

<400> SEQUENCE: 17
```

```
Pro Met Cys Thr Gln Ala Lys Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30
```

<210> SEQ ID NO 18
<211> LENGTH: 32
<212> TYPE: PRT
<213> ORGANISM: Artificial Sequence
<220> FEATURE:
<223> OTHER INFORMATION: EDB binding peptide

<400> SEQUENCE: 18

```
Pro Met Cys Thr Gln Arg Ala Asn Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30
```

<210> SEQ ID NO 19
<211> LENGTH: 32
<212> TYPE: PRT
<213> ORGANISM: Artificial Sequence
<220> FEATURE:
<223> OTHER INFORMATION: EDB binding peptide

<400> SEQUENCE: 19

```
Pro Met Cys Thr Gln Arg Lys Ala Arg Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30
```

<210> SEQ ID NO 20
<211> LENGTH: 32
<212> TYPE: PRT
<213> ORGANISM: Artificial Sequence
<220> FEATURE:
<223> OTHER INFORMATION: EDB binding peptide

<400> SEQUENCE: 20

```
Pro Met Cys Thr Gln Arg Lys Asn Ala Ile Arg Leu Cys Arg Arg Asp
1               5                   10                  15

Ser Asp Cys Thr Gly Ala Cys Ile Cys Arg Gly Asn Gly Tyr Cys Gly
            20                  25                  30
```

<210> SEQ ID NO 21
<211> LENGTH: 32
<212> TYPE: PRT
<213> ORGANISM: Artificial Sequence
<220> FEATURE:
<223> OTHER INFORMATION: EDB binding peptide

<400> SEQUENCE: 21

```
Pro Met Cys Thr Gln Arg Lys Asn Arg Ala Arg Leu Cys Arg Arg Asp
1               5                   10                  15

Ser Asp Cys Thr Gly Ala Cys Ile Cys Arg Gly Asn Gly Tyr Cys Gly
            20                  25                  30
```

<210> SEQ ID NO 22
<211> LENGTH: 32
<212> TYPE: PRT
<213> ORGANISM: Artificial Sequence
<220> FEATURE:
<223> OTHER INFORMATION: EDB binding peptide

<400> SEQUENCE: 22

```
Pro Met Cys Thr Gln Arg Lys Asn Arg Ile Ala Leu Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: EDB binding peptide

<400> SEQUENCE: 23

Pro Met Cys Thr Gln Arg Lys Asn Arg Ile Arg Ala Cys Arg Arg Asp
1               5                   10                  15

Ser Asp Cys Thr Gly Ala Cys Ile Cys Arg Gly Asn Gly Tyr Cys Gly
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: EDB binding peptide

<400> SEQUENCE: 24

Pro Met Cys Thr Gln Arg Lys Asn Arg Ile Arg Leu Cys Ala Arg Asp
1               5                   10                  15

Ser Asp Cys Thr Gly Ala Cys Ile Cys Arg Gly Asn Gly Tyr Cys Gly
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: EDB binding peptide

<400> SEQUENCE: 25

Pro Met Cys Thr Gln Arg Lys Asn Arg Ile Arg Leu Cys Arg Ala Asp
1               5                   10                  15

Ser Asp Cys Thr Gly Ala Cys Ile Cys Arg Gly Asn Gly Tyr Cys Gly
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: EDB binding peptide

<400> SEQUENCE: 26

Pro Met Cys Thr Gln Arg Lys Asn Arg Ile Arg Leu Cys Arg Arg Asp
1               5                   10                  15

Ser Asp Cys Thr Gly Ala Cys Ile Cys Ala Gly Asn Gly Tyr Cys Gly
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Control peptide
```

```
<400> SEQUENCE: 27

Pro Met Cys Thr Gln Arg Ala Asn Arg Ile Ala Ala Cys Arg Arg Asp
1               5                   10                  15

Ser Asp Cys Thr Gly Ala Cys Ile Cys Arg Gly Asn Gly Tyr Cys Gly
                20                  25                  30

<210> SEQ ID NO 28
<211> LENGTH: 91
<212> TYPE: PRT
<213> ORGANISM: Homo sapiens

<400> SEQUENCE: 28

Glu Val Pro Gln Leu Thr Asp Leu Ser Phe Val Asp Ile Thr Asp Ser
1               5                   10                  15

Ser Ile Gly Leu Arg Trp Thr Pro Leu Asn Ser Ser Thr Ile Ile Gly
                20                  25                  30

Tyr Arg Ile Thr Val Val Ala Ala Gly Glu Gly Ile Pro Ile Phe Glu
            35                  40                  45

Asp Phe Val Asp Ser Ser Val Gly Tyr Tyr Thr Val Thr Gly Leu Glu
        50                  55                  60

Pro Gly Ile Asp Tyr Asp Ile Ser Val Ile Thr Leu Ile Asn Gly Gly
65                  70                  75                  80

Glu Ser Ala Pro Thr Thr Leu Thr Gln Gln Thr
                85                  90

<210> SEQ ID NO 29
<211> LENGTH: 34
<212> TYPE: PRT
<213> ORGANISM: artificial
<220> FEATURE:
<223> OTHER INFORMATION: Trx-MC-Myc-010

<400> SEQUENCE: 29

Met Gly Val Cys Glu Gln Lys Leu Ile Ser Glu Glu Asp Leu Cys Arg
1               5                   10                  15

Arg Asp Ser Asp Cys Pro Gly Ala Cys Ile Cys Arg Gly Asn Gly Tyr
                20                  25                  30

Cys Gly
```

COMPOSITIONS AND METHODS FOR DIAGNOSIS AND TREATMENT OF CANCER

CROSS REFERENCE TO RELATED APPLICATIONS

This application is the US national phase under 35 U.S.C. § 371 of International Application No. PCT/EP2019/064872, filed on Jun. 6, 2019, which claims the benefit of International Application No. PCT/EP2018/065205, filed on Jun. 8, 2018, the contents of which are incorporated herein by reference in their entirety.

TECHNICAL FIELD OF THE INVENTION

The present invention relates to the diagnosis and treatment of diseases expressing Fibronectin Extra Domain B (EDB) such as diseases characterized by tissue remodeling and/or angiogenesis, in particular cancerous diseases, such as head and neck, brain, colorectal, lung, prostate and breast cancer. More particularly, the invention concerns peptides targeting Fibronectin Extra Domain B.

BACKGROUND OF THE INVENTION

Cancer is one of the leading causes of death worldwide, surpassing heart disease. 8.2 million people of the global population died from cancer in 2012 (WHO). Classical anti-cancer therapies for example, radiotherapy, chemotherapy and conventional surgical procedures, often suffer from poor selectivity and, thus, from severe toxic side effects to healthy tissue. Novel forms of treatment consist in the targeted delivery of bioactive molecules (drugs, cytokines, radionuclides, etc.) to the tumor environment by means of binding molecules specific to tumor-associated antigens. This will allow the selective direction of drugs towards target-positive tumor tissue and effectively kill malignant cells without harming healthy cells. This goes along with the development of so-called companion diagnostics enabling the determination of target-positive tumors within a patient in order to in advance guarantee a rationally tailored strategy for individual cancer therapy. In this, the application of target specific imaging techniques has become an important diagnostic step revealing an impressive advancement during the last decades. Imaging techniques can provide critical information about presence and quantity of tumor-associated proteins, localization, early detection, distribution, patient stratification, and treatment monitoring. Tumor imaging represents a fundamental process for the diagnosis of cancer and the monitoring of therapeutic success in cancer treatment. Long established techniques, such as computed tomography scan or magnetic resonance imaging, have been routinely used over decades. However, targeted molecular imaging gains more attention as it precisely visualizes tumors using molecular agents directed against cancer-associated proteins. Biomarkers emerging during tumor angiogenesis are thereby very helpful, because they are usually expressed at high levels in the blood vessels and hence are easily accessible from the bloodstream.

Fibronectin (FN) is a dimeric disulfide-bonded glycoprotein of the extracellular matrix, consisting of type I, type II and type III domains. The protein contributes to many physiological processes, including cell adhesion, migration, differentiation and hemostasis. FN is expressed as multiple alternatively spliced variants derived from a primary transcript. The isoform extra domain B (EDB) comprises an additional type III domain of 91 amino acids, which is specifically inserted between FN domains 7 and 8. This highly conserved Fibronectin Extra Domain B sequence occurs identically in mice, rats, rabbits and human. Fibronectin Extra Domain B is usually absent in normal adult tissues, but involved in tissue remodeling and angiogenesis. In addition, Fibronectin Extra Domain B has been found in many different cancer types with abundant expression pattern in the neovasculature of several aggressive solid human tumors such as head and neck, brain and breast.

For targeting of poorly vascularized tumors, the large size of antibodies and even their fragments might slow the rate of tissue penetration and by this hamper efficient delivery. Moreover, because of the extended blood circulation of antibodies they seem not optimal for diagnostic use especially in the context of imaging concepts. In addition to the foresaid, the molecular architecture of antibodies, with complex glycosylation pattern and disulfide bridges, requires complex cost-intensive manufacturing and complicates further functionalization e.g. by means of an imaging tracer. To overcome these limitations, as an alternative to antibodies so-called protein scaffolds have emerged during the last decades: Scaffolds provide a robust structural framework to precisely engineer interaction molecules tailored for the tight and specific recognition of a given target. Most of them fold properly under non-reducing conditions and can be expressed in bacteria without the need for denaturation and refolding. Even chemical synthesis is an option for the production of some of the formats. Finally, they are well-suited for further functionalization (labelling, oligomerization, fusion with other peptides, etc.) to generate multifunctional binding molecules. Among the different scaffold-based approaches cystine-knot miniproteins ("knottins") have shown great potential for the development of targeted diagnostics and therapeutics agents. Miniproteins are small, 30-50 amino acid polypeptides containing three disulfide bonds that form the eponymous knotted structure. The pseudoknot cystine topology is responsible for an extraordinary thermal, proteolytic and chemical stability, which is desirable for in vivo biomedical applications. For example, without losing structural and functional integrity, miniproteins can be boiled in alkaline or acidic environment. The disulfide-constrained loop regions tolerate broad sequence diversity, providing a robust molecular framework for engineering proteins that recognize a variety of biomedical targets.

There is a need in the art for Fibronectin Extra Domain B binding molecules which are useful in diagnostic and therapeutic approaches.

Fibronectin Extra Domain B binding agents such as Fibronectin Extra Domain B binding peptides are described herein which show high specificity and selectivity for human Fibronectin Extra Domain B. The Fibronectin Extra Domain B binding agents described herein are excellent tools for diagnostic applications, particularly for tumor imaging, and therapeutic applications by efficient targeting of the tumor environment.

DESCRIPTION OF INVENTION

Summary of the Invention

According to the invention, an open-chain variant of the knottin-type trypsin inhibitor II from *Momordica cochinchinensis* (oMCoTI-II) was used as a molecular scaffold for engineering a Fibronectin Extra Domain B (EDB) specific binding protein. To this end, a phage library based on trypsin inhibitor II from *Momordica cochinchinensis* (oMCoTI-II)

was used to select cystine-knot miniproteins against recombinant Fibronectin Extra Domain B. Engineered cystine-knot miniproteins, MC-FN-010 and a derivate MC-FN-016, feature high Fibronectin Extra Domain B specificity as well as reasonable affinities. Chemical oligomerization of the ligands and site-directed fluorescence dye conjugation increased the binding strength enormously while retaining its high specificity and allowed in vivo imaging in a U-87 MG based xenograft glioblastoma mouse model. Both Fibronectin Extra Domain B-binding molecules showed strong accumulation in the tumor and low background signals except for the kidneys. Our results demonstrate the high potential of cystine-knot miniproteins as molecular scaffolds for tumor imaging technologies.

The present invention generally provides compounds useful for the treatment and/or diagnosis of diseases expressing Fibronectin Extra Domain B such as cancer diseases. These compounds provide for the selective detection of cells expressing Fibronectin Extra Domain B and/or eradication of cells expressing Fibronectin Extra Domain B and/or of cells that are associated with an environment, wherein Fibronectin Extra Domain B is expressed such as cells that are associated with cells expressing Fibronectin Extra Domain B. The present invention allows to minimize adverse effects to normal cells not expressing Fibronectin Extra Domain B and/or not being associated with an environment, wherein Fibronectin Extra Domain B is expressed.

The present invention provides a Fibronectin Extra Domain B (EDB) binding peptide which comprises the amino acid sequence motif Arg-Ile/Val-Arg.

In one embodiment, the Fibronectin Extra Domain B binding peptide comprises the amino acid sequence motif Arg-Ile/Val-Arg-Leu.

In one embodiment, the Fibronectin Extra Domain B binding peptide comprises the amino acid sequence:
(Xaa)n1 Cys (Xaa)n2 Arg Ile/Val Arg (Xaa)n3 Cys (Xaa)n4 Cys (Xaa)n5 Cys (Xaa)n6 Cys (Xaa)n7 Cys (Xaa)n8 (SEQ ID NO: 4)
wherein
the Cys residues form a cystine knot structure,
Xaa is independently from each other any amino acid and n1, n2, n3, n4, n5, n6, n7, and n8 are the respective numbers of amino acids,
wherein the nature of the amino acids Xaa and/or the number of amino acids n1, n2, n3, n4, n5, n6, n7 and n8 are such that a cystine knot structure can form between the Cys residues.

In one embodiment of the Fibronectin Extra Domain B binding peptide:
n1 is 0 to 4, preferably 1 or 2,
n2 is 3 to 10, preferably 4, 5, 6 or 7,
n3 is 0 to 4, preferably 0 or 1,
n4 is 3 to 7, preferably 4, 5 or 6,
n5 is 2 to 6, preferably 2, 3 or 4,
n6 is 1 to 3, preferably 1 or 2,
n7 is 3 to 7, preferably 4, 5 or 6, and
n8 is 0 to 4, preferably 1 or 2.

In one embodiment of the Fibronectin Extra Domain B binding peptide (Xaa)n3 is Leu or is missing, preferably (Xaa)n3 is Leu. In one embodiment of the Fibronectin Extra Domain B binding peptide (Xaa)n2 is (Xaa)n2' Asn, wherein preferably n2' is 2 to 9, preferably 3, 4, 5 or 6. In one embodiment of the Fibronectin Extra Domain B binding peptide (Xaa)n7 is Arg (Xaa)n7', wherein preferably n7' is 2 to 6, preferably 3, 4 or 5.

In one embodiment of the Fibronectin Extra Domain B binding peptide:
n2 is 5 or 6 or n2' is 4 or 5,
n3 is 0 or 1,
n4 is 5,
n5 is 3,
n6 is 1, and
n7 is 5 or n7' is 4.

In one embodiment, the Fibronectin Extra Domain B binding peptide comprises the amino acid sequence:
(Xaa)n1 Cys (Xaa)n2 Arg Ile/Val Arg (Xaa)n3 Cys Arg Arg Asp Ser Asp Cys (Xaa)n5 Cys Ile Cys Arg Gly Asn Gly Tyr Cys (Xaa)n8 (SEQ ID NO: 5)

In one embodiment, the Fibronectin Extra Domain B binding peptide comprises the amino acid sequence:
(Xaa)n1 Cys (Xaa)n2 Arg Ile/Val Arg (Xaa)n3 Cys Arg Arg Asp Ser Asp Cys (Xaa)n5 Cys Ile Cys Arg Gly Asn Gly Tyr Cys Gly (SEQ ID NO: 6)

In one embodiment of the Fibronectin Extra Domain B binding peptide Ile/Val is Ile. In one embodiment of the Fibronectin Extra Domain B binding peptide Ile/Val is Val.

In one embodiment, the present invention provides a Fibronectin Extra Domain B binding peptide, which comprises an amino acid sequence selected from the group consisting of:
(i) TrpLysCysGlnProThrAsnGlyTyrArgIleArgCysArgArgAspSerAspCysPro GlyAspCysIleCysArgGlyAsnGlyTyrCysGly (SEQ ID NO: 7),
(ii) SerValCysLysAsnValSerIleMetArgIleArgLeuCysArgArgAspSerAspCys ProGlyAlaCysIleCysArgGlyAsnGlyTyrCysGly (SEQ ID NO: 8),
(iii) SerValCysAlaHisTyrAsnThrIleArgValArgLeuCysArgArgAspSerAspCys ProGlyAlaCysIleCysArgGlyAsnGlyTyrCysGly (SEQ ID NO: 9),
(iv) ProMetCysThrGlnArgLysAsnArgIleArgLeuCysArgArgAspSerAspCysThr GlyAlaCysIleCysArgGlyAsnGlyTyrCysGly (SEQ ID NO: 11),
(v) SerValCysLysGlnAlaAsnPheValArgIleArgLeuCysArgArgAspSerAspCys ProGlyAlaCysIleCysArgGlyAsnGlyTyrCysGly (SEQ ID NO: 12),
(vi) AlaMetCysThrGlnArgLysAsnArgIleArgLeuCysArgArgAspSerAspCysThr GlyAlaCysIleCysArgGlyAsnGlyTyrCysGly (SEQ ID NO: 13),
(vii) ProAlaCysThrGlnArgLysAsnArgIleArgLeuCysArgArgAspSerAspCysThr GlyAlaCysIleCysArgGlyAsnGlyTyrCysGly (SEQ ID NO: 14),
(viii) ProMetCysAlaGlnArgLysAsnArgIleArgLeuCysArgArgAspSerAspCysThr GlyAlaCysIleCysArgGlyAsnGlyTyrCysGly (SEQ ID NO: 15),
(ix) ProMetCysThrAlaArgLysAsnArgIleArgLeuCysArgArgAspSerAspCysThr GlyAlaCysIleCysArgGlyAsnGlyTyrCysGly (SEQ ID NO: 16),
(x) ProMetCysThrGlnAlaLysAsnArgIleArgLeuCysArgArgAspSerAspCysThr GlyAlaCysIleCysArgGlyAsnGlyTyrCysGly (SEQ ID NO: 17),
(xi) ProMetCysThrGlnArgAlaAsnArgIleArgLeuCysArgArgAspSerAspCysThr GlyAlaCysIleCysArgGlyAsnGlyTyrCysGly (SEQ ID NO: 18),
(xii) ProMetCysThrGlnArgLysAlaArgIleArgLeuCysArgArgAspSerAspCysThr GlyAlaCysIleCysArgGlyAsnGlyTyrCysGly (SEQ ID NO: 19),
(xiii) ProMetCysThrGlnArgLysAsnArgIleArgLeuCysAlaArgAspSerAspCysThr GlyAlaCysIleCysArgGlyAsnGlyTyrCysGly (SEQ ID NO: 24), and
(xiv) ProMetCysThrGlnArgLysAsnArgIleArgLeuCysArgAlaAspSerAspCysThr GlyAlaCysIleCysArgGlyAsnGlyTyrCysGly (SEQ ID NO: 25)

In one embodiment, the Fibronectin Extra Domain B binding peptide forms or is part of a scaffold. In one embodiment, the Fibronectin Extra Domain B binding peptide is stabilized by a covalent modification. In one embodiment, the covalent modification is cyclization. In one embodiment, the cyclization is via one or more disulfide bridges.

In one embodiment, the Fibronectin Extra Domain B binding peptide forms and/or is part of a cystine knot structure, preferably inhibitor cystine knot structure. In one embodiment, the amino acid sequence motif is located within loop 1 of a cystine knot structure, preferably inhibitor cystine knot structure, preferably at the C-terminal end of loop 1 of a cystine knot structure, preferably inhibitor cystine knot structure. In one embodiment, the cystine knot structure is based on the open chain trypsin inhibitor II from *Momordica cochinchinensis* (oMCoTI-II).

In one embodiment, the Fibronectin Extra Domain B binding peptide further comprising at least one fusion partner. In one embodiment, the fusion partner comprises a heterologous amino acid sequence.

The invention also provides a Fibronectin Extra Domain B (EDB) binding agent comprising a Fibronectin Extra Domain B binding peptide described herein. The invention also provides a Fibronectin Extra Domain B (EDB) binding agent comprising one or more such as 2, 3, 4, 5, 6 or more Fibronectin Extra Domain B binding peptides described herein, wherein the Fibronectin Extra Domain B binding peptides may be identical or different.

In one embodiment of the Fibronectin Extra Domain B binding agent, the Fibronectin Extra Domain B binding peptide is covalently and/or non-covalently, preferably covalently associated with at least one further moiety.

In one embodiment of the Fibronectin Extra Domain B binding peptide or the Fibronectin Extra Domain B binding agent, the fusion partner or further moiety comprises a carrier protein, label, reporter, or tag. In one embodiment, the reporter is a reporter for an immunological assay, wherein the reporter preferably is selected from the group consisting of alkaline phosphatase, horseradish peroxidase, or a fluorescent molecule. In one embodiment, the fusion partner or further moiety is selected from the group consisting of a His6-cassette, thioredoxin, an S-tag, biotin or a combination thereof.

In one embodiment, the Fibronectin Extra Domain B binding agent comprises at least two subunits which are covalently and/or non-covalently associated, each of said subunits comprising a Fibronectin Extra Domain B binding peptide described herein, wherein the Fibronectin Extra Domain B binding peptides may be identical or different.

According to the invention, in one embodiment, non-covalent association is via a compound comprising streptavidin. According to the invention, in one embodiment, covalent association is via peptidic and/or non-peptidic linkers.

Thus, in one embodiment, the Fibronectin Extra Domain B binding peptide of the invention is present in oligomeric or multimeric form. In this embodiment, two or more Fibronectin Extra Domain B binding peptides of the invention which may be identical or different may be linked or coupled by covalent or non-covalent bonding, such as through biotin/streptavidin. Thus, Fibronectin Extra Domain B binding peptides of the invention may form dimers, trimers, tetramers etc.

In one embodiment, the Fibronectin Extra Domain B binding agent of the invention comprises at least four subunits. In one embodiment, the Fibronectin Extra Domain B binding agent of the invention comprises at least three subunits.

The invention also provides a Fibronectin Extra Domain B (EDB) binding agent which comprises the Fibronectin Extra Domain B binding peptide described herein or the Fibronectin Extra Domain B binding agent described herein covalently and/or non-covalently, preferably covalently associated with at least one detectable label or reporter and/or at least one therapeutic effector moiety.

In one embodiment, the Fibronectin Extra Domain B binding peptide described herein or the Fibronectin Extra Domain B binding agent described herein binds to native epitopes of Fibronectin Extra Domain B.

In one embodiment, the Fibronectin Extra Domain B is expressed by endothelial cells and/or tumor cells.

In one embodiment of the Fibronectin Extra Domain B binding peptide described herein or the Fibronectin Extra Domain B binding agent described herein binding is a specific binding.

The present invention also provides a recombinant nucleic acid which encodes a Fibronectin Extra Domain B binding peptide described herein. In one embodiment, the recombinant nucleic acid is in the form of a vector or in the form of RNA.

The present invention also provides a host cell comprising a recombinant nucleic acid described herein.

Another object of the invention is to provide means and methods for diagnosis, detection or monitoring, i.e. determining the regression, progression, course and/or onset, of a disease expressing Fibronectin Extra Domain B such as a cancer disease.

The present invention provides a test kit comprising the Fibronectin Extra Domain B binding peptide described herein or the Fibronectin Extra Domain B binding agent described herein. In one embodiment, the test kit further comprises at least one additional reagent for performing an immunoassay and/or instructions for use of the kit for performing an immunoassay. In one embodiment, the test kit is a diagnostic test kit.

Diagnostic test kits of the invention may be useful in the methods for diagnosis, detection or monitoring of cancer of the invention. These kits may include informative pamphlets, for example, pamphlets informing one how to use reagents to practice a method disclosed herein.

The present invention also provides an assay device comprising the Fibronectin Extra Domain B binding peptide described herein or the Fibronectin Extra Domain B binding agent described herein. In one embodiment, the assay device is an enzyme-linked immunosorbent assay device. In one embodiment of the assay device, the Fibronectin Extra Domain B binding peptide or Fibronectin Extra Domain B binding agent is releasably or non-releasably immobilised on a solid support.

The present invention also provides a method for assaying for the presence and/or amount of Fibronectin Extra Domain B (EDB) in a sample comprising using the Fibronectin Extra Domain B binding peptide described herein or the Fibronectin Extra Domain B binding agent described herein.

The present invention also provides a method for diagnosis, detection or monitoring of cancer in a patient comprising assaying for the presence and/or amount of Fibronectin Extra Domain B (EDB) in said patient using the Fibronectin Extra Domain B binding peptide described herein or the Fibronectin Extra Domain B binding agent described herein.

In a particular aspect, the invention relates to a method for detection, i.e. determining the position or site, of a cancer disease, e.g. a particular tissue or organ. In one embodiment, said method comprises administering a Fibronectin Extra Domain B binding compound, e.g. binding peptide or agent, of the invention which is coupled to a detectable label to a patient.

Labelling of a tissue or organ in said patient may indicate the presence of or risk for a cancer disease in said tissue or organ.

In one embodiment, the tissue or organ is a tissue or organ which when the tissue or organ is free of cancer does not substantially express Fibronectin Extra Domain B.

In one embodiment of the methods of the invention, said assaying is performed on a biological sample isolated from said patient.

In one embodiment, the biological sample is isolated from a patient having a cancer disease, being suspected of having or falling ill with a cancer disease or having a potential for a cancer disease. In one embodiment, the biological sample is from a tissue or organ which when the tissue or organ is free of cancer does not substantially express Fibronectin Extra Domain B.

Typically, the level of Fibronectin Extra Domain B in a biological sample is compared to a reference level, wherein a deviation from said reference level is indicative of the presence and/or stage of a cancer disease in a patient. The reference level may be a level as determined in a control sample (e.g., from a healthy tissue or subject) or a median level from healthy subjects. A "deviation" from said reference level designates any significant change, such as an increase or decrease by at least 10%, 20%, or 30%, preferably by at least 40% or 50%, or even more. The presence of Fibronectin Extra Domain B and/or a quantity of Fibronectin Extra Domain B which is increased compared to a reference level, e.g. compared to a patient without a cancer disease, may indicate the presence of or risk for (i.e. a potential for a development of) a cancer disease in said patient.

In one embodiment, a biological sample and/or a control/reference sample is from a tissue or organ corresponding to the tissue or organ which is to be diagnosed, detected or monitored with respect to affection by a cancer disease; e.g. the cancer disease which is to be diagnosed, detected or monitored is brain cancer and the biological sample and/or control/reference sample is brain tissue.

In one embodiment, the biological sample and/or a control/reference sample is from a tissue or organ which when the tissue or organ is free of cancer does not substantially express Fibronectin Extra Domain B. The indication of the presence of or risk for a cancer disease in a patient by the methods of the invention may indicate that the cancer disease is in said tissue or organ or that said tissue or organ is at risk for said cancer disease.

The methods for diagnosis, detection or monitoring allow quantitative and/or qualitative evaluations, e.g., absolute and/or relative measure of target molecules, e.g. expression levels of Fibronectin Extra Domain B.

Means for accomplishing said assaying for the presence and/or amount of Fibronectin Extra Domain B are described herein and will be apparent to the skilled person. Typically, the assaying in the methods of the invention involves the use of labeled ligands which specifically bind to Fibronectin Extra Domain B, e.g. a compound of the invention that specifically binds to Fibronectin Extra Domain B directly or indirectly bound to a label that provides for detection, e.g. indicator enzymes, radiolabels, fluorophores, or paramagnetic particles.

In one embodiment, the presence of Fibronectin Extra Domain B or an amount of Fibronectin Extra Domain B which is higher compared to a reference without cancer indicates that the patient has cancer.

The methods of monitoring according to the invention preferably comprise assaying for the presence and/or amount of Fibronectin Extra Domain B in a first sample at a first point in time and in a further sample at a second point in time, wherein the regression, progression, course and/or onset of a cancer disease may be determined by comparing the two samples.

A quantity of Fibronectin Extra Domain B which is decreased in a biological sample compared to a biological sample taken earlier from a patient may indicate a regression, a positive course, e.g. a successful treatment, or a reduced risk for an onset of a cancer disease in said patient.

A quantity of Fibronectin Extra Domain B which is increased in a biological sample compared to a biological sample taken earlier from a patient may indicate a progression, a negative course, e.g. an unsuccessful treatment, recurrence or metastatic behaviour, an onset or a risk for an onset of a cancer disease in said patient.

In one embodiment of the methods of the invention, assaying for the presence and/or amount of Fibronectin Extra Domain B comprises:
contacting a sample with the Fibronectin Extra Domain B binding peptide or the Fibronectin Extra Domain B binding agent, and
(ii) detecting the formation of and/or determining the quantity of a complex between the Fibronectin Extra Domain B binding peptide or the Fibronectin Extra Domain B binding agent and Fibronectin Extra Domain B.

In one embodiment of the methods of the invention, the Fibronectin Extra Domain B binding peptide or Fibronectin Extra Domain B binding agent comprises or is conjugated to at least one detectable label or reporter.

In one embodiment, the method of the invention is performed in the context of an immunoassay.

In one embodiment of the methods of the invention, the Fibronectin Extra Domain B binding peptide or Fibronectin Extra Domain B binding agent is releasably or non-releasably immobilised on a solid support.

Binding of a Fibronectin Extra Domain B binding compound according to the invention to Fibronectin Extra Domain B can interfere with the function of Fibronectin Extra Domain B. Furthermore, a Fibronectin Extra Domain B binding compound may be attached to therapeutic effector moieties, e.g., radiolabels, cytotoxins, cytotoxic enzymes, and the like, and binding of the compound to Fibronectin Extra Domain B can selectively target and kill cells that express Fibronectin Extra Domain B or cells that are associated with cells that express Fibronectin Extra Domain B, in particular cancer cells. In one embodiment, said compound reduces tumor cell growth and/or induces tumor cell death and thus, has a tumor-inhibiting or tumor-destroying effect. Accordingly, the Fibronectin Extra Domain B binding compounds described herein may be used in therapy, in particular for a prophylactic and/or therapeutic treatment of cancer diseases.

A positive diagnosis of a cancer disease as described above using the methods of the present invention may indicate a cancer disease which is amenable to the methods of treatment described herein.

Thus, another object of the invention is to provide means and methods for therapeutic and/or prophylactic treatment of a cancer disease.

The present invention also provides a pharmaceutical composition comprising the Fibronectin Extra Domain B binding peptide described herein, the Fibronectin Extra Domain B binding agent described herein, the recombinant nucleic acid described herein or the host cell described herein.

A pharmaceutical composition of the invention may comprise a pharmaceutically acceptable carrier and may optionally comprise further substances as described herein.

The present invention also provides the Fibronectin Extra Domain B binding peptide described herein, the Fibronectin Extra Domain B binding agent described herein, the recombinant nucleic acid described herein, the host cell described herein or the pharmaceutical composition described herein for use in therapy, in particular for use in treating or preventing cancer in a patient.

The present invention also provides the Fibronectin Extra Domain B binding peptide described herein or the Fibronectin Extra Domain B binding agent described herein for use in targeting cancer in a patient.

The present invention also provides a method of treating a patient comprising administering to the patient the Fibronectin Extra Domain B binding peptide described herein, the Fibronectin Extra Domain B binding agent described herein, the recombinant nucleic acid described herein, the host cell described herein or the pharmaceutical composition described herein, wherein, preferably, the patient has cancer or is at risk of developing cancer.

In one embodiment of the above aspects, the Fibronectin Extra Domain B binding peptide or Fibronectin Extra Domain B binding agent comprises or is conjugated to at least one therapeutic effector moiety.

In one embodiment of the above aspects, the cancer is Fibronectin Extra Domain B-positive and/or involves cells expressing Fibronectin Extra Domain B.

According to all aspects of the invention, cancer is preferably selected from the group consisting of breast cancer, brain cancer, pulmonary or lung cancer, colorectal cancer, colon cancer, esophagus cancer, head and neck cancer, stomach cancer, pancreas cancer, kidney cancer, cervix cancer, ovary cancer, bladder cancer, or prostate cancer.

According to all aspects of the invention, Fibronectin Extra Domain B preferably comprises the amino acid sequence according to SEQ ID NO: 2 of the sequence listing or a variant of said amino acid sequence.

In one aspect, the invention provides agents as described herein for use in the methods of treatment described herein. In one embodiment, the invention provides a pharmaceutical composition as described herein for use in the methods of treatment described herein.

The treatments described herein can be combined with surgical resection and/or radiation and/or traditional chemotherapy.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual, $2^{nd}$ Edition*, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention relates to Fibronectin Extra Domain B binding compounds or agents such as Fibronectin Extra Domain B binding peptides or agents comprising one or more Fibronectin Extra Domain B binding peptides.

Fibronectins (FNs) are high-molecular-mass adhesive glycoproteins present in the extracellular matrix (ECM) and body fluids, constituted by a dimer composed of two subunits of about 250 kDa linked at the C-termini by two disulfide bonds. Each monomer consists of three types of repeating units: 12 FN repeats of type I (about 40 amino acids each), two type II (about 60 amino acids) and 15-17 type III (about 90 amino acids). Fibronectin mediates a wide variety of cellular interactions and is involved in a number of processes, such as cell adhesion, the establishment and maintenance of normal cell morphology, cell migration, growth and differentiation. It interacts with several other ECM and cell surface proteins, including collagen, heparin, fibrin, and cell membrane receptors. Finally, FN can be a ligand for numerous integrins, including the classic FN receptor alpha5-beta1 on the RGD sequence of repeat III-10. Fibronectins are the product of a single gene localized on chromosome 2, but different isoforms arise from the alternative splicing of the pre-mRNA, a process that for some ECM proteins is modulated by cytokines and extracellular/intracellular pH in three sites: the type III connecting sequence (IIICS), a complete type III repeat, extra domain A (EDA), and a complete type III repeat, extra domain B (EDB). The last of these is a complete type III homology repeat of 91 amino acids, in which exon usage or skipping leads to inclusion or exclusion of these type III repeats. Thus, the isoform extra domain B (EDB) comprises an additional type III domain of 91 amino acids, which is specifically inserted between FN domains 7 and 8. The insertion of the EDB between the FN type III repeats 7 and 8 induces a conformational modification that unmasks a cryptic sequence and hinders others. Fibronectin Extra Domain B is usually absent in normal adult tissues, but involved in tissue remodeling and angiogenesis. In addition, Fibronectin Extra Domain B has been found in many different cancer types with abundant expression pattern in the neovasculature of several aggressive solid human tumors.

According to the invention, the term "Fibronectin Extra Domain B" preferably relates to human Fibronectin Extra Domain B.

Preferably, the term "Fibronectin Extra Domain B" or the abbreviation "EDB" relates to a certain fibronectin isoform containing an extra domain B repeat. In one embodiment, the term "Fibronectin Extra Domain B" or the abbreviation "EDB" relates to a nucleic acid comprising, preferably consisting of the nucleic acid sequence of SEQ ID NO: 1 of the sequence listing or a variant of said nucleic acid sequence and to a protein encoded by this nucleic acid, preferably to a protein comprising, preferably consisting of the amino acid sequence of SEQ ID NO: 2 of the sequence listing or a variant of said amino acid sequence. In certain embodiments, the term "Fibronectin Extra Domain B" or the abbreviation "EDB" is also used herein to specifically designate the extra domain B repeat portion of EDB fibronectin. In one embodiment, such extra domain B repeat portion of EDB fibronectin comprises the amino acid sequence shown in SEQ ID NO: 28 of the sequence listing or a variant of said amino acid sequence.

Fibronectin Extra Domain B is expressed in cancers of various origins such as head and neck cancer, brain cancer, colorectal cancer, lung cancer, prostate cancer and breast cancer. Fibronectin Extra Domain B is a valuable target for the diagnosis, prevention and/or treatment of primary tumors and metastases.

A Fibronectin Extra Domain B binding agent of the invention has the ability of binding to Fibronectin Extra Domain B, i.e. the ability of binding to an epitope present in Fibronectin Extra Domain B. In one embodiment, a Fibronectin Extra Domain B binding agent binds to Fibronectin Extra Domain B expressed around angiogenic vasculature, such as in tumorigenesis. In one embodiment, a Fibronectin Extra Domain B binding agent binds to Fibronectin Extra Domain B expressed within and/or around tumor tissues such as in the extracellular matrix of tumor tissues and/or in and/or at tumor vessels such as tumor neovessels. In particular preferred embodiments, a Fibronectin Extra Domain B binding agent binds to native epitopes of Fibronectin Extra Domain B.

The term "epitope" refers to a part or portion in a molecule that is recognized by a binding agent. For example, epitopes are the discrete, three-dimensional sites on a molecule, which are recognized by a binding agent. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

According to the invention, the term "Fibronectin Extra Domain B binding agent" or "Fibronectin Extra Domain B binding compound" includes any compound 5 (including complexes of molecules) that has a binding capacity to Fibronectin Extra Domain B. Preferably, such binding agent is or comprises at least one Fibronectin Extra Domain B binding peptide of the invention. If a Fibronectin Extra Domain B binding agent comprises at least two Fibronectin Extra Domain B binding peptides of the invention (which may be identical or different) these peptides may be covalently or non-covalently associated (i.e., bound). Fibronectin Extra Domain B binding agents may comprise one or more Fibronectin Extra Domain B binding peptides covalently or non-covalently associated to any other compound or moiety such as labels or therapeutic effector moieties.

According to the present invention, an agent is capable of binding to a predetermined target such as Fibronectin Extra Domain B if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, $10^2$-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

According to the invention, the term "binding" preferably relates to a specific binding.

"Specific binding" means that an agent binds stronger to a target for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than $10^2$-fold, $10^3$-fold, $10^4$-fold, $10^5$-fold, $10^6$-fold, $10^7$-fold, $10^8$-fold, $10^9$-fold, or $10^{10}$-fold lower than the dissociation constant ($K_D$) for the target to which the agent does not bind specifically.

Preferably, an agent is specific for a predetermined target such as Fibronectin Extra Domain B if it is capable of binding to said predetermined target while it is not (substantially) capable of binding to other targets, i.e. has no significant affinity for other targets and does not significantly bind to other targets in standard assays. Preferably, an agent is specific for Fibronectin Extra Domain B if the affinity for and the binding to such other targets does not significantly exceed the affinity for or binding to Fibronectin Extra Domain B-unrelated proteins such as bovine serum albumin (BSA), casein, human serum albumin (HSA) or any other specified polypeptide. Preferably, an agent is specific for a predetermined target if it binds to said target with a $K_D$ that is at least $10^2$-fold, $10^3$-fold, $10^4$-fold, $10^5$-fold, $10^6$-fold, $10^7$-fold, $10^8$-fold, $10^9$-fold, or $10^{10}$-fold lower than the $K_D$ for binding to a target for which it is not specific.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using surface plasmon resonance analytic (e.g. Biacore), using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular interaction can vary if measured under different conditions, e.g., salt concentration, pH. Thus, measurements of affinity and other binding parameters, e.g., $K_D$, $IC_{50}$, are preferably made with standardized solutions of binding agent and target, and a standardized buffer.

In one embodiment of the invention, a cancer is a Fibronectin Extra Domain B-positive cancer. According to the invention, the term "Fibronectin Extra Domain B-positive cancer" or similar terms means a cancer involving or being associated with Fibronectin Extra Domain B, in particular a cancer involving cells such as tumor cells and/or endothelial cells expressing Fibronectin Extra Domain B. In one embodiment, the term "Fibronectin Extra Domain B-positive cancer" or similar terms means a cancer wherein Fibronectin Extra Domain B is expressed within and/or around tumor tissues such as in the extracellular matrix of tumor tissues and/or in and/or at tumor vessels such as tumor neovessels.

In one embodiment, a cancer involves or is associated with Fibronectin Extra Domain B if Fibronectin Extra Domain B is spatially linked to said cancer, in particular if Fibronectin Extra Domain B is present in said cancer such as in the extracellular matrix of tumor tissues and/or in and/or at tumor vessels. Preferably, a cancer involving or being associated with Fibronectin Extra Domain B contains cells expressing Fibronectin Extra Domain B. Said cells may be cancer cells or cells being associated with cancer such as endothelial cells, in particular cancer-associated endothelial cells such as endothelial cells of tumor vessels such as tumor neovessels.

The terms "part" or "fragment" are used interchangeably herein and refer to a continuous element. A part or fragment of a protein sequence preferably comprises at least 6, in particular at least 8, at least 12, at least 15, at least 20, at least 30, at least 50, or at least 100 consecutive amino acids of the protein sequence.

The term "portion" refers to a continuous and/or non-continuous element. A portion of a protein sequence preferably comprises at least 6, in particular at least 8, at least 12, at least 15, at least 20, at least 30, at least 50, or at least 100 consecutive and/or non-consecutive amino acids of the protein sequence.

According to the invention, Fibronectin Extra Domain B is not (substantially) expressed if the level of expression is below the detection limit and/or if the level of expression is too low to allow binding by Fibronectin Extra Domain B-specific binding agents.

According to the invention, Fibronectin Extra Domain B is expressed if the level of expression is above the detection limit and/or if the level of expression is high enough to allow binding by Fibronectin Extra Domain B-specific binding agents. Preferably, Fibronectin Extra Domain B expressed by a cell is secreted from the cell such as into the extracellular matrix.

The term "scaffold" relates to a structure conferring rigidity, e.g., conferring rigidity to a Fibronectin Extra Domain B binding peptide or amino acid sequence motif described herein.

A cystine knot is a protein structural motif containing at least three disulfide bridges (formed from pairs of cysteine molecules). It comprises an embedded ring formed by two disulfide bonds and their connecting backbone segments which is threaded by a third disulfide bond. This structure is preferably associated with a beta-sheet structure. Peptides containing a cystine knot are preferably 25-60, preferably 25-50 or 25-40 amino acid residues long.

Cystine knots occur in many peptides or proteins across many species and provide considerable structural stability. There are three types of cystine knots, which differ in the topology of the disulfide bonds: Growth Factor Cystine Knot (GFCK), Inhibitor Cystine Knot (ICK) and Cyclic Cystine Knot, or cyclotide.

An inhibitor cystine knot (ICK) or knottin is a protein structural motif containing three disulfide bridges. Along with the sections of polypeptide between them, two disulfides (linking the first and fourth cysteine and the second and fifth cysteine, respectively) form a loop through which the third disulfide bond (linking the third and sixth cysteine in the sequence) passes, forming a knot. The motif is common in invertebrate toxins such as those from arachnids and molluscs. The motif is also found in some inhibitor proteins found in plants.

Thus, according to the invention, an ICK motif involves two intracysteine backbone segments and their connecting disulfide bonds, CysI-CysIV and CysII-CysV, which form a ring that is penetrated by the third disulfide bond, CysIII-CysVI.

The ICK motif is similar to the cyclic cystine knot or cyclotide, but lacks the cyclisation of the polypeptide backbone which is present in the latter family. The growth factor cystine knot (GFCK) shares the motif but its topology is such that it is the bond between the first and fourth cysteine which threads through the loop (formed between the second and fifth cysteine and the third and sixth cysteine, respectively).

The cyclotides fall into two main structural subfamilies. Moebius cyclotides, the less common of the two, contain a cis-proline in loop 5 that induces a local 180° backbone twist, whereas bracelet cyclotides do not. The trypsin inhibitor cyclotides are classified in their own family based on sequence variation and natural activity.

Trypsin inhibitor cyclotides are more homologous to a family of non-cyclic trypsin inhibitors from squash plants known as knottins or inhibitor cystine knots than they are to the other cyclotides.

MCoTI-I and MCoTI-II are natural polypeptides from the seeds of the spinal gourd *Momordica cochinchinensis*. These polypeptides are inhibitors of trypsin-like proteases and contain an additional loop connecting the amino- and the carboxy-terminus and a knotted arrangement of three conserved disulfide bonds. The cystine knot is defined by three intramolecular disulfide bonds, where CysICysIV and CysII-CysV of the linear peptide sequence form a ring that is penetrated by the third disulfide bond, CysIII-CysVI. This arrangement provides a well-defined and extremely stable scaffold that exhibits extraordinary thermal and proteolytic stability. Due to structural similarity and common biological activity, i.e., inhibition of proteases of the trypsin family, MCoTI-I and MCoTI-II have been grouped into the squash inhibitor cystine-knot (ICK) family of small protease inhibitors. Members of this family are open-chain molecules forming a small triple-stranded β-sheet and a short $3_{10}$ helix, held together by three intramolecular disulfide bonds to give rise to a cystine-knot framework. MCoTI-I and MCoTI-II are the only known members of the large family of squash inhibitors that are cyclic. Open-chain variants of MCoTI-II that lack the cyclization loop have been synthesized.

In certain embodiments, a Fibronectin Extra Domain B binding peptide described herein forms and/or is part of a cystine knot structure, preferably inhibitor cystine knot structure. In certain embodiments, an amino sequence motif described herein is part of a cystine knot structure, preferably inhibitor cystine knot structure. In one embodiment, an amino acid sequence motif described herein is located within loop 1 of a cystine knot structure, preferably inhibitor cystine knot structure. In one embodiment, an amino acid sequence motif described herein is located at the C-terminal end of loop 1 of a cystine knot structure, preferably inhibitor cystine knot structure. In one embodiment, the first loop (loop 1) of a cysteine knot structure is located between the first cysteine and the second cysteine of the cystine knot structure.

According to the invention, peptides described herein can be synthetically produced by chemical synthesis methods which are well known in the art, either as an isolated peptide or as a part of another peptide or polypeptide. Alternatively, a peptide can be produced in a microorganism which produces the peptide which is then isolated and if desired, further purified. Thus, the peptide can be produced in microorganisms such as bacteria, yeast, or fungi; in a eukaryote cells such as mammalian or insect cells; or, in a recombinant virus vector such as adenovirus, poxvirus, herpesvirus, Simliki forest virus, baculovirus, bacteriophage, sindbis virus, or sendai virus. Suitable bacteria for producing the peptide include *Escherichia coli, Bacillus subtilis*, or any other bacterium that is capable of expressing peptides. Suitable yeast types for expressing the peptide include, but are not limited to *Saccharomyces cerevisiae, Schizosaccharomyces pombe, Candida*, or any other yeast capable of expressing peptides. Methods for using the aforementioned bacteria, recombinant virus vectors, eukaryote cells to produce peptides are well known in the art.

To produce a peptide, the nucleic acid encoding the peptide is preferably in a plasmid and the nucleic acid is operably linked to a promoter which effects expression of the peptide in a microorganism. Suitable promoters include, but are not limited to, T7 phage promoter, T3 phage promoter, β-galactosidase promoter, and the Sp6 phage promoter. Methods for isolating and purifying peptides are well known in the art and include methods such as gel filtration, affinity chromatography, ion exchange chromatography, or centrifugation.

The peptides of the invention, either by themselves or as part of a fusion peptide, can be conjugated to a heterologous peptide or protein. Such heterologous proteins include, but are not limited to, carrier proteins such as bovine serum albumen (BSA), and reporter enzymes which include, but are not limited to, horseradish peroxidase or alkaline phosphatase. Further, the peptides or fusion peptides comprising the peptide can be chemically conjugated to fluorescent reporter molecules which include, but are not limited to, fluorescein or R-phycoerythrin.

Methods for conjugating carrier proteins, enzymes, and fluorescent reporter molecules to peptides and fusion peptides are well known in the art.

To facilitate isolation of the peptide, a fusion polypeptide can be made wherein the peptide is translationally fused (covalently linked) to a heterologous tag such as a heterologous polypeptide or polyhistidine, preferably six histidine residues, which allows for the simplified recovery of the fusion polypeptide, e.g. its isolation by affinity chromatography or metal affinity chromatography, preferably nickel affinity chromatography. In some instances it can be desirable to remove the tag after purification. Therefore, it is also contemplated that the fusion polypeptide comprises a cleavage site at the junction between the peptide and the heterologous tag. The cleavage site consists of an amino acid sequence that is cleaved with an enzyme specific for the amino acid sequence at the site.

The Fibronectin Extra Domain B binding agents described herein may be used in assays for assaying the presence or amount of Fibronectin Extra Domain B or Fibronectin Extra Domain B antibodies. Such assays may be carried out in a number of ways, including but not limited to immunodetection, and include ELISA, in particular peptide ELISA, competitive binding assays, RIA and the like. The methods of the invention allow quantitative and/or qualitative evaluations, e.g., absolute and/or relative evaluations, of Fibronectin Extra Domain B or Fibronectin Extra Domain B antibodies.

In general, the assays are performed using an enzyme-linked immunosorbent assay (ELISA) embodiment.

The term "enzyme-linked immunosorbent assay or ELISA", as used herein, relates to a method for quantitatively or semi-quantitatively determining protein concentrations from a sample, e.g. blood plasma, serum or cell/tissue extracts, in a multi-well plate format (usually 96-wells per plate). Broadly, proteins in solution are adsorbed to ELISA plates. Antibodies specific for the protein of interest may be used to probe the plate. Background is minimized by optimizing blocking and washing methods (as for IHC), and specificity is ensured via the presence of positive and negative controls. Detection methods are usually colorimetric or chemiluminescence based.

A microtiter plate may be provided containing a plurality of wells wherein a first well or series of wells contains a monoclonal antibody against Fibronectin Extra Domain B immobilized to the surface therein. A sample may be added to the wells containing the bound monoclonal antibody. The Fibronectin Extra Domain B in the sample binds to the monoclonal antibody. The ELISA is incubated for a time sufficient for antibody complexes to form. A peptide of the invention may be further added. The peptide may be part of a fusion polypeptide. Afterwards, the wells are washed to remove any unbound material. The wells may then be incubated with a labeled antibody or an antibody conjugated to a reporter molecule that binds to the fusion polypeptide to form a complex which can be detected. A detectable signal from the label or reporter indicates that the sample contains Fibronectin Extra Domain B whereas an absence of a signal may indicate that the sample does not contain Fibronectin Extra Domain B. When the fusion polypeptide comprises a label or reporter molecule such as a reporter enzyme such as alkaline phosphatase, the antibody complex can be detected directly without the need for a labeled antibody.

Alternatively, a microtiter plate may be provided containing a plurality of wells wherein a first well or series of wells contains the peptide of the invention, which may be conjugated to a carrier protein or fusion polypeptide, immobilized to the surface therein. Sample may be added to the wells containing the bound peptides. The Fibronectin Extra Domain B in the sample and the peptide bound to the well surfaces are incubated for a time sufficient for complexes to form. Afterwards, the wells are washed to remove any unbound material. The amount of Fibronectin Extra Domain B that is bound to the immobilized peptides in the well is determined by incubating the wells with a labeled antibody or an antibody conjugated to a reporter molecule that binds to the Fibronectin Extra Domain B to form a complex that can be detected. A detectable signal from the reporter indicates the sample contains Fibronectin Extra Domain B whereas an absence of a signal indicates that the sample does not contain Fibronectin Extra Domain B. The intensity of the signal may provide an estimate of the concentration of Fibronectin Extra Domain B in the sample.

Peptides of the invention may also be used in methods for detecting the presence of antibodies against Fibronectin Extra Domain B. The design of suitable immunoassays to put these methods into effect may be subject to a great deal of variation, and a variety of these immunoassays are known in the art. Suitable immunoassay protocols may be based, for example, upon competition, or direct reaction, or sandwich type assays. The immunoassay protocols used may also, for example, use solid supports, or may be by immunoprecipitation. Assays may involve the use of labelled peptides and the labels may be, for example, fluorescent, chemiluminescent, radioactive, or dye molecules. Particular preferred assays are enzyme-labelled and mediated immunoassays, such as ELISA assays.

Accordingly, the peptides may also be used in an assay such as an ELISA assay to determine antibody against Fibronectin Extra Domain B in a sample. For this purpose, the wells of ELISA plates may be coated with peptides. Fibronectin Extra Domain B and the peptide bound to the well surfaces may be incubated for a time sufficient for complexes to form. Subsequently, a sample such as plasma may be added and the detection of Fibronectin Extra Domain B specific antibodies (primary antibody) may be performed with a labelled secondary antibody directed against the primary antibody.

When used as an assay reagent as described herein, a peptide of the invention may be conjugated to a label.

According to the invention, a label is any entity the presence of which can be readily detected. Preferably the label is a direct label. Direct labels are entities which, in their natural state, are readily visible either to the naked eye, or with the aid of an optical filter and/or applied stimulation, e.g. UV light to promote fluorescence. Examples include radioactive, chemiluminescent, electroactive (such as redox labels), and fluorescent compounds. Direct particulate labels, such as dye sols, metallic sols (e.g. gold) and coloured latex particles, are also very suitable and are, along with fluorescent compounds, preferred. Of these options, coloured latex particles and fluorescent compounds are most preferred. Concentration of the label into a small zone or volume should give rise to a readily detectable signal, e.g. a strongly coloured area. Indirect labels, such as enzymes, e.g. alkaline phosphatase and horseradish peroxidase, can also be used, although these usually require the addition of one or more developing reagents such as substrates before a visible signal can be detected.

According to the invention, a label may function to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium. In preferred embodiments, a label comprises a radionuclide such as lutetium-177 or gallium-68 which may be complexed with a ligand such as DOTA (1,4,7,10-tetraazacyclododecane-1,4,7,10-tetraacetic acid) bound to a Fibronectin Extra Domain B binding agent.

Conjugation of the label to the peptide of the invention can be by covalent or non-covalent (including hydrophobic) bonding, or by adsorption. Techniques for such conjugation are commonplace in the art and may be readily adapted for the particular reagents employed.

The term "sample", as used herein, includes any biological sample which may be isolated from a patient and used for analysis purposes. Said sample may be a body fluid sample, a tissue sample, or a cell sample. For example, samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. Said samples may be mixed or pooled, e.g. a sample may be a mixture of a blood sample and a urine sample. Said samples may be provided by removing a body fluid, cell(s), cell colonies, an explant, or a section from a patient, but may also be provided by using a previously isolated sample. For example, a tissue sample may be removed from a patient by conventional biopsy techniques or a blood sample may be taken from a patient by conventional blood collection techniques. The sample, e.g. tissue sample or blood sample, may be obtained from a patient prior to initiation of the therapeutic treatment, during the therapeutic treatment, and/or after the therapeutic treatment.

In one embodiment, the sample is a body fluid sample. The term "body fluid sample", as used herein, refers to any liquid sample derived from the body of a patient. Said body fluid sample may be a blood sample, urine sample, sputum sample, breast milk sample, cerebrospinal fluid (CSF) sample, cerumen (earwax) sample, endolymph sample, perilymph sample, gastric juice sample, mucus sample, peritoneal fluid sample, pleural fluid sample, saliva sample, sebum (skin oil) sample, semen sample, sweat sample, tears sample, vaginal secretion sample, or vomit sample including components or fractions thereof. Said body fluid samples may be mixed or pooled. Thus, a body fluid sample may be a mixture of a blood and a urine sample or a mixture of a blood and cerebrospinal fluid sample. Said body fluid sample may be provided by removing a body liquid from a patient, but may also be provided by using previously isolated body fluid sample material. In one preferred embodiment, the sample is a whole blood sample or a blood fraction sample such as a blood cell fraction, blood serum, or blood plasma sample.

In one embodiment, a biological sample is a sample obtained from a tissue suspected of being affected with a disease such as cancer. In one embodiment, a biological sample is a tumor sample, e.g. a sample obtained from a tumor and comprising tumor cells and/or tumor stroma such as extracellular matrix or extracellular matrix components. According to the invention, the term "biological sample" also includes processed biological samples such as fractions or isolates of biological samples, e.g. nucleic acid and peptide/protein isolates.

According to the invention, a "reference" such as a reference sample or reference organism may be used to correlate and compare the results obtained in the methods of the invention from a test sample or test organism, i.e. a patient. Typically the reference organism is a healthy organism, in particular an organism which does not suffer from a tumor disease.

A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells. The amount of a substance is also reduced in a test sample such as a biological sample compared to a reference sample if it is detectable in the reference sample but absent or not detectable in the test sample.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more. The amount of a substance is also increased in a test sample such as a biological sample compared to a reference sample if it is detectable in the test sample but absent or not detectable in the reference sample.

Fibronectin Extra Domain B binding agents such as peptides of the invention may be bound to a solid support, for example the surface of an immunoassay well or dipstick, and/or packaged into kits in a suitable container along with suitable reagents, controls, instructions and the like.

Accordingly the present invention also provides a kit comprising at least one Fibronectin Extra Domain B binding agent of the present invention. In a preferred embodiment, the kit further comprises at least one additional agent such as one or more suitable reagents for performing an immunoassay, a control, or instructions for use of the kit.

According to the invention there is further provided an assay device comprising at least one Fibronectin Extra Domain B binding agent of the present invention. In one embodiment, the assay device is selected from the group consisting of an enzyme-linked immunosorbent assay device.

Such a device can take different forms, and it can be varied depending on the precise nature of the assay being performed. For example, the peptide of the invention may be coated onto a solid support, typically nitrocellulose or other hydrophobic porous material. Alternatively, the peptide may be coated on a synthetic plastics material, microtitre assay plate, microarray chip, latex bead, filter comprising a cellulosic or synthetic polymeric material, glass or plastic slide, dipstick, capillary fill device and the like. Coating of the peptides to these surfaces can be accomplished by methods known in the art. Protein carriers are typically used for complexing, with BSA or adhesive peptides being the most preferred. In one embodiment, the peptide of the invention is releasably immobilised on the solid support. In a further preferred embodiment, the peptide of the invention is non-releasably immobilised on the solid support.

It is to be understood that the peptides described herein may be delivered to a patient by administering a nucleic acid such as RNA encoding the peptide and/or by administering a host cell comprising a nucleic acid such as RNA encoding the peptide. Thus, a nucleic acid encoding a peptide when administered to a patient may be present in naked form or in a suitable delivery vehicle such as in the form of liposomes or viral particles, or within a host cell. The nucleic acid provided can produce the peptide over extended time periods in a sustained manner. Nucleic acids to be delivered to a patient can be produced by recombinant means. If a nucleic acid is administered to a patient without being present within a host cell, it is preferably taken up by cells of the patient for expression of the peptide encoded by the nucleic acid. If a nucleic acid is administered to a patient while being present within a host cell, it is preferably expressed by the host cell within the patient so as to produce the peptide encoded by the nucleic acid.

The term "nucleic acid", as used herein, is intended to include deoxyribonucleic acid (DNA) and ribonucleic acid (RNA) such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

As used herein, the term "RNA" means a molecule comprising ribonucleotide residues. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). In one embodiment of the invention, the RNA is obtained by in vitro transcription or chemical synthesis. Preferably, mRNA is produced by in vitro transcription using a DNA template. The in vitro transcription methodology is known to the skilled person. For example, there is a variety of in vitro transcription kits commercially available.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., Fibronectin Extra Domain B. An increase in expression refers to an increase by at least 10%, in particular at least 20%, at least 50%, at least 100%, at least 200%, at least 500%, at least 1000%, at least 10000%, or more. In one embodiment, expression is only found in a diseased tissue, while expression in a healthy tissue is repressed.

The term "specifically expressed" means that a protein is essentially only expressed in a specific tissue or organ. For example, a protein specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa.

According to the invention, the term "nucleic acid encoding" means that nucleic acid, if present in the appropriate environment, preferably within a cell, can be expressed to produce a protein or peptide it encodes.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

The term "variant" with respect to, for example, nucleic acid and amino acid sequences, according to the invention includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Furthermore, a "variant" of a specific nucleic acid sequence according to the invention includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

Preferably the degree of identity between a given nucleic acid sequence and a nucleic acid sequence which is a variant of said given nucleic acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of identity is given preferably for a region which is at least about 10%, at least about 20%, at least about 30%, at least about 40%, at least about 50%, at least about 60%, at least about 70%, at least about 80%, at least about 90% or about 100% of the entire length of the reference nucleic acid sequence. For example, if the reference nucleic acid sequence consists of 200 nucleotides, the degree of similarity or identity is given preferably for at least about 20, at least about 40, at least about 60, at least about 80, at least about 100, at least about 120, at least about 140, at least about 160, at least about 180, or about 200 nucleotides, preferably continuous nucleotides. In preferred embodiments, the degree of identity is given for the entire length of the reference nucleic acid sequence.

"Sequence identity" between two nucleic acid sequences indicates the percentage of nucleotides that are identical between the sequences.

The term "percentage identity" is intended to denote a percentage of nucleotides which are identical between the two sequences to be compared, obtained after the best alignment, this percentage being purely statistical and the differences between the two sequences being distributed randomly and over their entire length. Sequence comparisons between two nucleotide sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Preferably, a given nucleic acid sequence and a nucleic acid sequence which is a variant of said given nucleic acid sequence will be capable of hybridizing.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F.M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

Nucleic acids may, according to the invention, be present alone or in combination with other nucleic acids, in particular heterologous nucleic acids. Preferably, a nucleic acid coding for a peptide or protein expresses said peptide or protein. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

According to the invention, a nucleic acid may furthermore be present in combination with another nucleic acid which codes for a peptide controlling secretion of the protein or peptide encoded by said nucleic acid from a host cell. According to the invention, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the invention a vector, where appropriate with a promoter, which controls expression of a nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid can express the nucleic acid.

The term "host cell" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. A nucleic acid may be present in the host cell in the form of a single copy or of two or more copies and, in one embodiment, is expressed in the host cell.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

According to the invention, a peptide may include natural amino acids and non-natural amino acids. In one embodiment, a peptide merely includes natural amino acids.

According to the invention, the term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

According to the invention, the term "cyclic peptide" relates to a peptide or polypeptide chain which forms a ring. A peptide can be cyclized in four different ways: head-to-tail (C-terminus to N-terminus), head-to-side chain, side chain-to-tail or side-chain-to-side-chain. Particularly preferred according to the invention are peptides containing two or more residues containing thiol groups such as cysteines which can form intramolecular disulphide bridges giving cyclic peptides.

According to the invention, a peptide may be covalently or non-covalently bound to one or more other compounds. Such compounds include peptidic compound such as peptides and proteins as well as non-peptidic compounds such as polyethylene glycol (PEG).

In one embodiment, the peptides described herein are PEGylated. PEGylation is the process of covalent attachment of polyethylene glycol (PEG) polymer chains to another molecule, such as a peptide or protein. The covalent attachment of PEG can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo. Such proteins and peptides may be used, for example, in an immunological or diagnostic assay or as therapeutics. Proteins and peptides described according to the invention may be isolated from biological samples such as tissue or cell homogenates and may also be expressed recombinantly in a multiplicity of pro- or eukaryotic expression systems.

The term "antibody" includes a glycoprotein comprising at least two heavy (H) chains and two light (L) chains inter-connected by disulfide bonds, and any molecule comprising an antigen-binding portion of such glycoprotein. The term "antibody" includes monoclonal antibodies, recombinant antibodies, human antibodies, humanized antibodies, chimeric antibodies, molecules comprising binding fragments or derivatives of antibodies, including, without limitation, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target such as Fibronectin Extra Domain B.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the peptide or protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length.

Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The peptides and amino acid variants described herein may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, the term "peptide" or "protein" includes "derivatives" of peptides and proteins. Such derivatives are modified forms of peptides and proteins. Such modifications include any chemical modification and comprise single or multiple substitutions, deletions and/or additions of any molecules associated with the peptide ar protein, such as carbohydrates, lipids, proteins and/or peptides. The term "derivative" also extends to all functional chemical equivalents of said peptides and proteins. Preferably, a modified peptide has increased stability and/or increased immunogenicity.

The Fibronectin Extra Domain B binding agents of the invention may be used in therapeutic approaches. To this end, the Fibronectin Extra Domain B binding agents of the invention may be covalently and/or non-covalently bound to one or more therapeutic effector moieties and/or combined with various components to produce pharmaceutically acceptable compositions. The agents such as peptide described herein may be administered in the form of any suitable pharmaceutical composition.

"Target cell" shall mean any undesirable cell such as a cancer cell. In preferred embodiments, the target cell is associated with or spatially linked to, e.g. in proximity to, Fibronectin Extra Domain B, e.g., the target cell is present within a cancer or tumor involving cells such as tumor cells and/or endothelial cells expressing Fibronectin Extra Domain B. In one embodiment, Fibronectin Extra Domain B is expressed within and/or around tumor tissues such as in the extracellular matrix of tumor tissues and/or in and/or at tumor vessels such as tumor neovessels.

According to the invention, the term "therapeutic effector moiety" means any molecule which may exert a therapeutic effect. According to the invention, a therapeutic effector moiety is preferably selectively guided to Fibronectin Extra Domain B or a cell that is associated with or spatially linked to Fibronectin Extra Domain B. Any agent that exerts a therapeutic effect on cancer cells can be used as the drug for conjugation to a Fibronectin Extra Domain B binding agent. Preferably, conjugation of the drug does not alter or significantly alter the binding characteristics, in particular the specificity, of the Fibronectin Extra Domain B binding agent, as discussed herein.

According to the invention, a therapeutic effector moiety includes anticancer agents, radioisotopes such as radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

Therapeutic effector moieties include, in particular, cytotoxins or cytotoxic agents. A cytotoxin or cytotoxic agent includes any agent that is detrimental to and, in particular, kills cells.

Useful classes of cytotoxic agents include, for example, antitubulin agents, DNA minor groove binders (e.g., enediynes and lexitropsins), DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, nitrosoureas, platinols, pre-forming compounds, purine antimetabolites, puromycins, radiation sensitizers, steroids, taxanes (e.g., paclitaxel and docetaxel), topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Examples of anti-tubulin agents include, but are not limited to, dolastatins (e.g., auristatin E, AFP, MMAF, MMAE, AEB, AEVB), maytansinoids, taxanes (e.g., paclitaxel, docetaxel), T67 (Tularik), vinca alkyloids (e.g., vincristine, vinblastine, vindesine, and vinorelbine), baccatin derivatives, taxane analogs (e.g., epothilone A and B), nocodazole, colchicine and colcimid, estramustine, cryptophysins, cemadotin, combretastatins, discodermolide, and eleutherobin.

Radioisotopes to generate cytotoxic radiopharmaceuticals include, e.g., iodine-131, yttrium-90 or indium-111.

Techniques for conjugating such therapeutic effector moiety (drug) to peptides are well known. The generation of peptide-drug conjugates can be accomplished by any technique known to the skilled artisan. A peptide and a drug may be directly bound to each other via their own linker groups or indirectly via a linker or other substance.

A number of different reactions are available for covalent attachment of drugs to peptides. This is often accomplished by reaction of the amino acid residues of the peptide molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the peptide. Additionally, bifunctional agents such as dialdehydes or imidoesters have been used to link the amino group of a compound to amino groups of the peptide molecule. Also available for attachment of drugs to peptides is the Schiff base reaction. This method involves the periodate oxidation of a drug that contains glycol or hydroxy groups, thus forming an aldehyde which is then reacted with the peptide molecule. Attachment occurs via formation of a Schiff base with amino groups of the peptide molecule. Isothiocyanates can also be used as coupling agents for covalently attaching drugs to peptides. Other techniques are known to the skilled artisan and within the scope of the present invention.

There are many linking groups known in the art for making peptide-drug conjugates. A linker preferably comprises one or more functional groups that react with either or both of the peptide and the drug. Examples of functional groups include amino, carboxyl, mercapto, maleimide, and pyridinyl groups.

In one embodiment of the invention, a peptide is linked with a drug via a bifunctional crosslinking reagent. As used herein, a "bifunctional crosslinking reagent" refers to a reagent that possesses two reactive groups one of which is capable of reacting with a peptide, while the other one is capable of reacting with the drug to link the peptide with the drug, thereby forming a conjugate. Any suitable bifunctional crosslinking reagent can be used in connection with the invention, so long as the linker reagent provides for retention of the drug, e.g., cytotoxicity, and targeting characteristics of the peptide. Preferably, the linker molecule joins the drug to the peptide through chemical bonds, such that the drug and the peptide are chemically coupled (e.g., covalently bonded) to each other.

In one embodiment, the bifunctional crosslinking reagent comprises non-cleavable linkers. A non-cleavable linker is any chemical moiety that is capable of linking a drug to a peptide in a stable, covalent manner. Preferably, a non-cleavable linker is not cleavable under physiological conditions, in particular inside the body and/or inside a cell. Thus, non-cleavable linkers are substantially resistant to acid-induced cleavage, light-induced cleavage, peptidase-induced cleavage, esterase-induced cleavage, and disulfide bond cleavage, at conditions under which the drug or the peptide remains active. Suitable crosslinking reagents that form non-cleavable linkers between a drug and a peptide are well known in the art. In one embodiment, the drug is linked to the peptide through a thioether bond.

In one particularly preferred embodiment, the linking reagent is a cleavable linker. Preferably, a cleavable linker is cleavable under physiological conditions, in particular inside the body and/or inside a cell. Examples of suitable cleavable linkers include disulfide linkers, acid labile linkers, photolabile linkers, peptidase labile linkers, and esterase labile linkers.

Examples of linkers include, but are not limited to, N-succinimidyl-3-(2-pyridyldithio)butyrate (SPDB), N-succinimidyl-3-(2-pyridyldithio)propionate (SPDP), sulfosuccinimidyl-4-(N-maleimidomethyl)cyclohexane-1-carboxylate (Sulfo-SMCC), N-succinimidyl-4-(maleimidomethyl) cyclohexanecarboxylate (SMCC), N-succinimidyl-4-(N-maleimidomethyl)-cyclohexane-1-carboxy-(6-amidocaproate) (LC-SMCC), 4-maleimidobutyric acid N-hydroxysuccinimide ester (GMBS), 3-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl-4-(p-maleimidophenyl)-butyrate (SMPB), N-(p-maleimidophenypisocymate (PMPI), 6-maleimidocaproyl (MC), maleimidopropanoyl (MP), p-aminobenzyloxycarbonyl (PAB), N-succinimidyl-4-(2-pyridylthio)pentanoate (SPP), and N-succinimidyl (4-iodoacetyl) aminobenzoate (SIAB). A peptide linker such as valine-citrulline (Val-Cit) or alanine-phenylalanine (ala-phe) may also be used, and any of the aforementioned linkers may be used in adequate combination.

Disulfide containing linkers are linkers cleavable through disulfide exchange, which can occur under physiological conditions. In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene).

Acid labile linkers are linkers cleavable at acid pH. For example, certain intracellular compartments, such as endosomes and lysosomes, have an acidic pH (pH 4-5), and provide conditions suitable to cleave acid labile linkers. Acid labile linkers are relatively stable under neutral pH conditions, such as those in the blood, but are unstable at below pH 5.5 or 5.0. For example, a hydrazone, semicarbazone, thiosemicarbazone, cis-aconitic amide, orthoester, acetal, ketal, or the like can be used.

Photolabile linkers are useful at the body surface and in many body cavities that are accessible to light. Furthermore, infrared light can penetrate tissue.

Peptidase labile linkers can be used to cleave certain peptides inside or outside cells. In one embodiment, the cleavable linker is cleaved under mild conditions, i.e., conditions within a cell under which the activity of the cytotoxic agent is not affected.

The linker can be or can comprise, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a valine-citrulline (Val-Cit; vc) linker or a phenylalanine-lysine (Phe-Lys) linker. One advantage of using intracellular proteolytic release of the therapeutic agent is that the agent is typically attenuated when conjugated and the serum stabilities of the conjugates are typically high.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing Fibronectin Extra Domain B.

"Diseases involving cells expressing Fibronectin Extra Domain B" or similar expressions means according to the invention that Fibronectin Extra Domain B is expressed by cells of a diseased tissue or organ. In one embodiment, expression of Fibronectin Extra Domain B by cells of a diseased tissue or organ is increased compared to the state in a healthy tissue or organ. In one embodiment, expression is only found in a diseased tissue, while expression in a healthy tissue is repressed. According to the invention, diseases involving cells expressing Fibronectin Extra Domain B include cancer diseases. Furthermore, according to the invention, cancer diseases preferably are those wherein cells express Fibronectin Extra Domain B.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by expression or presence of Fibronectin Extra Domain B.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant. According to the invention, a "cancer disease" preferably is a "tumor disease". However, generally, the terms "cancer" and "tumor" are used interchangeably herein.

Preferably, a tumor disease according to the invention is a cancer disease, i.e. a malignant disease, and a tumor cell is a cancer cell. Preferably, a tumor disease or cancer disease is characterized by the presence of Fibronectin Extra Domain B. In one embodiment, a cancer is a Fibronectin Extra Domain B-positive cancer.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably. For example, a subject at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

A (therapeutic) treatment of cancer may be selected from the group consisting of surgery, chemotherapy, radiation therapy and targeted therapy.

The term "surgery", as used herein, includes the removal of tumors in an operation. It is a common treatment for cancer. A surgeon may remove the tumors using local excision.

The term "chemotherapy", as used herein, refers to the use of chemotherapeutic agents or combinations of chemotherapeutic agents, preferably to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy).

Chemotherapeutic agents according to the invention include cytostatic compounds and cytotoxic compounds. Traditional chemotherapeutic agents act by killing cells that divide rapidly, one of the main properties of most cancer cells. This means that chemotherapy also harms cells that divide rapidly under normal circumstances such as cells in the bone marrow, digestive tract, and hair follicles. This results in the most common side-effects of chemotherapy. Agents that target proteins that are abnormally expressed in a cancer (such as Fibronectin Extra Domain B) and act through a therapeutic moiety or agent conjugated to the agent can be viewed as a form of chemotherapy. However, in the strictest sense, the term "chemotherapy" according to the invention does not include targeted therapy.

According to the invention, the term "targeted therapy" relates to any therapy that can be used to target preferentially diseased organs, tissues or cells such as cancer tissues or cells while non-diseased organs, tissues or cells are not targeted or targeted to a lesser extent. Targeting of diseased organs, tissues or cells preferably results in killing and/or impairment of proliferation or viability of diseased cells.

Such therapy includes i) agents that are conjugated to a therapeutic moiety that target certain targets, for example, Fibronectin Extra Domain B, to deliver the therapeutic moiety (e.g. Fibronectin Extra Domain B binding agents conjugated to a therapeutic moiety) or ii) agents that target certain targets, for example, Fibronectin Extra Domain B, and impair proliferation, spread, migration and/or or viability of diseased cells, (e.g. Fibronectin Extra Domain B binding agents conjugated to a therapeutic moiety or not conjugated to a therapeutic moiety).

The pharmaceutical compositions and methods of treatment described according to the invention may be used to therapeutically treat or prevent a disease described herein. It is possible to use animal models for testing an effect on cancer. For example, human cancer cells may be introduced into a mouse to generate a tumor. The effect on the cancer cells (for example reduction in tumor size) may be measured as a measure for the effectiveness of an agent administered to the animal.

Peptides may be administered in a manner known per se. Generally, doses of a peptide of from 1 ng to 1 mg, preferably from 10 ng to 100 µg, are formulated and administered.

If the administration of nucleic acids (DNA and RNA) is desired, doses of from 1 ng to 0.1 mg may be formulated and administered.

In one embodiment, nucleic acids are administered by ex vivo methods, i.e. by removing cells from a patient, genetic modification of said cells in order to incorporate a nucleic acid and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker.

The invention also provides for administering nucleic acids in vivo by using, for example, vectors such as viruses and target-controlled liposomes.

In a preferred embodiment, a virus or viral vector for administering a nucleic acid is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutically active compounds of the invention may be administered via any conventional route, including by injection or infusion. The administration may be carried out, for example, orally, intravenously, intraperitonealy, intramuscularly, subcutaneously or transdermally. Administration can be locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

An injectable formulation may comprise a pharmaceutically acceptable excipient such as Ringer Lactate.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavouring agents, or colorants.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders characterized by an altered expression pattern of Fibronectin Extra Domain B.

For example, in one embodiment, agents described herein can be used to treat a patient with a cancer disease, e.g., a cancer disease such as described herein characterized by the presence of Fibronectin Extra Domain B.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: A: Analytical SDS-PAGE of FN-proteins after IMAC and SEC purification. A total of 10 μg protein was applied to SDS-PAGE under reducing (+β-mercaptoethanol)

and non-reducing (-β-mercaptoethanol) conditions. Protein batch purity was furthermore determined via densitometric analysis using ImageQuant software from unmodified SDS-PAGE image. Contrast and brightness have been altered in this image for better visualization. B: Enzyme linked immunosorbent assay (ELISA)-based binding analysis of FN-6789, FN-67B89 and FN-B with anti-His- and BC-1 antibody. Error bars represent standard deviations resulting from duplicate measurements, with 1 µg proteins coated per well respectively.

FIG. 2: Enriched cystine-knot miniprotein sequences after three phage screening rounds of MCopt 1.0 and MCopt 2.0 libraries. Clone name, cystine-knot miniprotein sequence and proportion of total screen clones are depicted for each candidate. Variable amino acids are shown in bold letters. The identified common R-I/V-R-(L) motif is highlighted in grey (from top to bottom: SEQ ID NOs: 7, 8, 9, 10, 11 and 12).

FIG. 3: EDB binding cystine-knot miniproteins resulting from phage display screening of MCopt 1.0 library and following hit identification process. Ranking values were calculated on the basis of the signal (FN-B) to noise (BSA) ratios determined via ELISA and were further normalized to the expression rate of Trx-cystine-knot miniproteins. Variable amino acids are shown in bold letters (from top to bottom: SEQ ID NOs: 10, 7 and 11).

Figure 4:
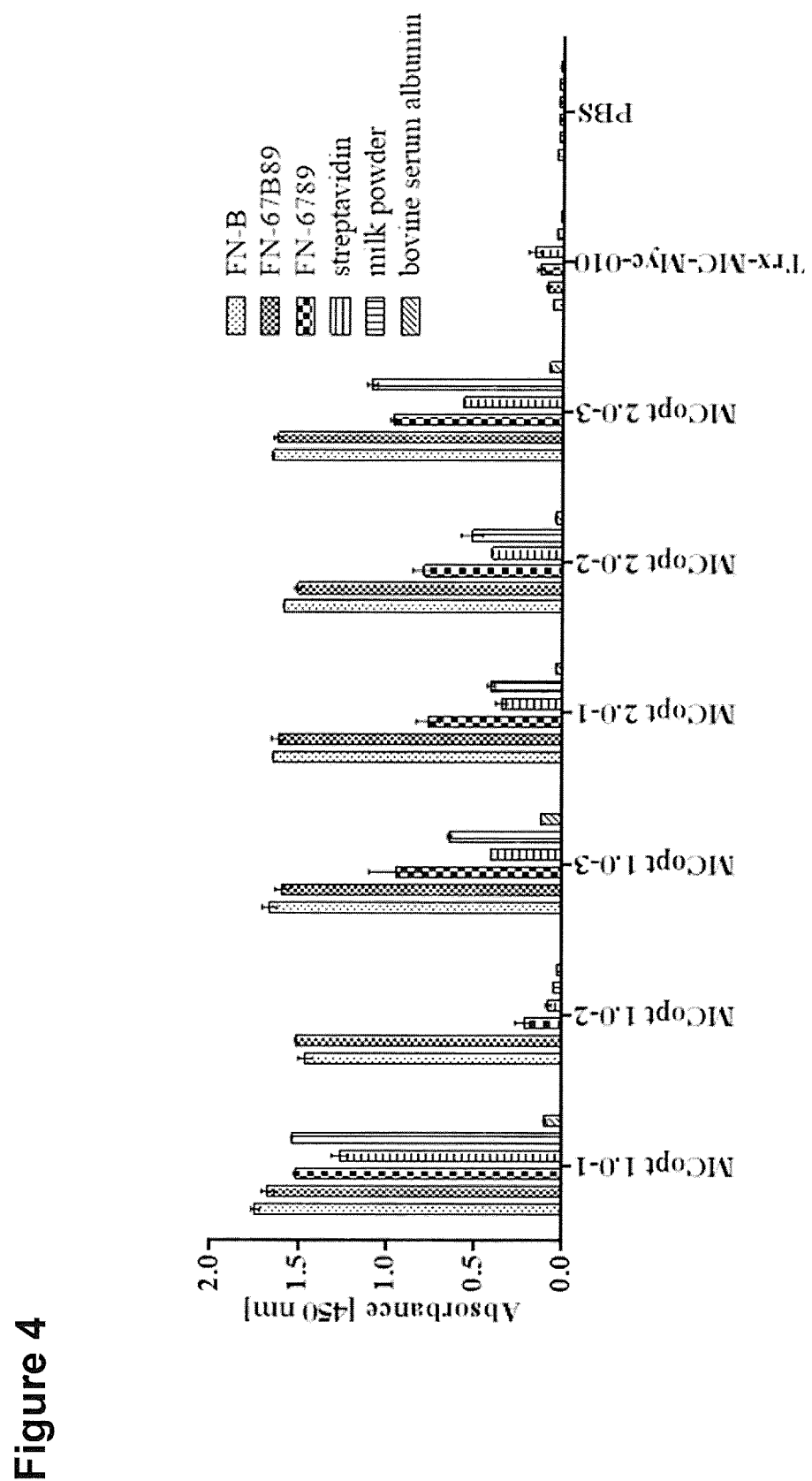

FIG. 4: Specificity analysis of Trx-cystine-knot miniprotein clones MCopt 1.0-1/-2/-3 and MCopt 2.0-1/-2/-3. 200 nM of each variant were applied to immobilized FN-B and FN-67B89 target proteins as well as to control proteins FN-6789, milk powder and bovine serum albumin (coated at 1 µg/well). An HRP-conjugated anti-s-tag antibody was used to analyze binding. ELISA was performed in duplicates with Trx-MC-Myc-010 serving as negative control.

Figure 5:
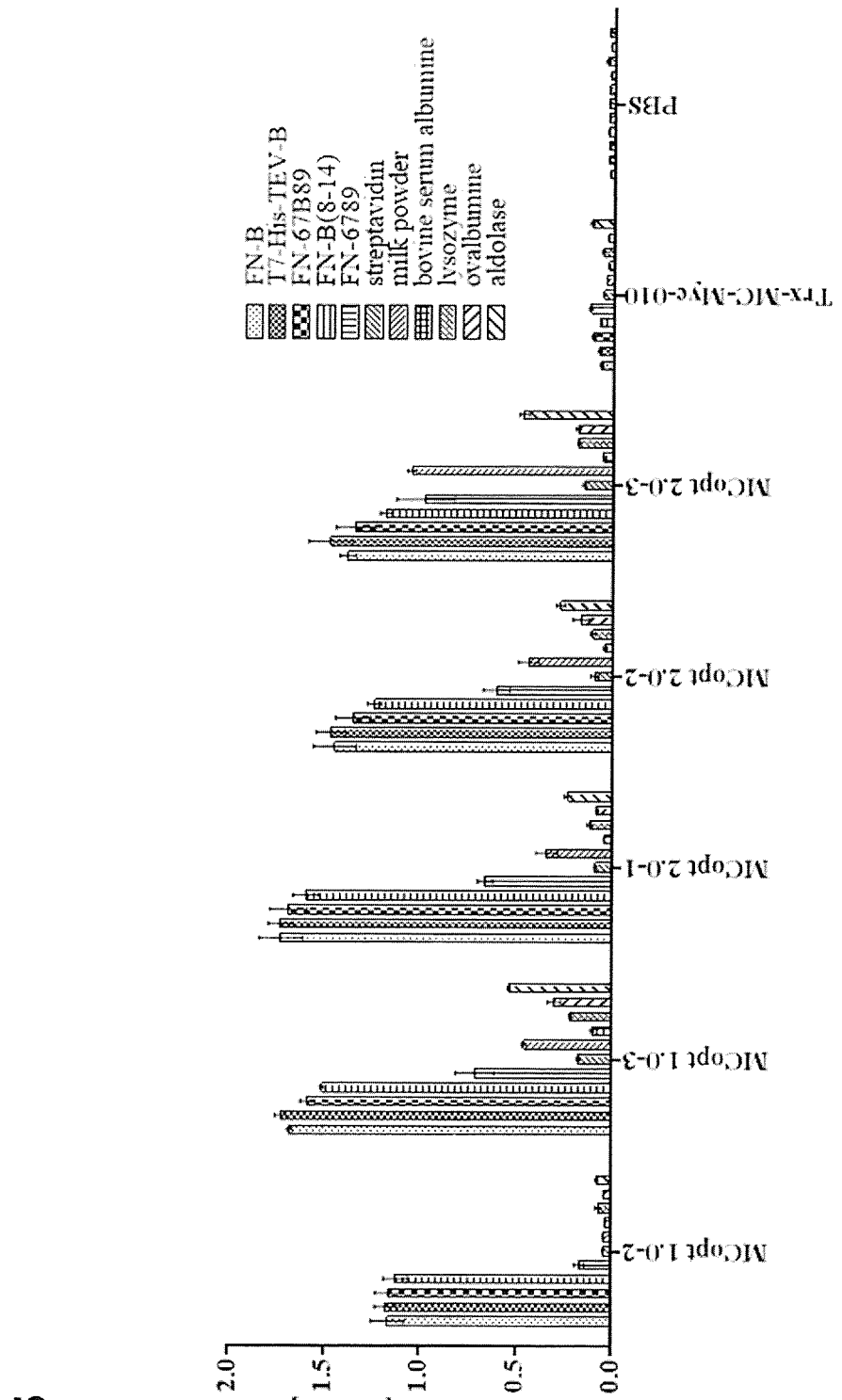

FIG. 5: Extended specificity analysis of Trx-cystine-knot miniprotein clones MCopt 1.0-2/-3 and MCopt 2.0-1/-2/3. In total 200 nM of each variant were applied to FN-B, T7-TEV-B, FN-67B89 and FN-B(8-14) target proteins as well as negative controls FN-6789, milk powder, bovine serum albumin, lysozyme, ovalbumin and aldolase (coated at 1 µg/well). ELISA was performed in duplicates, error bars represent standard deviation and Trx-MC-Myc-010 served as negative cystine-knot miniprotein control.

Figure 6:
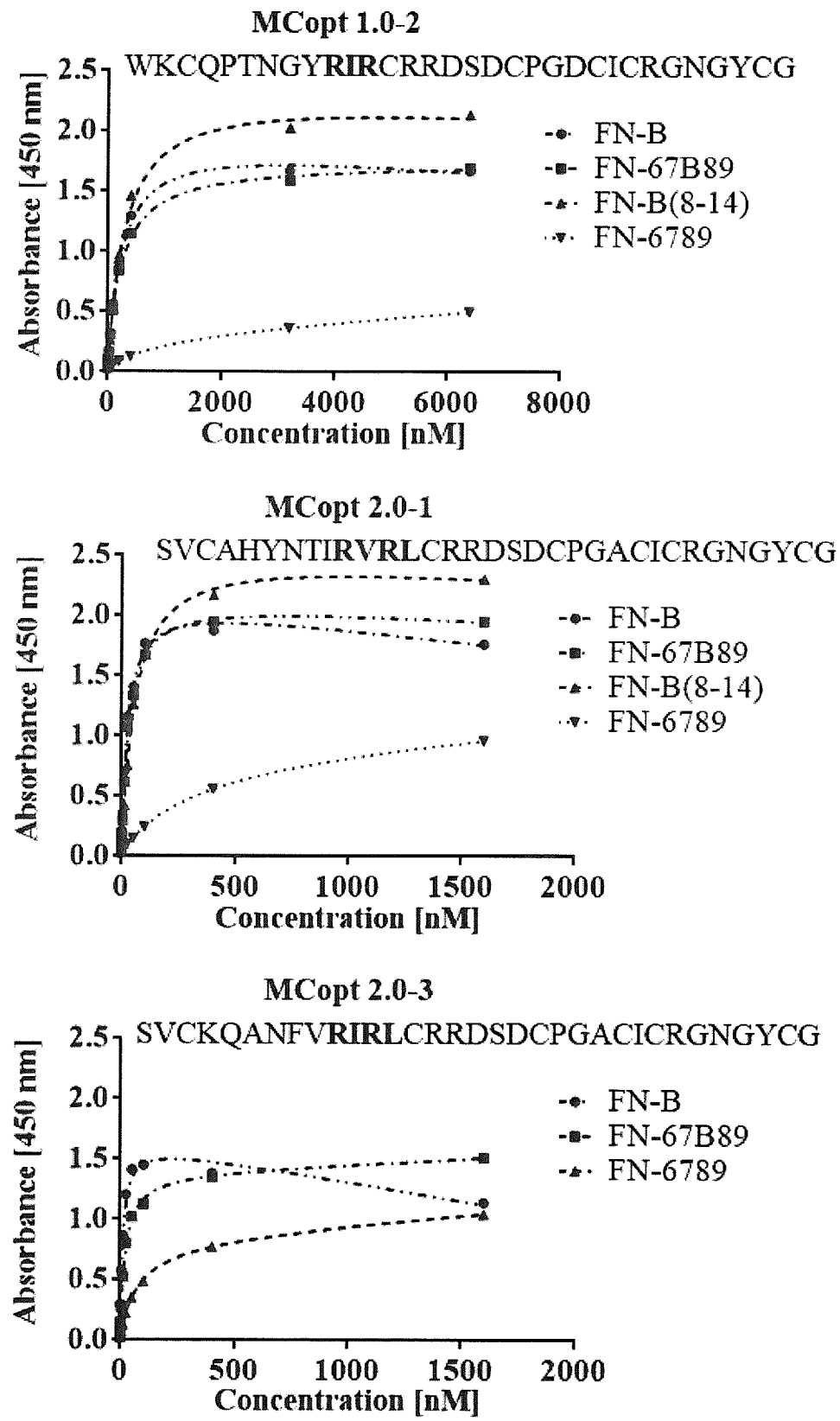
Figure 6:
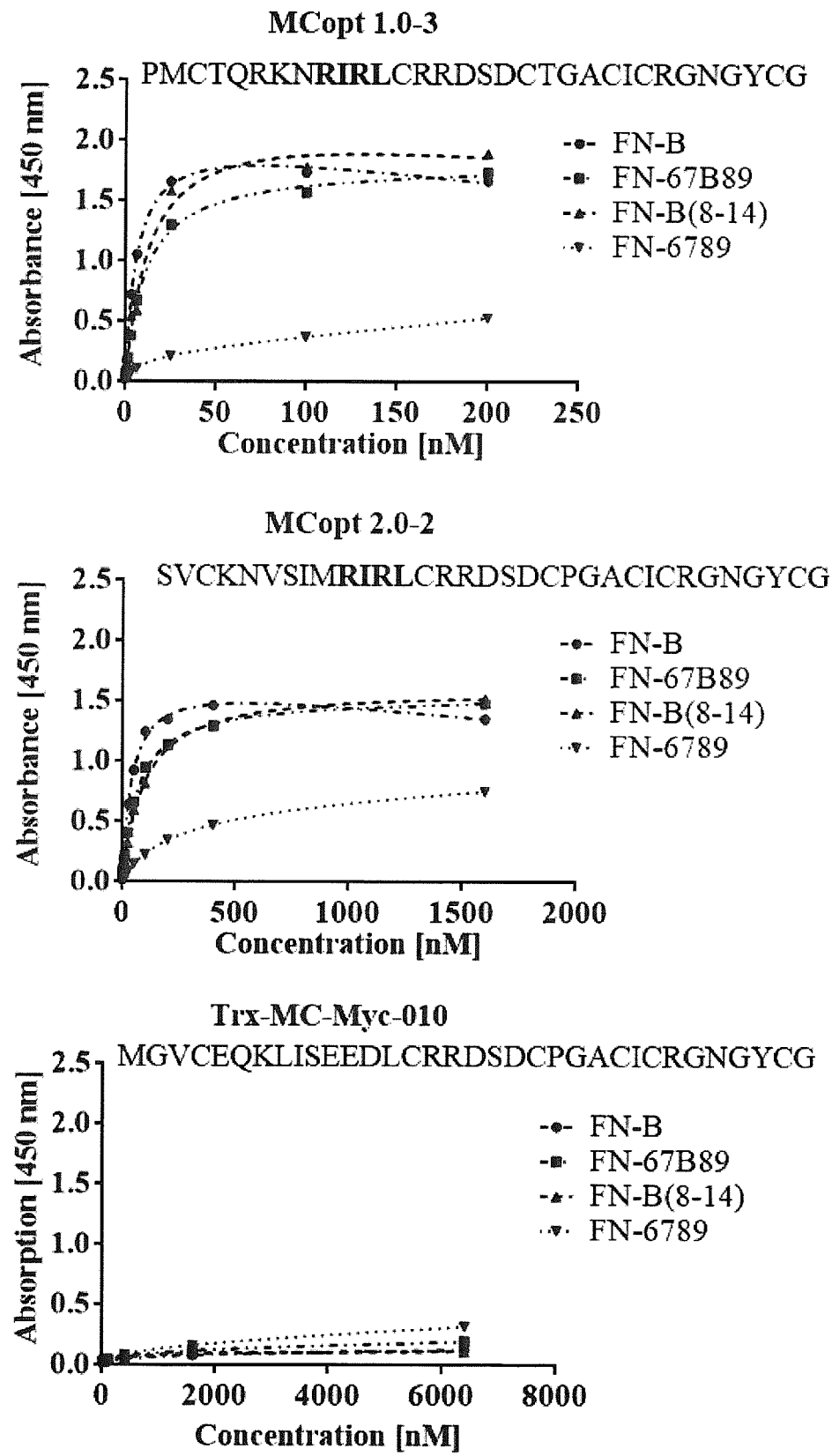

FIG. 6: Saturation-binding curves of MCopt 1.0-2/-3 and MCopt 2.0-1/-2/-3 EDB binding. Trx-cystine-knot miniprotein binding was assayed against FN-B, FN-67B89 and FN-B(8-14) targets as well as against FN-6789 control protein (coated at 1 µg/well) in ten different concentrations. Binding of Trx-cystine-knot miniproteins was detected with an HRP-conjugated anti-s-tag-antibody. ELISAs were performed in duplicates (single values for FN-B(8-14)). Left: from top to bottom SEQ ID NOs: 7, 8, and 12; and right from top to bottom SEQ ID NOs: 11, 8, and 29.

Figure 7:

FIG. 7: A: Respective amino acids in the first, second or fifth loop of parental MC-FN-010 sequence were exchanged with alanine. Alanine substitutions are highlighted in grey (from top to bottom: SEQ ID NOs: 11, 13, 14, 15, 16, 17, 18, 19, 20, 21, 22, 23, 24, 25, and 26). B: Parental MC-FN-010 and alanine scan variants as Trx-fusion proteins (50 nM to 1.563 nM) were incubated with pre-coated human FN-B. Binding was detected with 10 ng of HRP-conjugated anti-s-tag-antibody. ELISA was performed in duplicates and in three independent assays. Relative binding of each variant was calculated by determination of apparent binding constants and comparison to parental MC-FN-010. Error bars represent the standard deviation of three duplicate measurements. C: Sequence of parental MC-FN-010 (SEQ ID NO: 11). Bold letters and brackets indicate the amino acid cysteine and the disulfide bond connectivity. Residues highlighted in light grey are relevant for target-binding, those that are marked in grey do not contribute in binding interaction or only to a minor extend.

Figure 8:
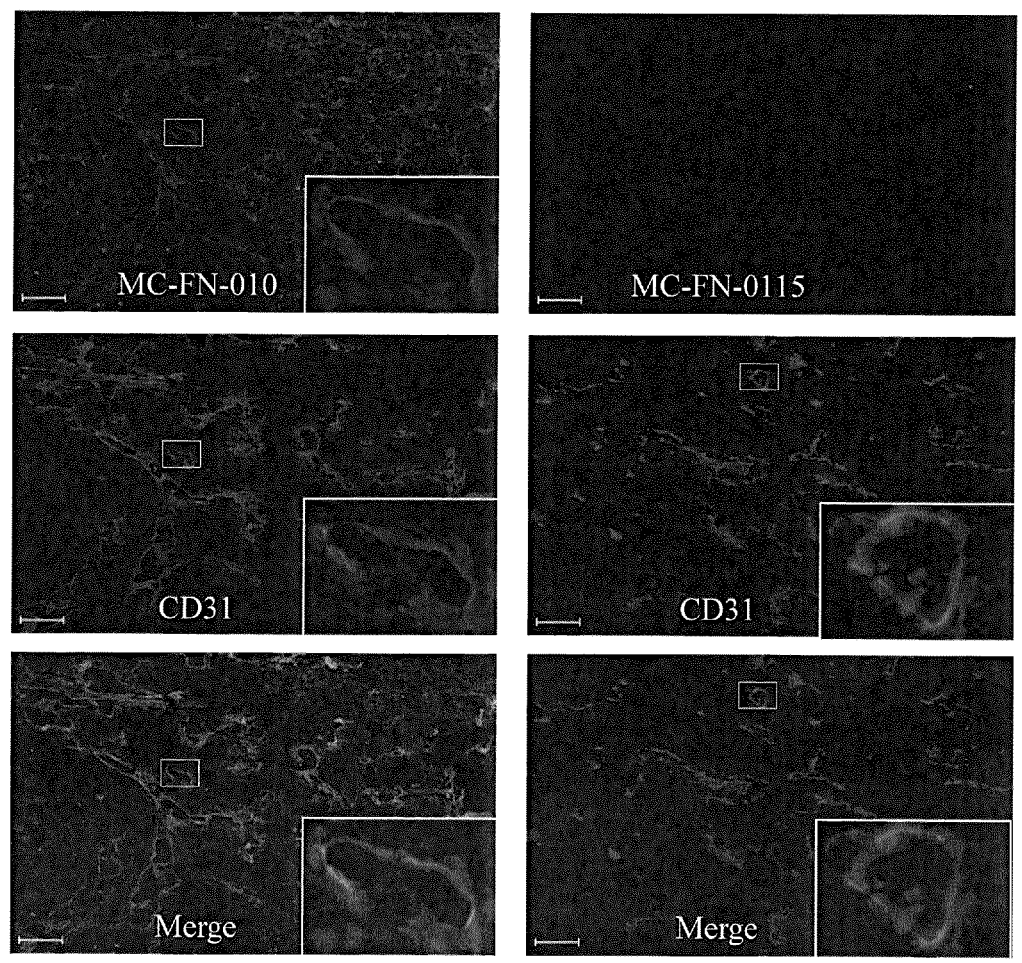

FIG. 8: Specific binding of MC-FN-010 to glioblastoma xenograft tumor sections. Representative results of immunofluorescence staining of U-87 MG tumor tissues with EDB ligand MC-FN-010 and negative control MC-FN-0115. The tissue sections (5 µm) were stained with tetramerized cystine-knot miniprotein-biotin strepatividin-Cy3 complex (red) and with an anti-CD31 antibody to visualize vasculature (green). Scale bars indicate 100 µm.

Figure 9:
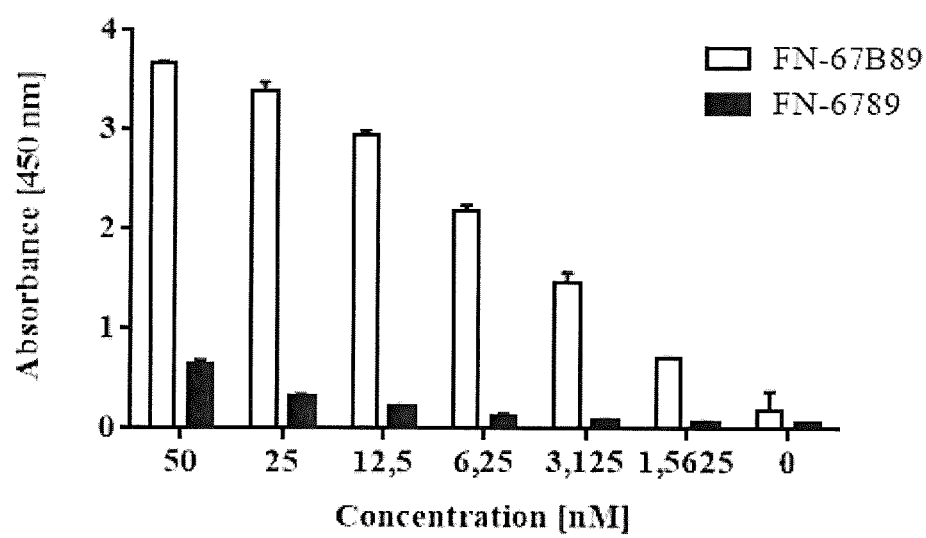
Figure 9:
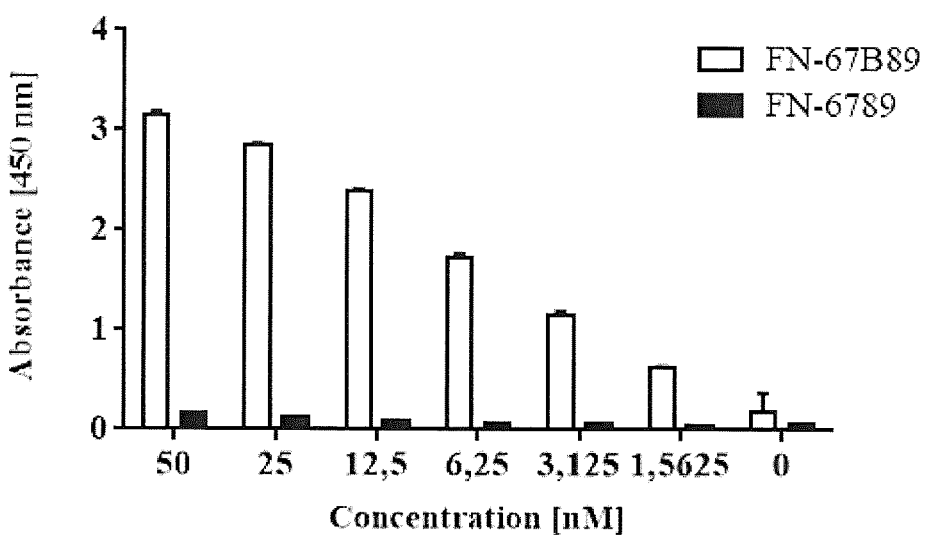

FIG. 9: A: Specificity analysis of Trx-MC-FN-010 to human FN-67B89 and FN-6789 using ELISA. B: Specificity analysis of Trx-MC-FN-016 to human FN-67B89 and FN-6789 using ELISA. Binding of Trx-MC-FN-010 and Trx-MC-FN-016 to FN-67B89 with concentrations ranging from 1.56-50 nM in comparison to FN-6789 was detected with 50 ng of HRP-conjugated anti-S-tag-antibody. ELISA was performed in duplicates using 1 µg coated FN-67B89 or FN-6789 per well.

FIG. 10: A: Kinetic parameters of MC-FN-010 and MC-FN-016 resulting from 5 surface plasmon resonance analysis. Biotinylated human FN-67B89 was immobilized to streptavidin sensor to perform affinity determination of MC-FN-010 and MC-FN-016 using two-fold serial dilutions starting from 4000 nM. Kinetic parameters were calculated using a 1:1 Langmuir fitting model applied to generated sensorgrams. B: Kinetic parameters of AF680-(MC-FN-010)$_3$ and AF680-(MC-FN-016)$_3$ resulting from surface plasmon resonance with single cycle kinetic analysis. Biotinylated human FN-67B89 was immobilized to streptavidin chip to perform binding determination of AF680-(MC-FN-010)$_3$ and AF680-(MC-FN-016)$_3$ using two-fold serial dilution starting from 10 nM. Kinetic parameters were calculated using a 1:1 Langmuir fitting model applied to generated sensorgrams.

Figure 11:
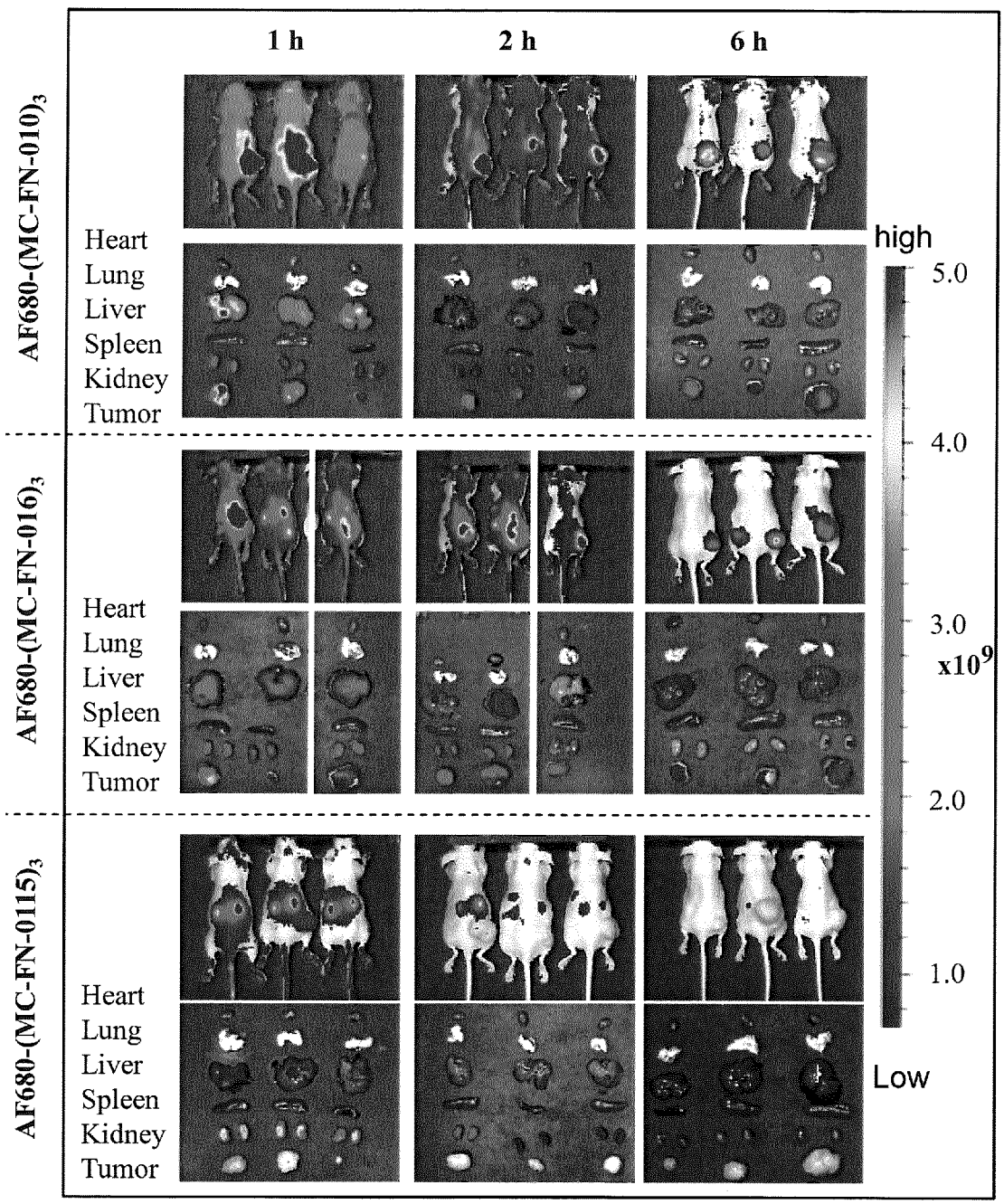
Figure 11:
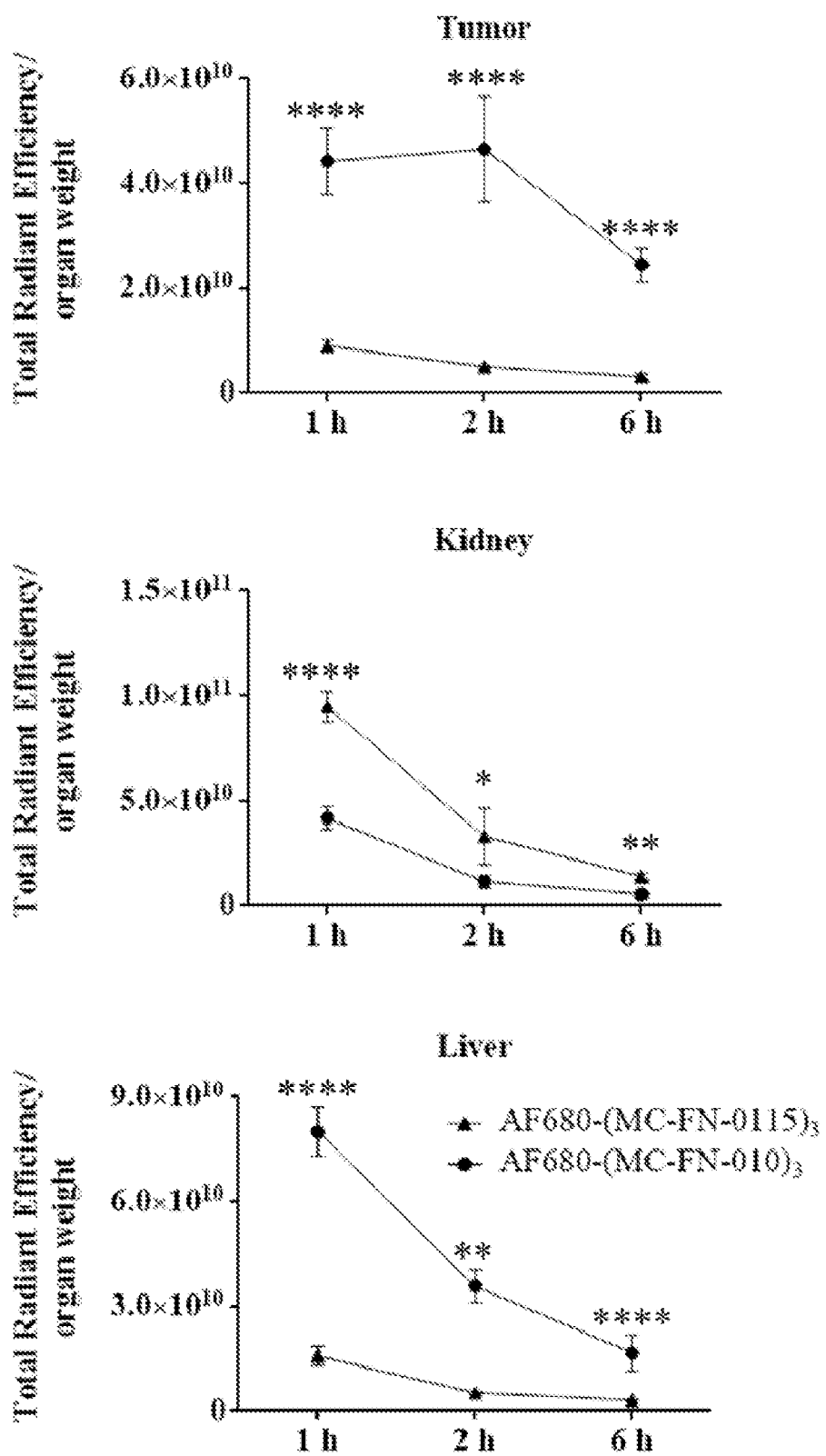
Figure 11:
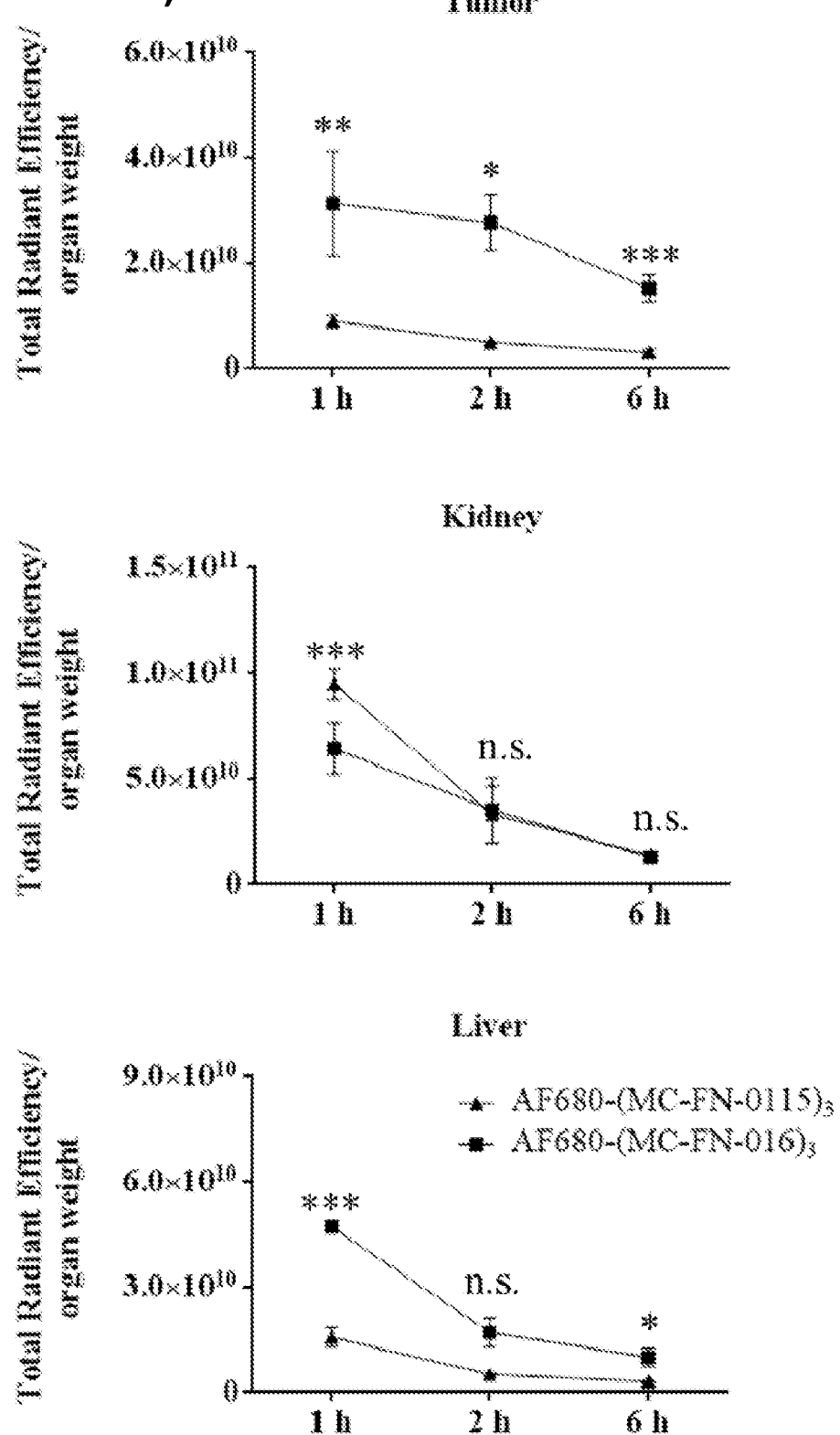

FIG. 11: A: In vivo and ex vivo imaging of U-87 MG bearing mice. Mice with tumors arising from s.c. injected human U-87 MG cells were imaged after i.v. application of 3.36 nmol AF680-(MC-FN-010)$_3$, AF680-(MC-FN-016)$_3$ (EDB binder) and control AF680-(MC-FN-0115)$_3$. Groups were stratified with three mice per group, each carrying a different tumor size. Imaging was performed 1 h, 2 h and 6 h post injection. After in vivo imaging organs and tumors were excised, weighed and used for ex vivo fluorescence signal analysis. B: Development of fluorescence signals over time in tumor, kidney, liver and lung. Fluorescence signals of organs were quantified using Living Image 2.5 imaging analysis software and normalized to the respective organ/tumor weight. Mean of data sets are shown resulting from triplicates ±SE. Statistical significance was calculated with two-way ANOVA (*P<0.0342; P<0.0055; *P=0.0001; ****P<0.0001; n. s.=not significant).

Figure 12:
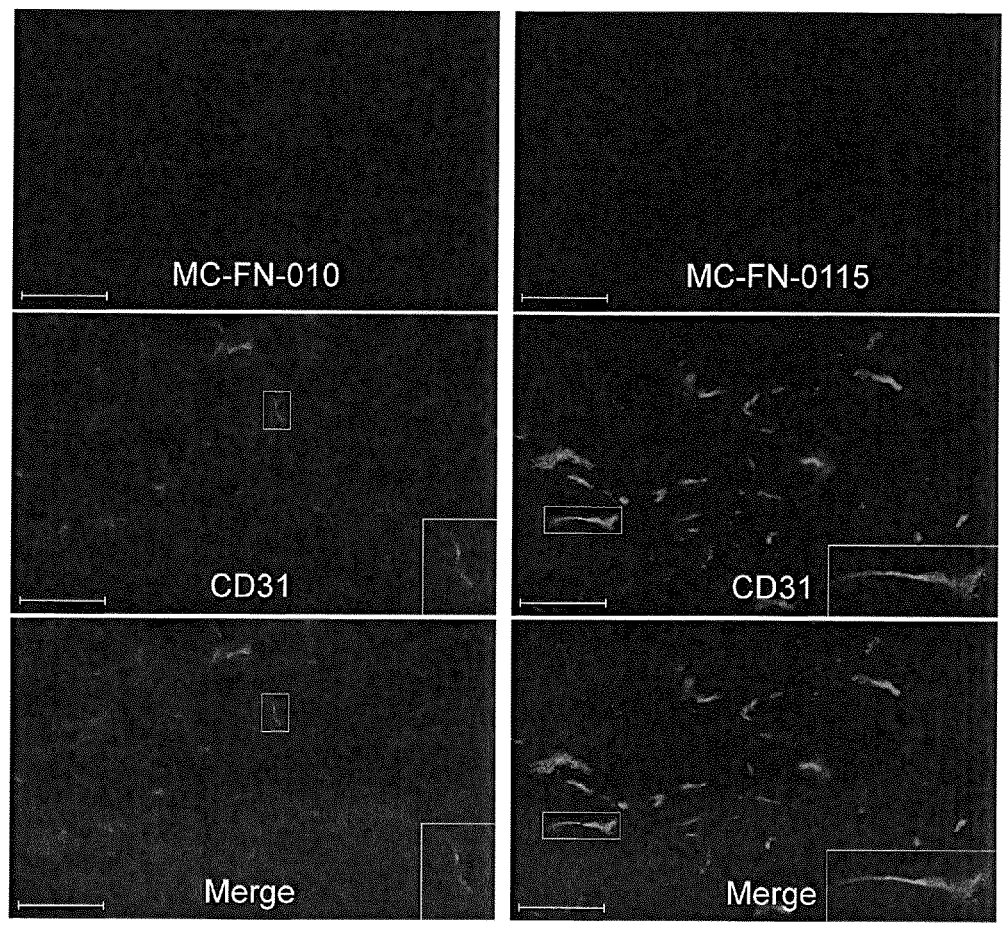

FIG. 12: Representative immunofluorescence staining of normal mouse brain with EDB ligand MC-FN-010 and negative control MC-FN-0115. Tissue sections (6 µm) were stained with tetramerized cystine-knot miniprotein-biotin/strepatividin-Cy3 complex and an anti-CD31 antibody to visualize vasculature. Scale bars, 100 µm.

Figure 13:
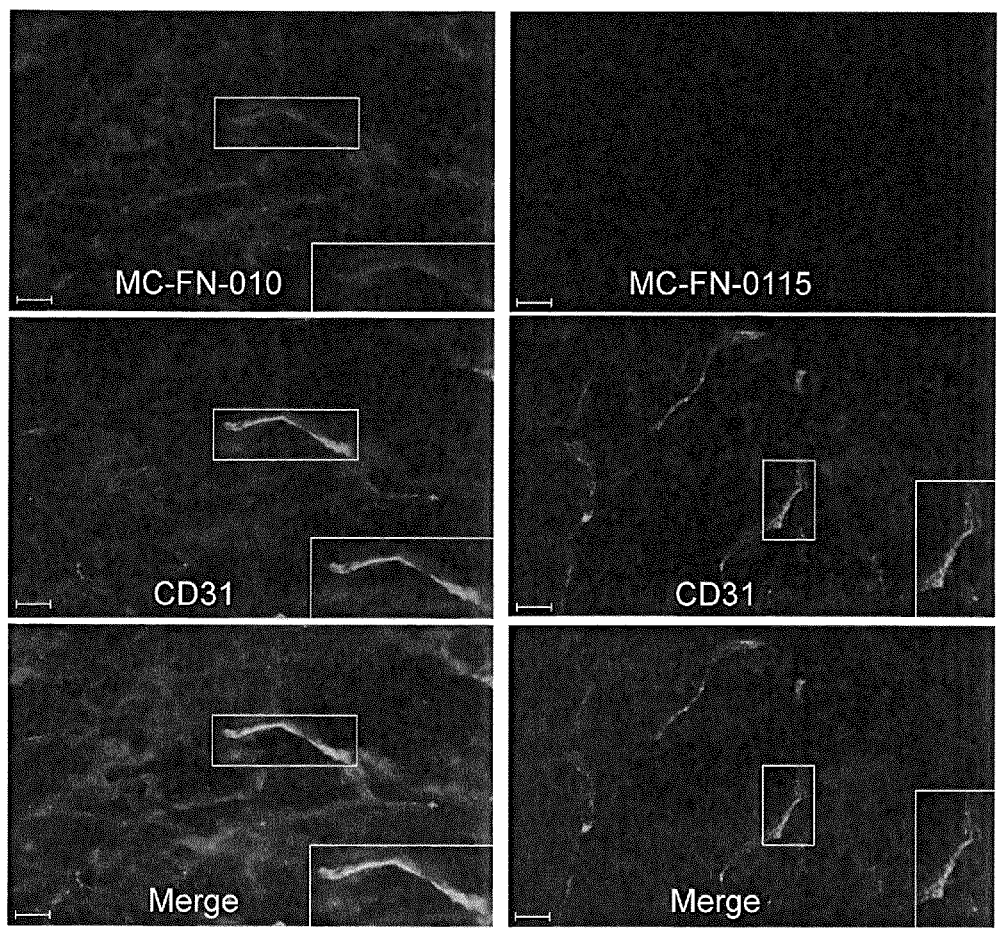
Figure 13:
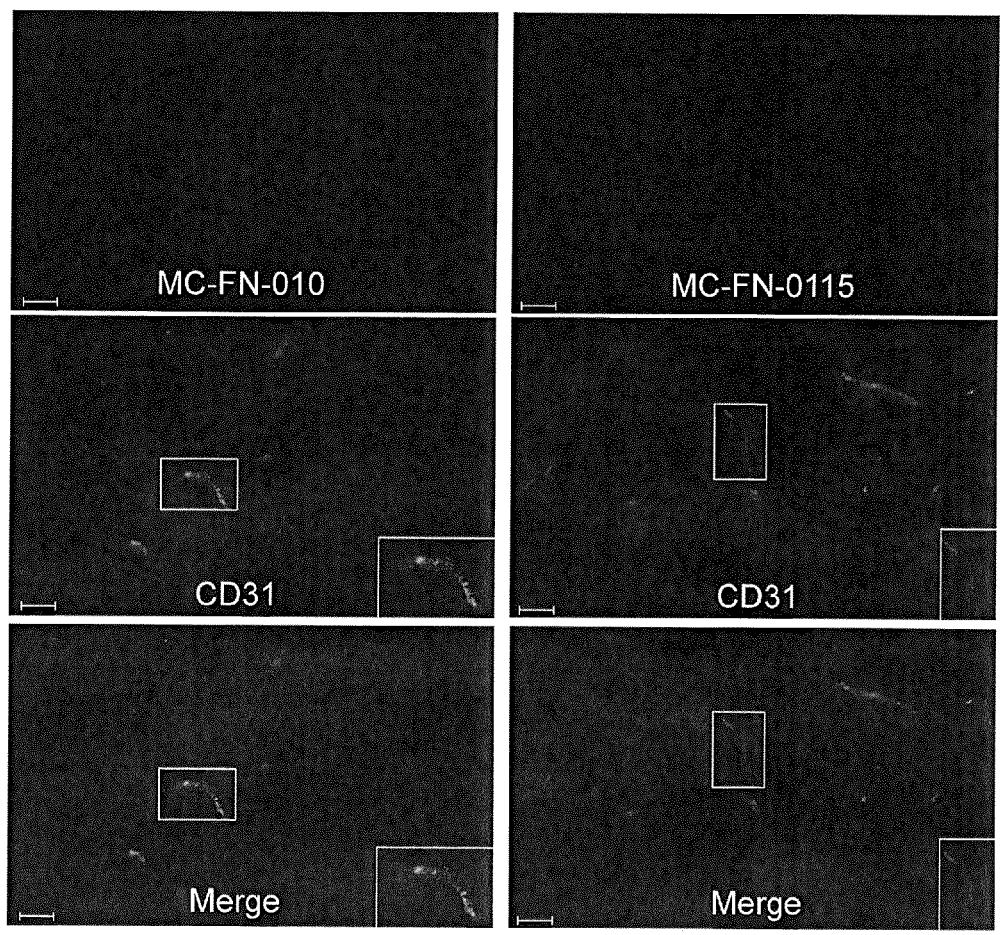

FIG. 13: Specific binding of MC-FN-010 to tissue sections derived from the human U-87 MG glioblastoma cell line grown as mouse xenograft tumor. Representative immunofluorescence staining of U-87 MG tumor tissues (A) and normal mouse brain (B) with trimeric MC-FN-010 and negative control MC-FN-0115. Tissue sections (6 µm) were stained with Alexa Fluor 680 conjugated trimeric cystine-knot miniproteins and an anti-CD31 antibody detected with a secondary antibody to visualize vasculature. Scale bars, 20 µm.

Figure 14:
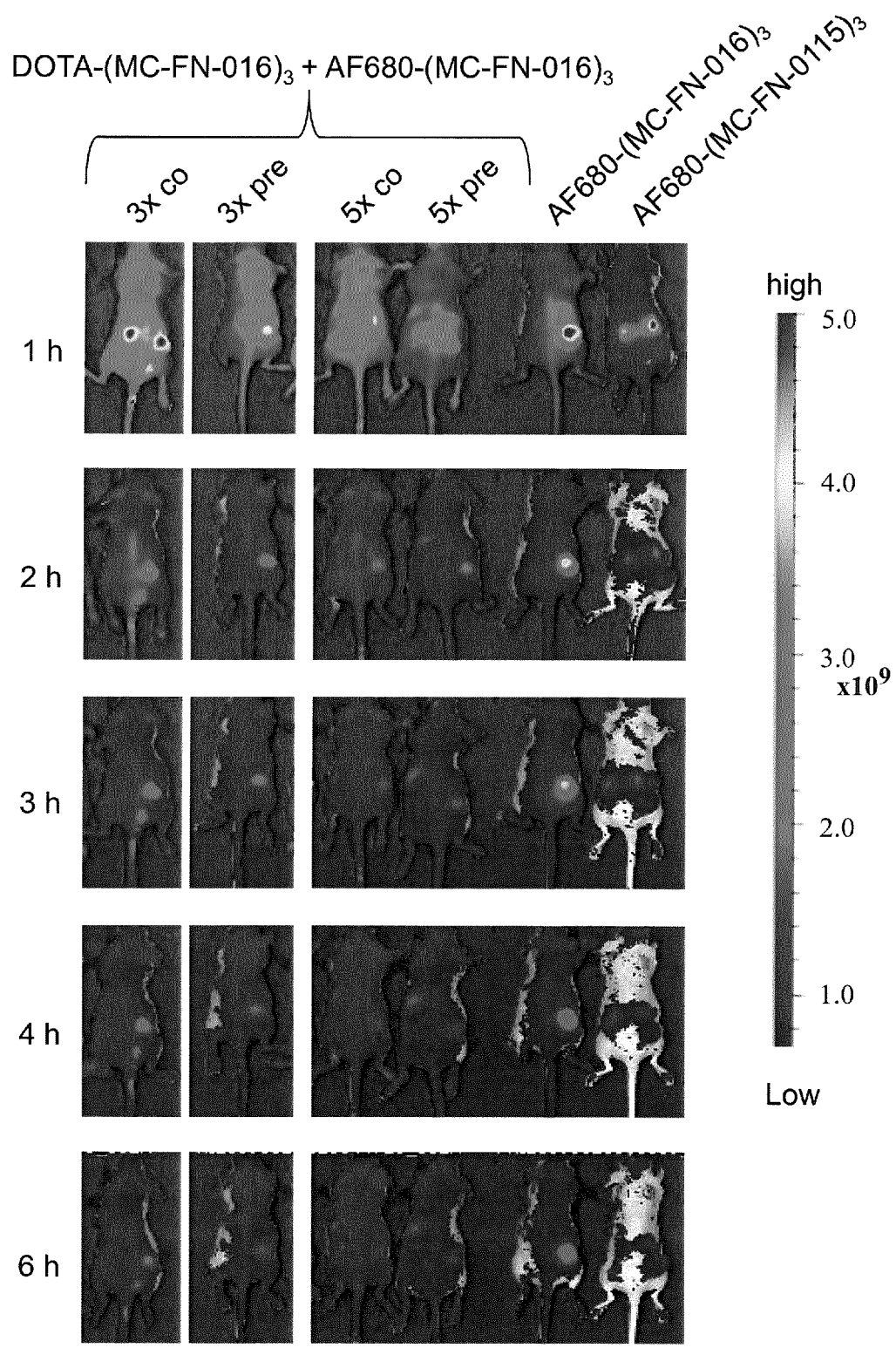
Figure 14:
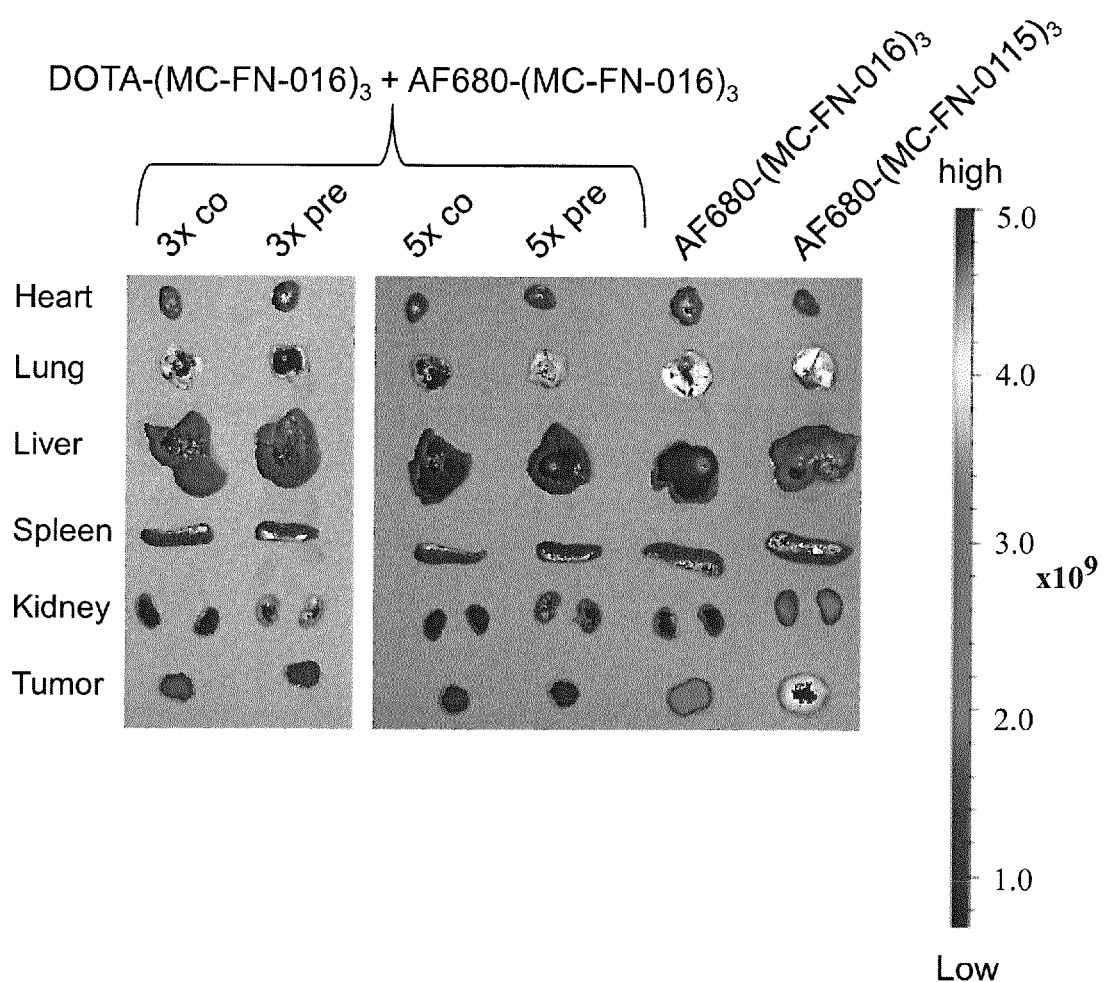
Figure 14:
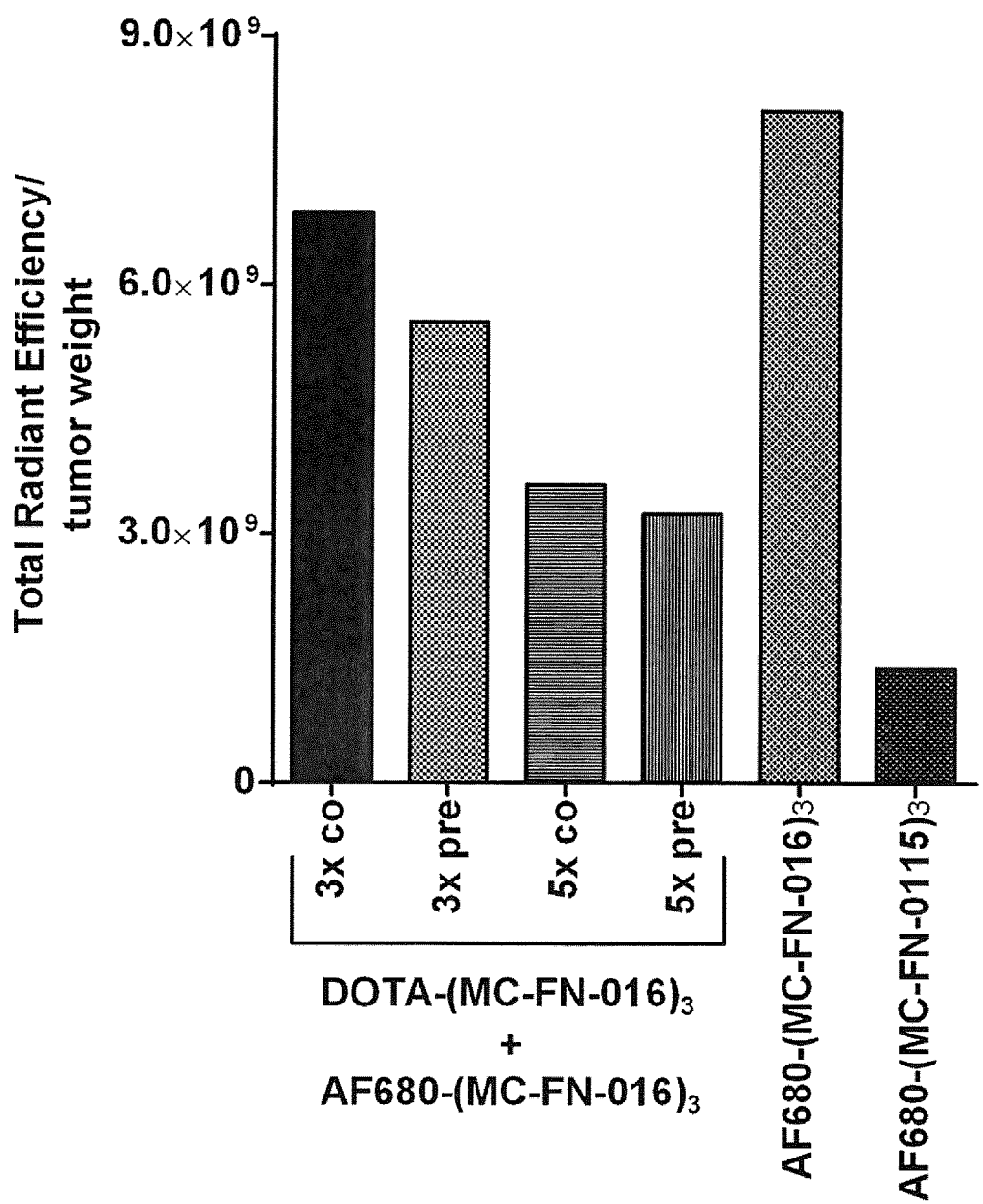

FIG. 14: A: In vivo imaging of U-87 MG bearing mice. Tumors derived from human U-87 MG cells injected s.c. in flanks of Fox n1/nu mice were subjected to imaging after i.v. application of 3.34 nmol AF680-(MC-FN-016)$_3$ alone, or in combination with a 3- and 5-fold molar excess of DOTA-(MC-FN-016)$_3$ injected concurrently (co-injection) or 30 min prior to it (pre-injection). Triple alanine-mutant peptide AF680-(MC-FN-0115)$_3$ served as a negative control. B: Imaging of organs 6 h after i.v. injection of the probes. C: Fluorescence signals in tumors were quantified and normalized to the respective tumor weight.

FIG. 15: SPR binding analysis of cystine-knot miniprotein variants to EDB. Kinetic parameters of EDB-specific cystine-knot miniprotein variants as measured by surface plasmon resonance analysis and calculated using a 1:1 Langmuir fitting model. Biotinylated human FN-67B89 was immobilized to a streptavidin sensor to determine affinity of DOTA-(MC-FN-016)$_3$ using two-fold serial dilutions.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1: Material and Methods

Target Expression, Purification and Biotinylation

Recombinant human fibronectin EDB either as a single domain (FN-B, Uniprot ID P02751, isoform 7, amino acid E1265-T1355) or flanked by its surrounding type III domains (FN-67B89, amino acid G1080-E1455) served as target protein in this study while domains 6-9 without EDB (FN-6789) was used as control. All variants were expressed in *E. coli* with a c-terminal hexahistidine (H6) tag and purified via immobilized metal ion affinity chromatography (IMAC) and size exclusion chromatography (SEC). For this, codon-optimized DNA sequences were synthesized by Thermo Fisher Scientific, cloned into pET-21a expression vector 5 (Novagen) and introduced into *E. coli* BL21 (DE3) cells (Agilent). Proteins were expressed in a 750-mL scale at 30° C., 120 rpm until an OD$_{600}$ of approximately 0.7 was reached. For induction of protein production, 750 µL 1 M IPTG were added to the main-culture and incubated at 25° C., 120 rpm overnight. Cells were harvested, re-suspended in 10 mL equilibration buffer (20 mM Tris-HCl pH 8.0, 10% glycerol, 500 mM NaCl, 10 mM imidazole) and lysed by sonication (Branson Digital Sonifier 250). The supernatant was purified by IMAC with a 1 mL HisTrap column (GE Healthcare) using an ÄKTAprime™ plus system (GE Healthcare) and a linear gradient from 10-500 mM imidazole in 20 min. Subsequently, proteins were dialyzed against PBS (14 mM NaCl, 2.7 mM KCl, 10 mM Na$_2$HPO$_4$, 1.8 mM KH$_2$PO$_4$, pH 7.5) at 4° C. overnight and further purified by size exclusion chromatography using a HiLoad 26/600 Superdex 200 µg (for FN-67B89 and FN-6789) or 75 µg (for FN-B) column (GE Healthcare). Final purified proteins were analyzed via SDS-PAGE, analytical SEC and via ELISA using the EDB specific BC-1 antibody (ab154210, Abcam). Proteins were stored in aliquots in PBS supplemented with 5% mannitol and 5% trehalose at −20° C. FN-B, FN-67B89 and FN-6789 proteins were biotinylated via primary NH2-groups using EZ-Link Sulfo-NHS-LC-Biotin (Thermo Fisher Scientific) according to manufacturer's introductions.

Quality Control of FN-67B89 Target Protein

To determine the quality of expressed and purified FN-67B89 protein, ELISA was used as technique to analyze protein-protein interactions in a 96-well format. In a first step, 10 µg/mL target proteins were coated on a Maxisorb™ 96-well plate in a volume of 100 µL via passive absorption under alkaline conditions, using 50 mM Na$_2$CO$_3$ pH 9.4 coating buffer. Coating of ELISA plates was performed overnight at 4° C. After removal of coating buffer the plates were washed three times with 300 µL PBS-T and 300 µL blocking buffer (3% BSA in PBS) was added. Blocking was performed for 2 h at RT. For primary incubation, plates were washed three times with 300 µL PBS-T and incubated for 1 h with 100 µL of BC-1 antibody diluted 1:1000 in PBS-T, at 4° C. A HRP-conjugated anti-mouse antibody (554002, BD Pharmingen™) diluted 1:5000 in PBS was added after washing three times with PBS-T in 100 µL/well and incubated for 1 h at 4° C. Plates were then washed three times with PBS-T and three times with PBS prior to detection of antigen-antibody complexes via HRP mediated conversion of TMB substrate. 100 µL TMB substrate was added to the wells and a blue color developed in proportion to the amount of analyte present in the sample. Color development was stopped by adding of 50 µL 0.2 M HCl and the specific absorbance was measured at 450 nm.

Selection of EDB-Specific Ligands Via Phage Display

EDB-specific cystine knot miniproteins were selected via phage display using two different combinatorial libraries which are based on an open chain variant of the trypsin inhibitor II from *Momordica cochinchinensis* (oMCoTI-II). Both libraries are based on an M13 phagemid system but differ with respect to the applied randomization scheme. While in the MCopt1.0 library loop one (including a length variation of 6, 9 and 12 amino acids) and three as well as the two amino acids at the N-terminus have been randomized, the MCopt2.0 library was built via randomization of loop 1 with 10 amino acids only. Additionally, they are also different in the type of display as MCopt1.0 is presented via major coat protein pVIII and MCopt2.0 via pIII.

In total three screening rounds based on streptavidin-coated (SA) magnetic beads were performed with each library. For a screening round 2×50 µL Dynabeads® M-280 Streptavidin (Life Technologies) were transferred to a 2 mL tube each and washed with 1 mL TBS-T (50 mM Tris, 150 mM NaCl, 0.1% Tween-20, pH 7.4). 100 µg biotinylated FN-B in 200 µL TBS (50 mM Tris, 150 mM NaCl, pH 7.4) was added to the first tube, 200 µL TBS without target to the second tube (negative selection of phages) and beads were incubated on the rolling mixer for 20 min at 30 rpm. Tubes were placed back into the magnet, remaining solution was discarded and the beads washed twice with TBS-T. Beads were blocked with 2% milk powder (Carl Roth) in TBS for 1 h at 4° C. and 30 rpm. While biotinylated FN-B coated SA-beads were blocked for another 30 min, 7×10$^{13}$ (1st round) or 7×10$^{12}$ (2nd and 3rd round) phages were added to the uncoated SA beads in 1 mL 2% milk powder in TBS and incubated for 30 min at RT, 30 rpm (negative selection). The blocking solution of target-coated beads was discarded; beads washed twice with TBS-T and phage supernatant from negative selection was added. Target-coated beads were incubated with the phage suspension for 1 h at RT and 30 rpm. Subsequently, unbound phages were washed off, washing the beads six times with TBS-T and twice with TBS. To elute bound phages, a pH-shift elution was performed, adding 50 µL 100 mM trimethylamine (TEA) to the washed beads. The TEA bead suspension was incubated for 6 min at 3000 rpm, placed back into the magnet and supernatant transferred to a fresh tube containing 100 µL 1M Tris/HCl pH 7 for neutralization. A second elution step was performed by adding 50 µL 100 mM glycine (pH 2) to the target-coated beads and incubating the mixture for 10 min in a thermomixer at max rpm. Tubes were placed back into the magnet and the supernatant was transferred to the Tris/TEA mixture from the first elution. Phage eluate was used to infect exponentially growing E. coli XL1-Blue (Agilent) for phage pool amplification. 1800 µL E. coli XL1-Blue cells at an $OD_{600}$ of 0.5 were added to the eluate and incubated for 30 min at 37° C. without and for 30 min at 37° C. with agitation at 150 rpm. The infected XL1-Blue cells were then dispended on two large agar plates containing 100 µg/mL carbenicillin and 0.4% glucose and incubated overnight at 37° C., before phage rescue was performed on the following day.

For phage rescue 4 mL LB media were distributed per plate and cells scraped off with a cell scraper. A 50-mL culture was inoculated to a final $OD_{600}$ of 0.2. Cells were grown until an $OD_{600}$ of 0.5 and infected with $0.5 \times 10^{12}$ VCSM13 helper phages (Agilent) for phage production from phagemid vector. E. coli XL1-Blue cells were incubated for 30 min, 37° C., without agitation followed by 30 min, 37° C., with agitation at 150 rpm. The bacterial suspension was centrifuged at 4500×g for 10 min at RT and the supernatant discarded. Bacterial pellets were taken up in 50 mL LB media (supplemented with 100 µg/mL carbenicillin, 25 µg/mL kanamycin, 1 mM IPTG) for induction of protein production and E. coli phage production cultures grown overnight at 30° C., 250 rpm. E. coli cells were harvested by centrifugation at 4500×g for 15 min, 4° C. 10 mL PEG/NaCl solution (25% (w/v) polyethylene glycol, 15% (w/v) NaCl) was added to 40 mL of the phage containing supernatant, inverted and placed on ice for 30 min. Phage particles were precipitated via centrifugation at 15.000×g, 20 min at 4° C. Supernatants were discarded and phage pellets were taken up in 1600 µL Tris/HCl (pH 8.0) for subsequent centrifugation at 15.000×g, 10 min at 4° C. The phage containing supernatant was added to 400 µL PEG/NaCl again and incubated on ice for 20 min. After the second PEGNaCl precipitation, tubes were centrifuged at 15.000×g, 15 min at 4° C. Phage pellets were re-suspended in 800 µL Tris/HCl and heated to 65° C., 15 min in a final purification step. Phage suspensions were centrifuged at RT, 15.000×g for 10 min, supernatants were taken and phage particle concentration was determined photometrically using the dual wavelength modus $OD_{269}$-$OD_{320}$. Phage concentrations were calculated according to the nucleotide content and molar extinction coefficient of M13 phages (Barbas et al. 2004).

Hit Identification of Selected Cystine-Knot Miniproteins

In the identification process, enriched screening pool phagemids derived from the $3^{rd}$ screening round were prepared in order to amplify cystine-knot miniprotein sequences by PCR. PCR-inserts were cloned into the expression vector pET-32-LibEx, a derivative of pET-32a (Novagen), to enable an expression of cystine-knot miniproteins as thioredoxin-A fusion variants. This vector carries DNA sequences in successive order encoding for E. coli thioredoxin-A to allow for efficient disulfide bond formation in the cytoplasm, a H6-tag for rapid purification, an s-tag for detection by an antibody and a thrombin cleavage site to remove the fusion tag. DNA fragments encoding for cystine-knot miniprotein sequences were introduced downstream of the thrombin cleavage site into pET-32-LibEx vector via unique Bam HI and Kpn I restriction sites. Vectors were introduced into E. coli SHuffle® T7 Express cells (New England BioLabs) via heat-shock and the cells were plated on selective agar plates. Single colonies were picked, sequenced and transferred to a 96-well plate for small scale expression in 1 mL autoinduction media (MagicMedia™, Thermo Fisher Scientific). Protein production was conducted at 30° C. and 220 rpm overnight. Cells were harvested by centrifugation at 3000×g for 15 min, lysed via incubation in buffer (20 mM Tris, 2 mM $MgCl_2$, 20 mM NaCl, pH 8) containing 0.1 mg/mL lysozyme (Merck Millipore) and 5 U/mL benzonase (Merck Millipore) combined with a freeze-thaw cycle and heated for 10 min at 80° C. After a final centrifugation (3000×g, 15 min, 4° C.) to remove cell debris, the supernatant was collected for E-PAGE™ and binding analysis. E-PAGE™ (Life Technologies) was used as a high throughput gel system to simultaneously analyze 96-probes in parallel for a quantification of produced and heat purified proteins. E-PAGE™ analysis was performed according to manufacturer's instructions.

ELISA was used as technique to analyze protein-protein interactions. Cavities of 96-well microtiter plates (Nunc MaxiSorp™, Thermo Fisher Scientific) were coated with 1 µg FN-B, bovine serum albumin (BSA, Eurobio), milk powder, streptavidin (Sigma Aldrich), T7-His-TEV-B (LD BioPharma), FN-B(8-14) (R&D Systems), lysozyme, ovalbumin (GE Healthcare Life Science), aldolase (GE Healthcare Life Science) or 0.6 µg anti-c-myc-antibody (M4439, Sigma) overnight at 4° C. The wells were washed three times with PBS-T (1×PBS with 0.1% (w/v) Tween-20), blocked with 1× Casein buffer (Sigma Aldrich) diluted in PBS for 2 h at RT and washed again as described. 20 µL, of supernatant containing the respective heat-purified fusion protein was added to 80 µL, PBS-T or 200 nM of MC-Myc-010 fusion protein (wells with anti-c-myc-antibody) diluted in PBS-T, applied to the cavities and incubated for 1 h at 4° C. After three times of washing with PBS-T, binding of the respective variant was detected with a horseradish peroxidase (HRP)-conjugated anti-S-tag antibody (ab18589 or ab19324, Abcam). Enzymatic reaction was measured with TMB as a chromogenic substrate and stopped with 0.2 M HCl after approximately 5 min. The measurement of absorbance at 450 nm was performed using an Infinite M200 PRO Microplate Reader (Tecan).

In order to compare binding signals among different plates, ELISA signals were normalized to the internal plate control (c-myc binding). Normalized FN-B signals were then referenced to normalized BSA signals to evaluate binding ability of selected cystine-knot miniproteins. In addition, the target binding signals were correlated to the protein expression rate, resulting in a ranking value for the identification of hits.

Recombinant Cystine-Knot Miniprotein Production

Recombinant protein production was carried out using E. coli SHuffle® T7 Express cells carrying pET-32-LibEx vector encoding for the respective cystine-knot miniprotein sequence in a 750-mL scale at 30° C., 120 rpm. After the culture reached an $OD_{600}$ of approximately 0.7, induction of production was achieved by adding 750 µL 1 M IPTG and incubation at 25° C., 120 rpm overnight. E. coli cells were harvested, re-suspended in 10 mL equilibration buffer, lysed by sonification and heated to 80° C. for 10 min. After centrifugation of cell debris (15.000×g for 30 min, 4° C.), the supernatant was purified by IMAC with a 1 mL HisTrap column using an ÄKTAprime™ plus system and a linear gradient from 10-500 mM imidazole in 20 min. The cystine-knot miniprotein fusion protein containing fractions were collected and dialyzed against thrombin cleavage buffer (20 mM Tris, 150 mM NaCl, 1.5 mM CaCl2 and 5% (w/v) glycerol, pH 8.45) at 4° C. overnight.

Fusion proteins were either directly used for ELISA-based assays or processed further in case that the untagged miniprotein was needed, e.g. for SPR analysis.

For this, fusion proteins were cleaved with 0.5 U of thrombin (Sigma-Aldrich) per 1 mg protein and incubated at 37° C. overnight.

Separation of protein fragments was performed by reverse phase chromatography with Agilent 1260 Infinity Quaternary LC system (Agilent) and a 3 mL RESOURCE™ RPC column (GE Healthcare) using a linear gradient from 2-80% acetonitrile in $H_2O$ supplemented with 0.05% trifluoroacetic acid (TFA). Respective fractions containing cystine-knot miniprotein were lyophilized in a RVC 2-18-CD Plus Speed-Vac (Christ) as a final step. Amount of cystine-knot miniprotein was determined by weighing and the peptides were stored in lyophilized form at −20° C. Identity was verified by mass spectrometry with a LCMS Single Quad G6130B System (Agilent Technologies) using a standard electrospray ionization protocol.

Alanine Scanning Mutagenesis of Selected MC-FN-010

In order to identify the residues within MC-FN-010 that contribute to EDB-binding an alanine scanning mutagenesis was performed. This method includes a systemic substitution of amino acids against alanine at defined sequence positions and subsequent binding analysis of the generated mutants. For generation of alanine scanning MC-FN-010 derivatives mutations were either introduced via PCR or the whole coding sequence was assembled via direct synthesis of GeneArt™ Strings™ fragments (Thermo Fisher Scientific). Respective DNA fragments were cloned into pET-32-LibEx expression vector using unique BamHI and KpnI restriction sites and introduced into *E. coli* SHuffle® T7 Express competent cells (New England BioLabs). All mutations were verified by DNA sequencing. The alanine scan mutagenesis variants were expressed in 24-well format using 5 mL of selective autoinduction media. Production and fusion protein purification was performed as described above for the 96-well format, but included a further purification step of the supernatant using HisPur™ Ni-NTA spin columns (Thermo Fisher Scientific). Binding ability and specificity of cystine-knot fusion proteins to target and off-target protein was carried out with an antibody-based ELISA assay as described above.

Surface Plasmon Resonance Spectroscopy

Binding kinetics of monomeric and trimeric cystine-knot miniprotein ligands to its target protein was determined using a Biacore T-100 device (GE Healthcare Life Science) with PBS-T as running buffer. For this, the biotinylated FN-67B89 protein (200-300 µg/mL) was captured by binding to a flow cell of a SA sensor chip (GE Healthcare Life Science). To analyze monomeric ligands an immobilized target density of maximum 750 response units (RU) was applied and for trimeric variants a RU of maximum 400 was aimed for. Binding analysis of monomeric ligands was performed using a multi cycle kinetic method with concentrations ranging from 50 to 4000 nM. A cycle started with an association period of 90 sec, followed by a dissociation period of 420 sec and a final regeneration step. Kinetic measurement was conducted applying a flow rate of 20 µL/min. Trimeric variants were analyzed under the same association and dissociation conditions, but using the single cycle kinetic measurement mode in a constant flow of 30 µL/mL. In this case the analyte concentration was between 1.25 nM to 10 nM. Binding kinetics and steady state analysis were calculated using a global kinetic fit model (1:1 Langmuir, Biacore T-100 Evaluation Software, GE Healthcare Life Science).

Immunofluorescence Staining

For immunofluorescence staining cryopreserved tumor or brain pieces were cut in five micron thick sections, fixed in ice cold acetone for 5 min and air-dried. Slides were then blocked in PBS with 3% BSA at RT for 5 min. For staining of EDB, 1 µg of the respective biotinylated cystine-knot miniprotein was incubated with 2.9 µg streptavidin-Cy3 conjugate (Rockland Immunochemicals) at RT for 30 min. The pre-formed complex was then added to the tumor sections and incubated for 30 min at 37° C. Afterwards, slides were washed three times with PBS containing 1% BSA. CD31 staining was performed with a rat anti-mouse CD31 IgG antibody (clone 390, eBioscience) diluted 1:100 in PBS with 1% BSA for 30 min at 37° C. After three washing steps in PBS, cell nuclei were stained with Hochst 33342 (Thermo Fisher Scientific) diluted 1:5000 in PBS for 30 min at RT. Slides were washed again as described above and covered with coverslips in a thin layer of mounting medium (Dako). Images were captured with a Zeiss Apotome microscope (Carl Zeiss) and analyzed with ZEN software (Carl Zeiss).

Peptide Synthesis

Trimeric Alexa Fluor 680 (AF680) conjugated ligands as well as N-terminally biotinylated miniproteins were purchased from Pepscan. All obtained peptidic constructs were stored as 100 µg aliquots at −20° C. For experiments all peptides were dissolved in 100 µL DPBS (Gibco) resulting in a concentration of 1 µg/µL. For all constructs identity was verified by ESI mass spectrometry and purity was analyzed by analytical reverse phase chromatography (Pepscan). Additionally, trimers were analyzed via SDS-PAGE and SPR in order to characterize target binding properties (binding to FN-67B89) and specificity (binding to FN-6789).

U-87 MG Xenograft Mouse Model

Human glioblastoma U-87 MG (ATCC) cell line was cultured in EMEM medium (ATCC) supplemented with 10% FCS under aseptic conditions at 37° C. with 5% $CO_2$ and 95% humidity.

Mice were housed in the animal facility at BioNTech AG and all animal protocols were approved by Tierschutzkommision des Landesuntersuchungsamts Rheinland-Pfalz. Four weeks old Fox n1/nu mice ranging in weights between approximately 25 and 28 g were obtained from Janvier. For xenograft mouse studies $7 \times 10^6$ human U-87 MG cells were subcutaneously injected into the right flank of Fox n1/nu mice and tumors were allowed to grow for approximately five weeks. Subcutaneous tumor size was determined using ellipsoid formula $$\left( \frac{\text{width} \times \text{length}^2}{2} \right).$$

All animals with tumor volume between 100-1200 mm³ were included in the studies and mice were randomly assigned to experimental cohorts.

In Vivo and Ex Vivo Imaging

Mice carrying a desired tumor size were included for analysis of biodistribution and tumor targeting of trimeric constructs. All trimeric constructs were injected intravenously via retrobulbar venous plexus in a final volume of 100 μl PBS buffer (3.34 nmol/mice). Mice (n=3 for each construct) were imaged in an IVIS Spectrum System (Perkin Elmer) using excitation range of 615-665 nm and monitoring emission signals at 695-770 nm. Imaging process was performed 1 h, 2 h or 6 h post-injection and after euthanization the tumor and specific organs were excised, imaged, weighed and cryo-conserved for further analysis. Fluorescence intensity of regions of interest was quantified using Living Image® software (PerkinElmer). Statistically significance was calculated based on triplicate data sets using two-way ANOVA analysis in GraphPad Prism.

Example 2: Screening and Selection of EDB-Specific Ligands

Since cystine-knot miniproteins have been shown to be ideally suited as agents for tumor imaging (Kimura et al. 2009; Moore et al. 2013; Miao et al. 2009; Soroceanu et al. 1998; Veiseh et al. 2007, Nielsen et al. 2010; Hackel et al. 2013; Zhu et al. 2014), we used the open chain sequence of Momordica cochinchinensis trypsin inhibitor-II (oMCoTI-II) as basis for a combinatorial phage library construction to select target binding ligands (Hernandez et al. 2000). Our first library (MCopt 1.0) comprises sequences with randomized amino acids in the first loop, scattered positions in the third loop and two variable residues in front of the first cysteine. Cystine-knot miniprotein sequences were genetically fused to the major coat protein (pVIII) of M13 phages. In addition, a second library (MCopt 2.0) was developed with randomization in the first loop of the sequence and a presentation of proteins via the minor coat protein (pIII) of M13 phages. The libraries thus distinguish in the randomized loop positions and sequence length as well as the protein presentation valency, which may lead to variation in ligand selection outcome. Both libraries were applied in parallel in order to identify cystine-knot miniproteins directed against fibronectin extra domain B (EDB) which is known to be highly expressed in different tumor entities while absent from most normal tissues expect interstitium of the ovary or synovial cells (Carnemolla et al. 1989; Castellani et al. 1994).

To generate suitable target and control proteins for the subsequent screening and hit identification process we recombinantly produced the single EDB domain (FN-B), EDB flanked by the surrounding type III domains (FN-67B89) and type III domains 6-9 without EDB (FN-6789). Correct protein sizes of all FN variants could be confirmed and yielded purity were above 93% as shown in FIG. 1A. By using a monoclonal antibody (BC-1), which distinguishes between fibronectin containing EDB and fibronectin without EDB (Carnemolla et al. 1992), we evaluated a native folding of the FN-67B89 protein. Furthermore, the C-terminally H6-tag was detected in all FN-fusion proteins (FIG. 1 B). Both phage libraries were screened in three consecutive rounds against biotinylated FN-B and after completion forty-six single clones were sequenced. In the MCopt 1.0 screening one cystine-knot miniprotein was strongly enriched, dominating the pool with 40%. Additionally, two other cystine-knot miniprotein clones were enriched with 4% and 2% (FIG. 2). In the case of the MCopt 2.0 screening three different cystine-knot miniprotein clones were enriched to a proportion of 13%, 10% and 2% of the total sequences. Interestingly, five out of six amplified sequences comprise a common R-I/V-R-(L) motif at the c-terminal end of loop 1 (FIG. 2). Encouraged by these findings, we assessed FN-B binding ability of enriched sequences resulting from the screening of the MCopt 1.0 library. To this end, cystine-knot miniproteins were expressed, C-terminally fused to thioredoxin, his-tag and s-tag (Trx-cystine-knot miniprotein), in a 96-well mini scale format. Binding of proteins to FN-B and BSA was assayed in an ELISA and additionally the expression rate of each clone was determined via E-PAGE® analysis. Based on the derived signal-to-noise ratio and the expression value, we calculated a ranking score for each candidate as a measure for FN-B interaction. Three different Trx-cystine-knot miniprotein variants showed an increased interaction to FN-B compared to the BSA control (FIG. 3) and the sequences correspond to the enriched clones from the screening pool as expected. These three candidates as well as the R-I/V-R-(L) motif containing clones from the MCopt2.0 screening were included for subsequent deeper binding analysis.

Example 3: Specificity Analysis of Enriched Cystine-Knot Miniprotein Candidates

We next focused on target binding specificity of the six remaining cystine-knot miniproteins using in-house produced EDB target proteins (FN-B and FN-67B89) as well as off-target protein (FN-6789) and different control proteins (milk powder, streptavidin and bovine serum albumin). FN-6789 represents a perfect corresponding off-target protein, because fibronectin lacking extra domain B is expressed by many different cell types (Mao and Schwarzbauer 2005). All candidates display a reasonable EDB target binding, being equally high for recombinant FN-B and FN-67B89 target proteins (FIG. 4). Variants chosen on the basis of the common R-I/V-R-(L) motif (MCopt 1.0-2/-3 and MCopt 2.0-1/-2/-3) showed medium to low off-target and control protein signals. While MCopt 1.0-2 and MCopt 1.0-3 were already identified in MCopt 1.0 hit identification, MCopt 2.0-1, -2 and -3 were solely identified from the MCopt 2.0 pool on the basis of their common motif and were thus not assayed for FN-B target binding before. MCopt 1.0-1 however which does not contain the R-I/V-R-(L)-motif failed in specificity evaluation, because we observed a high interaction to the off-target FN-6789 as well as to all control proteins expect milk powder. These data strongly indicate that the observed amino acid motif is relevant for EDB binding.

We then further assessed EDB specificity of the five promising candidates by including also commercially available T7-TEV-B (LD BioPharma), a T7-TEV N-terminally flanked EDB domain, and FN-B(8-14) (R&D Systems), EDB with C-terminal domains 8-13 and ½ of domain 14. Again, binding signals were equally high for all tested EDB containing target proteins with relatively low off-target signals (FIG. 5). Since all used target proteins present EDB in different formats, EDB alone (FN-B), flanked by an artificial N-terminal construct (T7-His-TEV), flanked by natural C- and N-terminal type III domains (FN-67B89) as well as only flanked by its neighboring natural C-terminal type III domains (FN-B(8-14)), it can be concluded that is the observed binding activities are indeed specific for the EDB center piece.

Finally, we generated dose-dependent binding data of four R-I/V-R-(L)-motif containing candidates (MCopt 1.0-2/-3 and MCopt2.0-1/-2) towards FN-B, FN-67B89 and FN-B (8-14) with different receptor saturation concentrations, as presented in FIG. 6. Background signals observed towards FN-6789 off-target are generally much lower than for all EDB containing target proteins, which indicate a clear discrimination between fibronectin type III domains in FN-6789 and EDB. As it has already been seen in specificity ELISAs before, clone MCopt 2.0-3 illustrates a high degree of unspecific binding towards the FN-6789 off-target. Even though clone MCopt 2.0-3 shares the common R-I/V-R-(L)-motif which seems to have a crucial function in EDB target binding, other residues in the randomized cystine-knot miniprotein loop one might facilitate unspecific binding e.g. due to hydrophobic interactions.

For intended application of cystine-knot miniprotein as imaging agent, we then studied binding ability of tag-free proteins by surface plasmon resonance (SPR) analysis. Surprisingly, only MCopt 1.0-3 revealed strong binding towards FN-67B89 target protein across all five candidates in the tested concentration range from 50-1000 nM (data not shown). Therefore, MCopt 1.0-3, in the following called MC-FN-010, was chosen for further analysis and optical imaging probe development.

Example 4: Mapping of the MC-FN-010 Binding Site

Even though our previous findings of the amino acid motif R-I/V-R-(L) in different selected cystine-knot miniproteins already suggested a high sequence contribution to EDB binding, we then experimentally evaluated its relevance in more detail. Single alanine substitutions in the MC-FN-010 target sequence was addressed and lead in total to fourteen derivate constructs (consecutively numbered from MC-FN-011 till MC-FN-0114 as shown in FIG. 7A). All constructs were tested against single domain FN-B. As expected, seven constructs with alanine exchanges in the beginning of the sequence still showed strong target interaction suggesting that those positions are not crucial for EDB binding. In contrast, four constructs with exchange in the common motif positions revealed loss of binding. A further alanine substitution in the fifth loop also led to a reduced target interaction, indicating its relevance as well (FIG. 7 B). These results confirm that four amino acid residues in the first loop (RIRL) and also the arginine residue in the fifth loop have a direct effect on the binding interaction to FN-67B89 or an indirect influence on the miniprotein conformation as summarized in FIG. 7 C.

Example 5: Specificity Analysis of Parental MC-FN-010 Miniprotein on Tumor Tissues We furthermore studied the specificity of parental MC-FN-010 in a cellular context using an U-87 MG tumor xenograft section comprising the natural EDB protein in the microenvironment. Human glioblastoma tumors are known to harbour the fibronectin EDB isoform in vascular structures (Mariani et al. 1997). Based on alanine scanning mutagenesis, we generated a negative control construct (MC-FN-0115) with alanine substitutions in three positions (PMCTQRANRIAACRRDSDCTGACICRGNGYCG (SEQ ID NO: 27). For immunofluorescence imaging experiments MC-FN-010 and MC-FN-0115 as biotinylated formats were tetramerized with Cy3-labeled streptavidin. Tetramerized MC-FN-010-bio almost solely decorated areas around vessels as confirmed with an Alexa Fluor 647-conjugated antibody against CD31, a ubiquitously expressed surface protein of endothelial cells reputed as vascular marker (FIG. 8). Merge image of Cy3 and Alexa Fluor 647 demonstrates the co-localization of both fluorescence signals associated to blood vessels. In addition, a localization of tetramerized MC-FN-010 in surrounding perivascular areas could be detected. In contrast, U-87 MG tumor sections stained with the negative control construct MC-FN-0115 showed no fluorescence signal at all (FIG. 8). No fluorescence signal for tetramerized MC-FN-010 and MC-FN-0115 was observed on normal mouse brain section (FIG. 12).

Example 6: Binding and Affinity of Cystine-Knot Miniproteins to FN-67B89

Prior to a usage of targeting proteins as diagnostic tool, they need to be specifically conjugated with imaging agents (Spicer und Davis 2014). Our lead candidate MC-FN-010 contains a lysine in loop one, which is not favorable for selective agent linkage to primary amines. Based on our previous analysis this amino acid does not actively contributes to EDB binding, so we choose a derivate construct MC-FN-016 as a second candidate. We observed a binding of Trx-MC-FN-016 towards FN-67B89 in a dose-dependent manner with signals that were comparable with parental Trx-MC-FN-010 (FIG. 9). In contrast, the overall background signal to FN-6789 was continuously relatively low. Both cystine-knot miniprotein candidates exclusively targets FN-67B89 with no interaction to FN-6789, which is important since fibronectin is widely expressed in multiple cell types (Pankov und Yamada 2002). The affinities of tag-free MC-FN-010 and MC-FN-016 towards biotinylated FN-67B89 were assayed by SPR analysis. The binding kinetics of both cystine-knot miniproteins revealed low binding affinity in the one digit micromolar range with fast off-rates (FIG. 10A).

Example 7: Generation and Evaluation of an EDB-Specific Optical Imaging Probe

To achieve a stronger binding strength, the ligands were chemically trimerized via oxime ligation to take advantage of a potential avidity effect. Additionally, the molecule was tagged with a near-infrared fluorescence dye, Alexa Fluor 680, to enable an observation of distribution and localization after administration into mice. After chemical synthesis of all three trimeric constructs, different assays were performed in order to control the correct size and purity. SDS-PAGE and reverse phase chromatography analysis revealed no critical conspicuities in all constructs (data not shown). Notably, our oligomerization strategy led to enormously improved affinity of both EDB binding cystine-knot miniproteins (AF680-(MC-FN-010)$_3$ and AF680-(MC-FN-016)$_3$) resulting in a three digit picomolar affinity constant and remarkably slower off-rates compared to the monomeric variants (FIG. 10 B).

Previously, it was shown that other EDB targeting molecules were applied as diagnostic reagent to image glioblastomas (Albrecht et al. 2016; Mohammadgholi et al. 2017). To this end, we focused on the feasibility of our EDB binding cystine-knot miniproteins to target human glioblastoma-bearing Fox n1/nu mice. Whole-body and ex vivo imaging of organs were performed after intravenous (r. o.) injection of 3.34 nmol AF680-(MC-FN-010)$_3$, AF680-(MC-FN-016)$_3$ and the negative control AF680-(MC-FN-0115)$_3$. FIG. 11A presents fluorescence images with strong tumor signals resulting from AF680-(MC-FN-010)$_3$ and AF680-(MC-FN-016)$_3$ compared to the negative control AF680-(MC-FN-0115)$_3$. All trimeric constructs could also be detected in liver, gallbladder and kidney in the early timeframe. After 6 h the different organ signals decreased expect for the gallbladder, but importantly the tumor signal generated from AF680-(MC-FN-010)$_3$ and AF680-(MC-FN- 016)₃ remained. Furthermore, the fluorescence signals of the organs were correlated with their respective weights as depicted in FIG. 11 B. The parental AF680-(MC-FN-010)₃ had significantly stronger tumor signals in comparison to the negative control at all time points. However, AF680-(MC-FN-016)₃ revealed lower signals than AF680-(MC-FN-010)₃, but nevertheless higher as the negative control AF680-(MC-FN-0115)₃.

Example 8: Specific Binding of MC-FN-010 to Tissue Sections Derived from the Human U-87 MG Glioblastoma Cell Line Grown as Mouse Xenograft Tumor Cryopreserved tumor or brain pieces were cut in six micron thick sections, fixed in ice cold acetone for 5 min and air-dried. Slides were then blocked in PBS with 3% BSA at RT for 5 min. For staining of EDB, 0.1 µg AF680-(MC-FN-010)₃ and anti-mouse CD31 antibody (RB-10333-P1, Thermo Fisher) diluted 1:100 in PBS with 1% BSA was then added to the tumor sections and incubated for 30 min at 37° C. Afterwards, slides were washed three times with PBS containing 1% BSA. CD31 staining of primary anti-mouse CD31 antibody was detected with a secondary anti-rabbit IgG-Cy3 antibody (111-165-003, Jackson ImmunoResearch) diluted 1:400 in PBS with 1% BSA for 30 min at 37° C. After three washing steps in PBS, cell nuclei were stained with Hochst 33342 (Thermo Fisher Scientific) diluted 1:5000 in PBS for 30 min at RT. Slides were washed again as described above and covered with coverslips in a thin layer of mounting medium (Dako). Images were captured with a Zeiss Apotome microscope (Carl Zeiss) and analyzed with ZEN software (Carl Zeiss). FIG. 13 presents an additional immunofluorescence staining with the trimeric constructs (AF680-(MC-FN-010)₃ and control AF680-(MC-FN-0115)₃) on human glioblastoma xenograft tumor and normal brain tissue samples. AF680-(MC-FN-010)₃ stained the areas around the tumor vessels on U-87 MG sections that was localized with the vascular marker CD31, while the control AF680-(MC-FN-0115)₃ showed no staining at all. No staining was observed in normal mouse brain section with AF680-(MC-FN-010) 3, indicating tumor vasculature specificity.

Example 9: Specific Tumor Targeting with Selected Cystine-Knot Miniprotein

U-87 MG xenograft mouse model was arised as described in Example 1 (U-87 MG xenograft mouse model).

For in vivo competition experiment, mice carrying a desired tumor size (~200 mm³) were injected intravenously via retrobulbar venous plexus with the unlabeled trimeric probe (DOTA-(MC-FN-016)₃) in 3- or 5-fold molar excess as competitor along with AF680-labeled trimer (3.34 nmol). Mice were imaged in an IVIS Spectrum System (Perkin Elmer) using excitation range of 615-665 nm and monitoring emission signals at 695-770 nm. Whole mice imaging process was performed 1 h, 2 h or 6 h post-injection. After 6 h mice were euthanized, tumor and specific organs were excised, imaged, weighed and cryo-conservated for further analysis. Fluorescence intensity of regions of interest was quantified using Living Image® software (PerkinElmer). The kinetics of tumor fluorescence intensity in these mice was compared by in vivo and ex vivo imaging to that in mice, which were treated with the labeled AF680-(MC-FN-016)₃ without competitor. DOTA-(MC-FN-016)₃ was well suited for the competition experiment as the measured apparent binding constant to FN-67B89 was comparable to AF680-(MC-FN-016)₃ (FIG. 15). The tumor signals measured in vivo in mice treated with the competitor were substantially reduced at each time point (FIG. 14 A). As in previous experiments (FIG. 11), the negative control peptide AF680-(MC-FN-0115)₃ showed no enrichment in the tumor. After 6 h the mice were euthanized, the tumor and organs were excised, and ex vivo fluorescence imaging analysis (FIG. 14 B) was performed. Measured fluorescence intensities were normalized to the tumor weight. Competition by the unlabeled trimer was confirmed and dependency of signal reduction on the competitor dose was observed (FIG. 14 C). Injection of the competitor 30 min prior to the labeled trimer was found to be more effective as compared to its concurrent injection.

Our study describes the selection of a cystine-knot miniprotein (MC-FN-010) out of a phage library against recombinant EDB. MC-FN-010 and its derivate MC-FN-016 were engineered as molecular scaffolds for tumor imaging approaches. Both EDB-binding molecules showed strong accumulation in U87-MG xenograft tumor and low background signals except for the kidneys. These results demonstrate the high potential of MC-FN-010 and MC-FN-016 as agents for tumor diagnostic technology.

REREFENCES

Albrecht, Valerie; Richter, Antonia; Pfeiffer, Sarah; Gebauer, Michaela; Lindner, Simon; Gieser, Eugenie et al. (2016): Anticalins directed against the fibronectin extra domain B as diagnostic tracers for glioblastomas. In: *International journal of cancer* 138 (5), S. 1269-1280. DOI: 10.1002/ijc.29874.

Barbas, Carlos F.; Burton, D. R.; Scott, J. K.; Silverman, G. J. (2004): Phage Display: Cold Spring Harbor Laboratory Pr.

Carnemolla, B.; Balza, E.; Siri, A.; Zardi, L.; Nicotra, M. R.; Bigotti, A.; Natali, P. G. (1989): A tumor-associated fibronectin isoform generated by alternative splicing of messenger RNA precursors. In: *The Journal of cell biology* 108 (3), S. 1139-1148.

Carnemolla, Barbara; Leprini, Alessandra; Allemanni, Giorgio; Saginati, Marc; Zardi, Luciano (1992): The inclusion of the type III repeat ED-B in the fibronectin molecule generates conformational modifications that unmask a cryptic sequence. In: *Journal of Biological Chemistry* 267 (34), S. 24689-24692.

Castellani, Patrizia; Viale, Giuseppe; Dorcaratto, Alessandra; Nicolo, Guido; Kaczmarek, Janusz; Querze, Germano; Zardi, Luciano (1994): The fibronectin isoform containing the ed-b oncofetal domain. A marker of angiogenesis. In: *Int. J. Cancer* 59 (5), S. 612-618. DOI: 10.1002/ijc.2910590507.

Hackel, Benjamin J.; Kimura, Richard H.; Miao, Zheng; Liu, Hongguang; Sathirachinda, Ataya; Cheng, Zhen et al. (2013): 18F-fluorobenzoate-labeled cystine knot peptides for PET imaging of integrin αvβ6. In: *Journal of nuclear medicine: official publication, Society of Nuclear Medicine* 54 (7), S. 1101-1105. DOI: 10.2967/jnumed.112.110759.

Hernandez, J. F.; Gagnon, J.; Chiche, L.; Nguyen, T. M.; Andrieu, J. P.; Heitz, A. et al. (2000): Squash trypsin inhibitors from *Momordica cochinchinensis* exhibit an atypical macrocyclic structure. In: *Biochemistry* 39 (19), S. 5722-5730.

Kimura, Richard H.; Cheng, Zhen; Gambhir, Sanjiv Sam; Cochran, Jennifer R. (2009): Engineered knottin peptides: a new class of agents for imaging integrin expression in living subjects. In: *Cancer Research* 69 (6), S. 2435-2442. DOI: 10.1158/0008-5472.CAN-08-2495.

Mao, Yong; Schwarzbauer, Jean E. (2005): Fibronectin fibrillogenesis, a cell-mediated matrix assembly process. In: *Matrix biology: journal of the International Society for Matrix Biology* 24 (6), S. 389-399. DOI: 10.1016/j.matbio.2005.06.008.

Mariani, G.; Lasku, A.; Balza, E.; Gaggero, B.; Motta, C.; Di Luca, L. et al. (1997): Tumor targeting potential of the monoclonal antibody BC-1 against oncofetal fibronectin in nude mice bearing human tumor implants. In: *Cancer* 80 (12 Suppl), S. 2378-2384.

Miao, Zheng; Ren, Gang; Liu, Hongguang; Kimura, Richard H.; Jiang, Lei; Cochran, Jennifer R. et al. (2009): An engineered knottin peptide labeled with 18F for PET imaging of integrin expression. In: *Bioconjugate chemistry* 20 (12), S. 2342-2347. DOI: 10.1021/bc900361g.

Mohammdgholi, Mohsen; Sadeghzadeh, Nourollah; Erfani, Mostafa; Abediankenari, Saeid; Abedi, Seyed Mohammad; Emrarian, Iman et al. (2017): Human Fibronectin Extra-Domain B (EDB)-Specific Aptide (APTEDB) Radiolabelling with Technetium-99m as a Potent Targeted Tumour-Imaging Agent. In: *Anti-cancer agents in medicinal chemistry*. DOI: 10.2174/1871520617666170918125020.

Moore, Sarah J.; Hayden Gephart, Melanie G.; Bergen, Jamie M.; Su, YouRong S.; Rayburn, Helen; Scott, Matthew P.; Cochran, Jennifer R. (2013): Engineered knottin peptide enables noninvasive optical imaging of intracranial medulloblastoma. In: *Proceedings of the National Academy of Sciences of the United States of America* 110 (36), S. 14598-14603. DOI: 10.1073/pnas.1311333110.

Nielsen, Carsten H.; Kimura, Richard H.; Withofs, Nadia; Tran, Phuoc T.; Miao, Zheng; Cochran, Jennifer R. et al. (2010): PET imaging of tumor neovascularization in a transgenic mouse model with a novel 64Cu-DOTA-knottin peptide. In: *Cancer Research* 70 (22), S. 9022-9030. DOI: 10.1158/0008-5472.CAN-10-1338.

Pankov, Roumen; Yamada, Kenneth M. (2002): Fibronectin at a glance. In: *Journal of cell science* 115 (20), S. 3861-3863.

Soroceanu, L.; Gillespie, Y.; Khazaeli, M. B.; Sontheimer, H. (1998): Use of chlorotoxin for targeting of primary brain tumors. In: *Cancer Research* 58 (21), S. 4871-4879.

Spicer, Christopher D.; Davis, Benjamin G. (2014): Selective chemical protein modification. In: *Nature communications* 5, S. 4740. DOI: 10.1038/ncomms5740.

Veiseh, Mandana; Gabikian, Patrik; Bahrami, S-Bahram; Veiseh, Omid; Zhang, Miqin; Hackman, Robert C. et al. (2007): Tumor paint: a chlorotoxin:Cy5.5 bioconjugate for intraoperative visualization of cancer foci. In: *Cancer Research* 67 (14), S. 6882-6888. DOI: 10.1158/0008-5472.CAN-06-3948.

Zhu, Xiaohua; Li, Jinbo; Hong, Yeongjin; Kimura, Richard H.; Ma, Xiaowei; Liu, Hongguang et al. (2014): 99mTc-labeled cystine knot peptide targeting integrin αvβ6 for tumor SPECT imaging. In: *Molecular Pharmaceutics* 11 (4), S. 1208-1217. DOI: 10.1021/mp400683q.

The invention claimed is:

1. A Fibronectin Extra Domain B (EDB) binding peptide which comprises the amino acid sequence:

(Xaa)n1 Cys (Xaa)n2 Arg Ile/Val Arg Leu(Xaa)n3 Cys (Xaa)n4 Cys (Xaa)n5 Cys (Xaa)n6 Cys (Xaa)n7 Cys (Xaa)n8 (SEQ ID NO: 4)

wherein the Cys residues form a cystine knot structure, each Xaa is independently any amino acid, and n1, n2, n3, n4, n5, n6, n7, and n8 are the respective numbers of amino acids, wherein n1 is 0 to 4,
n2 is 3 to 10,
n3 is 0 to 3,
n4 is 3 to 7,
n5 is 2 to 6,
n6 is 1 to 3,
n7 is 3 to 7,
n8 is 0 to 4, and each amino acid Xaa and the number of amino acids n1, n2, n3, n4, n5, n6, n7 and n8 are selected such that a cystine knot structure can form between the Cys residues.

2. The EDB binding peptide of claim 1, wherein
n1 is 1 or 2,
n2 is 4, 5, 6 or 7,
n3 is 0 or 1,
n4 is 4, 5 or 6,
n5 is 2, 3 or 4,
n6 is 1 or 2,
n7 is 4, 5 or 6, and
n8 is 1 or 2.

3. The EBD binding peptide of claim 1, which comprises the amino acid sequence:

(Xaa)n1 Cys (Xaa)n2 Arg Ile/Val Arg Leu (Xaa)n3 Cys Arg Arg Asp Ser Asp Cys (Xaa)n5 Cys Ile Cys Arg Gly Asn Gly Tyr Cys (Xaa)n8 (SEQ ID NO: 5), or (Xaa)n1 Cys (Xaa)n2 Arg Ile/Val Arg Leu (Xaa)n3 Cys Arg Arg Asp Ser Asp Cys (Xaa)n5 Cys Ile Cys Arg Gly Asn Gly Tyr Cys Gly (SEQ ID NO: 6).

4. The EDB binding peptide of claim 1, which comprises an amino acid sequence selected from:
(i) SerValCysLysAsnValSerIleMetArgIleArgLeuCysArgArgAspSerAspCys ProGlyAlaCysIleCysArgGlyAsnGlyTyrCysGly (SEQ ID NO: 8),
(ii) SerValCysAlaHisTyrAsnThrIleArgValArgLeuCysArgArgAspSerAspCys ProGlyAlaCysIleCysArgGlyAsnGlyTyrCysGly (SEQ ID NO: 9),
(iii) ProMetCysThrGlnArgLysAsnArgIleArgLeuCysArgArgAspSerAspCysThr GlyAlaCysIleCysArgGlyAsnGlyTyrCysGly (SEQ ID NO: 11),
(iv) SerValCysLysGlnAlaAsnPheValArgIleArgLeuCysArgArgAspSerAspCys ProGlyAlaCysIleCysArgGlyAsnGlyTyrCysGly (SEQ ID NO: 12),
(v) AlaMetCysThrGlnArgLysAsnArgIleArgLeuCysArgArgAspSerAspCysThr GlyAlaCysIleCysArgGlyAsnGlyTyrCysGly (SEQ ID NO: 13),
(vi) ProAlaCysThrGlnArgLysAsnArgIleArgLeuCysArgArgAspSerAspCysThr GlyAlaCysIleCysArgGlyAsnGlyTyrCysGly (SEQ ID NO: 14),
(vii) ProMetCysAlaGlnArgLysAsnArgIleArgLeuCysArgArgAspSerAspCysThr GlyAlaCysIleCysArgGlyAsnGlyTyrCysGly (SEQ ID NO: 15),
(viii) ProMetCysThrAlaArgLysAsnArgIleArgLeuCysArgArgAspSerAspCysThr GlyAlaCysIleCysArgGlyAsnGlyTyrCysGly (SEQ ID NO: 16),
(ix) ProMetCysThrGlnAlaLysAsnArgIleArgLeuCysArgArgAspSerAspCysThr GlyAlaCysIleCysArgGlyAsnGlyTyrCysGly (SEQ ID NO: 17),
(xi) ProMetCysThrGlnArgAlaAsnArgIleArgLeuCysArgArgAspSerAspCysThr GlyAlaCysIleCysArgGlyAsnGlyTyrCysGly (SEQ ID NO: 18),
(xii) ProMetCysThrGlnArgLysAlaArgIleArgLeuCysArgArgAspSerAspCysThr GlyAlaCysIleCysArgGlyAsnGlyTyrCysGly (SEQ ID NO: 19),
(xiii) ProMetCysThrGlnArgLysAsnArgIleArgLeuCysAlaArgAspSerAspCysThr GlyAlaCysIleCysArgGlyAsnGlyTyrCysGly (SEQ ID NO: 24), and
(xiii) ProMetCysThrGlnArgLysAsnArgIleArgLeuCysArgAlaAspSerAspCysThr GlyAlaCysIleCysArgGlyAsnGlyTyrCysGly (SEQ ID NO: 25).

5. The EDB binding peptide of claim 1, which forms or is part of a scaffold, and/or which is stabilized by a covalent modification.

6. The EDB binding peptide of claim 5, which is stabilized by a covalent modification, wherein said covalent modification is cyclization via one or more disulfide bridges.

7. The EDB binding peptide of claim 1, which forms and/or is part of an inhibitor cystine knot structure.

8. A Fibronectin Extra Domain B (EDB) binding agent comprising the EDB binding peptide of claim 1.

9. The EDB binding agent of claim 8, wherein the EDB binding peptide is covalently and/or non-covalently associated with at least one further moiety selected from a carrier protein, a label, a reporter, and a tag.

10. An EDB binding agent, which comprises at least two subunits which are covalently and/or non-covalently associated, each of said subunits comprising the EDB binding peptide of claim 1, wherein the EDB binding peptides are identical or different.

11. The EDB binding agent of claim 8, covalently and/or non-covalently associated with at least one detectable label or reporter and/or at least one therapeutic effector moiety.

12. A recombinant nucleic acid which encodes the EDB binding peptide of claim 1.

13. A host cell comprising the recombinant nucleic acid of claim 12.

14. A test kit or an assay device comprising the EDB binding peptide of claim 1.

15. A method for assaying for the presence and/or amount of Fibronectin Extra Domain B (EDB) in a sample comprising using the EDB binding peptide of claim 1, comprising:
(i) contacting a sample with the EDB binding peptide or an EDB binding agent comprising the EDB binding peptide, and
(ii) detecting the formation of and/or determining the quantity of a complex between the EDB binding peptide or the EDB binding agent and EDB.

16. A method for diagnosis, detection or monitoring of cancer in a patient comprising assaying for the presence and/or amount of Fibronectin Extra Domain B (EDB) in said patient, comprising assaying a biological sample isolated from said patient according to the method of claim 15.

17. A pharmaceutical composition comprising the EDB binding peptide of claim 1.

18. A method of treating a patient comprising administering to the patient the EDB binding peptide of claim 1, wherein the patient has cancer or is at risk of developing cancer.

19. The EDB binding peptide of claim 2, wherein
n2 is 5 or 6,
n4 is 5,
n5 is 3,
n6 is 1, and
n7 is 5.

* * * * *